United States Patent
Konradi et al.

(10) Patent No.: US 7,595,318 B2
(45) Date of Patent: Sep. 29, 2009

(54) POLYETHYLENE GLYCOL CONJUGATES OF HETEROCYCLOALKYL CARBOXAMIDO PROPANOIC ACIDS

(75) Inventors: Andrei Konradi, Burlingame, CA (US); Michael A. Pleiss, Sunnyvale, CA (US); Jenifer L. Smith, San Francisco, CA (US); Christopher M. Semko, Fremont, CA (US); Chris Vandevert, San Francisco, CA (US)

(73) Assignee: Elan Pharmaceuticals, Inc., S. San Francisco, CA (US)

( * ) Notice: Subject to any disclaimer, the term of this patent is extended or adjusted under 35 U.S.C. 154(b) by 384 days.

(21) Appl. No.: 11/042,734

(22) Filed: Jan. 24, 2005

(65) Prior Publication Data

US 2005/0238614 A1 Oct. 27, 2005

Related U.S. Application Data

(60) Provisional application No. 60/538,573, filed on Jan. 23, 2004.

(51) Int. Cl.
*A61K 31/497* (2006.01)
*A61K 31/425* (2006.01)
*C07D 295/00* (2006.01)
*C07D 277/04* (2006.01)

(52) U.S. Cl. .................... 514/252.1; 514/365; 544/358; 548/146

(58) Field of Classification Search ............... 514/252.1, 514/365; 544/358; 548/146
See application file for complete search history.

(56) References Cited

U.S. PATENT DOCUMENTS

| | | | |
|---|---|---|---|
| 4,604,103 A | 8/1986 | Campbell | |
| 5,510,332 A | 4/1996 | Kogan et al. | |
| 6,436,904 B1 * | 8/2002 | Ashwell et al. | 514/19 |
| 6,489,300 B1 * | 12/2002 | Thorsett et al. | 514/19 |
| 6,525,026 B2 * | 2/2003 | Thorsett et al. | 514/19 |
| 6,900,179 B2 * | 5/2005 | Thorsett et al. | 514/19 |
| 7,229,970 B2 * | 6/2007 | Thorsett et al. | 514/19 |
| 2005/0065192 A1 | 3/2005 | Yednock et al. | |
| 2005/0215565 A1 * | 9/2005 | Karlik et al. | 514/253.09 |
| 2006/0013799 A1 | 1/2006 | Konradi et al. | |
| 2007/0021555 A1 | 1/2007 | Konradi et al. | |
| 2007/0037804 A1 | 2/2007 | Stappenbeck et al. | |

FOREIGN PATENT DOCUMENTS

| | | |
|---|---|---|
| WO | WO96/01644 | 1/1996 |
| WO | WO 01/54690 | 8/2001 |
| WO | WO 2004/066931 | 8/2004 |

OTHER PUBLICATIONS

PEGylation from Wikipedia.*
Copending U.S. Appl. Nos. 10/763,539 and 11/177,748.*
Huryn et al., *Bioorg. Med. Chem. Ltr.* (2004) 14:1651-1654.
International Search Report for International Application PCT/US2005/002478.
Desai, Manoj C. et al., "Polymer Bound EDC (P-EDC): A Convenient Reagent for Formation of an Amide Bond", Tetrahedron Letters, 34(48), pp. 7685-7688 (1993).

* cited by examiner

*Primary Examiner*—Golam M. M. Shameem
*Assistant Examiner*—Susannah Chung
(74) *Attorney, Agent, or Firm*—McDonnell Boehnen Hulbert & Berghoff LLP

(57) ABSTRACT

Disclosed are conjugates which bind VLA-4. Certain of these conjugates also inhibit leukocyte adhesion and, in particular, leukocyte adhesion mediated by VLA-4. Such conjugates are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The conjugates can also be administered for the treatment of inflammatory brain diseases such as multiple sclerosis.

23 Claims, No Drawings

POLYETHYLENE GLYCOL CONJUGATES OF HETEROCYCLOALKYL CARBOXAMIDO PROPANOIC ACIDS

CROSS REFERENCE TO RELATED APPLICATIONS

This application claims priority from U.S. Provisional Application Ser. No. 60/538,573 filed Jan. 23, 2004, which is incorporated herein by reference in its entirety.

BACKGROUND OF THE INVENTION

1. Field of the Invention

This invention relates to compounds that inhibit leukocyte adhesion and, in particular, leukocyte adhesion mediated by alpha 4 integrins. The compounds of this invention are characterized as conjugates containing one or more polyethylene glycol substituents covalently attached thereto. Such conjugates demonstrate enhanced serum half-life and other advantageous pharmacokinetic properties as compared to compounds lacking polyethylene glycol substituents.

2. State of the Art

The physical interaction of inflammatory leukocytes with each other and other cells of the body plays an important role in regulating immune and inflammatory responses [Springer, T. A. Nature, 346, 425, (1990); Springer, T. A. Cell 76, 301, (1994)]. Many of these interactions are mediated by specific cell surface molecules collectively referred to as cell adhesion molecules. These adhesion molecules have been sub-divided into different groups on the basis of their structure. One family of adhesion molecules which is believed to play a important role in regulating immune and inflammatory responses is the integrin family. This family of cell surface glycoproteins has a typical non-covalently linked heterodimer structure.

The particular integrin subgroup of interest herein involves the alpha 4 ($\alpha$4) chain, which can pair with two different beta chains beta1 ($\beta$1) and beta7 ($\beta$7) [Sonnenberg, A. ibid]. The $\alpha$4$\beta$1 pairing occurs on many circulating leukocytes (for example lymphocytes, monocytes and eosinophils) although it is absent or only present at low levels on circulating neutrophils. VLA-4 (Very Late Antigen-4, also referred to as $\alpha_4\beta_1$ integrin and as CD49d/CD29), first identified by Hemler and Takada[1] is a member of the $\beta$1 integrin family of cell surface receptors. VLA-4 consists of an $\alpha$4 chain and $\beta$1 chain. There are at least nine $\beta$1 integrins, all sharing the same $\beta$1 chain and each having a distinct a chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells.

VLA-4 ($\alpha$4$\beta$1 integrin) binds to an adhesion molecule called Vascular Cell Adhesion Molecule-1 (or VCAM-1) which is frequently up-regulated on endothelial cells at sites of inflammation [Osborne, L. Cell, 62, 3 (1990)]. VCAM-1 is a non-matrix molecule which is an expressed receptor that is believed to be responsible for trafficking leukocytes into the central nervous system (CNS). $\alpha$4$\beta$1 has also been shown to bind to at least three sites in the matrix molecule fibronectin [Humphries, M. J. et al. Ciba Foundation Symposium, 189, 177, (1995)]. Distinct epitopes of VLA-4 are responsible for the fibronectin and VCAM-1 binding activities and each has been demonstrated to be independently inhibited.[2] Based on data obtained with monoclonal antibodies in animal models it is believed that the interaction between $\alpha$4$\beta$1 and ligands on other cells and the extracellular matrix plays an important role in leukocyte migration and activation [Yednock, T. A. et al, Nature, 356, 63, (1992).

The integrin generated by the pairing of $\alpha$4 and $\beta$7 has been termed LPAM-1 [Holzmann, B and Weissman, I. EMBO J. 8, 1735, (1989)] and like $\alpha$4$\beta$1, can bind to VCAM-1 and fibronectin. In addition, .alpha.4.beta.7 binds to an adhesion molecule believed to be involved in the homing of leukocytes to mucosal tissue termed MAdCAM-1 [Berlin, C. et al. Cell, 74, 185, (1993)]. The interaction between $\alpha$4$\beta$7 and MAdCAM-1 may also be important at sites of inflammation outside of mucosal tissue [Yang, X-D. et al. PNAS, 91, 12604 (1994)].

Intercellular adhesion mediated by VLA-4 and other cell surface receptors is associated with a number of inflammatory responses. At the site of an injury or other inflammatory stimuli, activated vascular endothelial cells express molecules that are adhesive for leukocytes. The mechanics of leukocyte adhesion to endothelial cells involve, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as multiple sclerosis (MS), meningitis, encephalitis, and a disease model called experimental autoimmune encephalomyelitis (EAE), are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive cell damage and death resulting in impaired nerve conduction and paralysis. Similar occurrences in encephalitis and meningitis indicate that these diseases can be treated with suitable cell adhesion inhibitors.

In other organ systems, tissue damage also occurs via an adhesion mechanism resulting in migration or activation of leukocytes. For example, inflammatory bowel disease[15] (including ulcerative colitis and Crohn's disease), are at least partially caused by leukocyte trafficking across the intestinal endothelium via an $\alpha$4$\beta$7 interaction with MadCAM and possibly $\alpha$4$\beta$1 interaction with VCAM-1 expressed in this tissue as well. Asthma[6-8], rheumatoid arthritis[18-21] and tissue transplant rejection[22] are all thought to have components based in interaction of $\alpha$4$\beta$1 with VCAM-1 and/or fibronectin, probably both. it has been shown that the initial insult following myocardial (heart tissue) ischemia can be further complicated by leukocyte entry to the injured tissue causing still further injury (Vedder et al.[5]). Other inflammatory or medical conditions mediated by an adhesion molecule mechanism include, by way of example, Alzheimer's disease, atherosclerosis[9-10], AIDS dementia[11], diabetes[12-14] (including acute juvenile onset diabetes, tumor metastasis[23-28], stroke, and other cerebral traumas, nephritis, retinitis, atopic dermatitis, psoriasis, and acute leukocyte-mediated lung injury such as that which occurs in adult respiratory distress syndrome.

One group of VLA-4 antagonists showing promise as anti-inflammatory agents is the class of sulfonylated-Pro-Phe compounds as set forth in, for example, U.S. Pat. No. 6,489, 300.[31] These compounds are very potent antagonists of VLA-4/VCAM-1 binding.

Owing to extensive first pass liver metabolism, these compounds are poorly orally available. Because many of the disease conditions treatable by these compounds are chronic conditions, a prolonged serum half-life for the administered compound would increase the usefulness of these kinds of compounds in treating disease in mammals.

The half-life of a drug is a measure of the time that it takes for the amount of drug in the body to decrease by one half, through normal metabolic and elimination pathways. VLA-4 inhibitors, including those disclosed in U.S. Pat. No. 6,489,300, suffer from short half-lives of around 10 to 20 minutes, even when intravenously administered in a pharmaceutical formulation. In order for the patient to retain an effective amount of the drug in their system for a reasonable period of time, either very large quantities of the drug must be administered and/or the drug must be administered many times in a day.

VLA-4 inhibitors with such short half-lives are not commercially viable therapeutic candidates. Therefore, there is a need for VLA-4 inhibitors with significantly enhanced serum half-lives; preferably in the range of hours to days.

SUMMARY OF THE INVENTION

This invention provides conjugates exhibiting VLA-4 antagonistic properties having improved serum half-lives. The conjugates of this invention contain one or more polyethylene glycol substituents covalently attached thereto. Without being limited to any theory, the improved serum half-life is believed to be associated with covalent conjugation of at least one polyethylene glycol entity onto the structure of the compound.

In one aspect, the invention provides conjugates of formula I below:

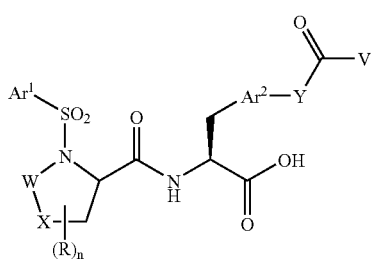

I and pharmaceutically acceptable salts thereof, wherein

R is a POAM moiety or $R_a$, where $R_a$ is selected from the group consisting of amino, hydroxyl, alkoxy, substituted alkoxy, substituted amino, alkyl and substituted alkyl, -alkyl-O-alkyl, substituted -alkyl-O-alkyl, wherein each $R_a$ is optionally substituted with a POAM moiety covalently bonded to $R_a$ optionally by a linker;

$Ar^1$ is selected from the group consisting of aryl, substituted aryl, heteroaryl and substituted heteroaryl, wherein each $Ar^1$ is optionally substituted with a POAM moiety covalently bonded to $Ar^1$ optionally by a linker;

$Ar^2$ is selected from the group consisting of aryl, substituted aryl, heteroaryl and substituted heteroaryl, wherein each $Ar^2$ is optionally substituted with a POAM moiety covalently bonded to $Ar^2$ optionally by a linker;

W is selected from the group consisting of —(CH$_2$)$_m$—, —CH$_2$—C(O)—, —C(O)—, and —CH$_2$—C(O)—CH$_2$—;

X is selected from the group consisting of —S—, —SO—, —SO$_2$ and optionally substituted —CH$_2$—;

Y is selected from the group consisting of —O—, —S— and —NR$^1$— wherein R$^1$ is selected from the group consisting of hydrogen and C$_1$-C$_5$ alkyl;

V is selected from the group consisting of
(a) a POAM moiety covalently bonded to —Y(CO)— optionally by a linker; and
(b) $V_a$, which is —NR$^2$R$^3$ wherein R$^2$ and R$^3$ are independently selected from the group consisting of alkyl and substituted alkyl; and
(c) $V_b$, which is —NR$^2$R$^3$ and represents a heterocyclic ring or a substituted heterocyclic ring,
wherein each of $V_a$ and $V_b$ is optionally substituted with a POAM moiety and where the POAM moiety is covalently bonded to the alkyl, substituted alkyl, heterocyclic rings, or substituted heterocyclic rings within $V_a$ and $V_b$ optionally by a linker;

m is an integer equal to 0, 1 or 2 and when m is 0, then X is optionally substituted —CH$_2$—; and n is an integer equal to 0, 1 or 2;

provided that at least one of R, Ar$^1$, Ar$^2$, V and —NR$^2$R$^3$ contains a POAM moiety;

further provided that when R is a POAM moiety, n is one and X is not —S—, —SO—, or —SO$_2$—;

and still further provided that the conjugate of formula I has a molecular weight of no more than 100,000.

The invention also provides pharmaceutical compositions which compositions comprise, for example, a pharmaceutically acceptable carrier and a therapeutically effective amount of a conjugate of the invention or mixtures thereof.

The invention also provides methods for treating a disease mediated, at least in part, by VLA-4 in a patient, which method comprises administering a pharmaceutical composition comprising a pharmaceutically acceptable carrier and a therapeutically effective amount of a conjugate of the invention or mixtures thereof.

The invention also includes the use of a conjugate of the invention, and pharmaceutically acceptable salts thereof, for the manufacture of a medicament for use in treating a disease mediated, at least in part, by VLA-4 in a patient.

The conjugates and pharmaceutical compositions may be used to treat disease conditions mediated, at least in part, by VLA-4 or leukocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, Sjogren's disease, atopic dermatitis, psoriasis, myocardial ischemia and acute leukocyte-mediated lung injury such as that which occurs in adult respiratory distress syndrome.

Other disease conditions which may be treated using conjugates and compositions of the present invention include, but are not limited to, inflammatory conditions such as erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

Preferably, the conjugates and pharmaceutically compositions of this invention are used in methods for treating asthma, rheumatoid arthritis and multiple sclerosis. As to this latter disease, the conjugates of this invention not only provide an anti-inflammatory effect when administered in vivo but further find use in treating conditions and diseases associated with demyelination.

The invention also provides methods of preparing the conjugates of the invention and the intermediates used in those methods.

DETAILED DESCRIPTION OF THE INVENTION

As noted above, this invention relates to conjugates which inhibit leukocyte adhesion and, in particular, leukocyte adhesion mediated, at least in part, by VLA-4.

Preferably the conjugates of formula I are of the L isomer as shown below:

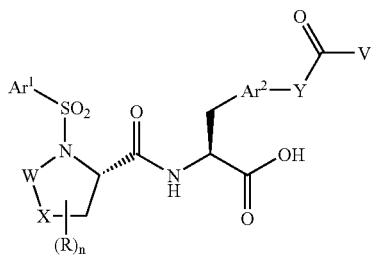

Ia

Preferred conjugates of formula I and Ia include conjugates of formula II below:

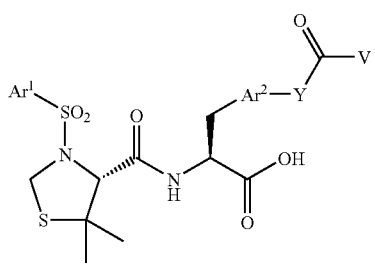

II and pharmaceutically acceptable salts thereof, wherein $Ar^1$, $Ar^2$, Y and V are as defined above;

provided that at least one of $Ar^1$, $Ar^2$, V and $-NR^2R^3$ contains a POAM moiety which optionally comprises a linker;

and further provided that the conjugate of formula II has a molecular weight of no more than 100,000.

Preferred conjugates of formula I and Ia include conjugates of formula III below:

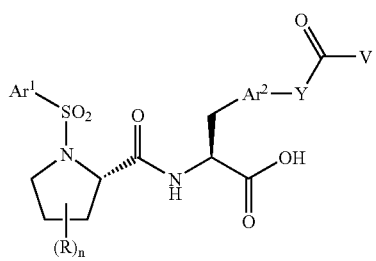

III and pharmaceutically acceptable salts thereof, wherein

R, $Ar^1$, $Ar^2$, Y, V and n are as defined above;

provided that at least one of R, $Ar^1$, $Ar^2$, V and $-NR^2R^3$ contains a POAM moiety which optionally comprises a linker;

and further provided that the conjugate of formula III has a molecular weight of no more than 100,000.

Preferred conjugates of formula I and Ia include conjugates of formula IV below:

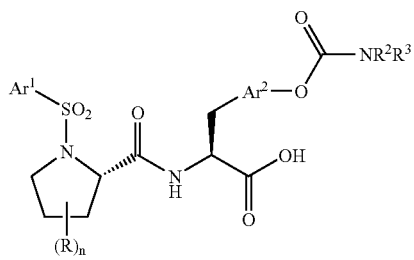

IV and pharmaceutically acceptable salts thereof, wherein

R, $R^2$, $R^3$, $Ar^1$, $Ar^2$ and n are as defined above;

provided that at least one of R, $Ar^1$, $Ar^2$, and $-NR^2R^3$ contains a POAM moiety which optionally comprises a linker;

and further provided that the conjugate of formula IV has a molecular weight of no more than 100,000.

Preferred conjugates of formula I and Ia include conjugates of formula V below:

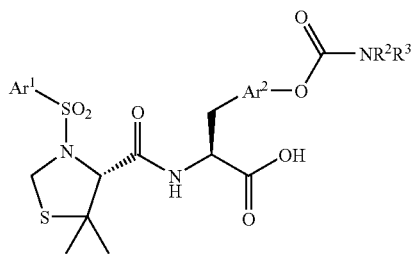

V and pharmaceutically acceptable salts thereof, wherein $R^2$, $R^3$, $Ar^1$, and $Ar^2$ are as defined above;

provided that at least one of $Ar^1$, $Ar^2$ and $-NR^2R^3$ contains a POAM moiety which optionally comprises a linker;

and further provided that the conjugate of formula V has a molecular weight of no more than 100,000.

Preferred conjugates of formula I and Ia include conjugates of formula VI:

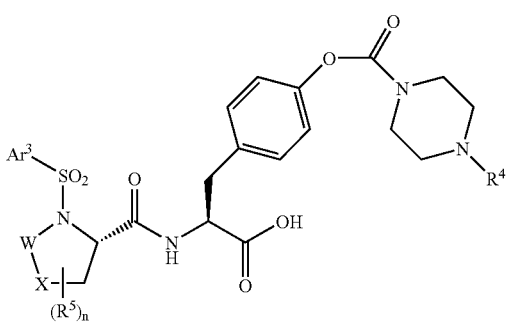

and pharmaceutically acceptable salts thereof, wherein

W is as defined above;

$R^4$ is a POAM moiety covalently bonded to the ring optionally by a linker;

$R^5$ is selected from the group consisting of alkyl and substituted alkyl;

$Ar^3$ is selected from the group consisting of aryl, substituted aryl, heteroaryl and substituted heteroaryl;

X is selected from the group consisting of —S—, —SO—, and —SO$_2$— or optionally substituted —CH$_2$—;

m is an integer equal to 0, 1 or 2;

n is an integer equal to 0 to 2;

provided that the conjugate of formula VI has a molecular weight of no more than 100,000.

Preferred conjugates of formula I and Ia include conjugates of formula VII:

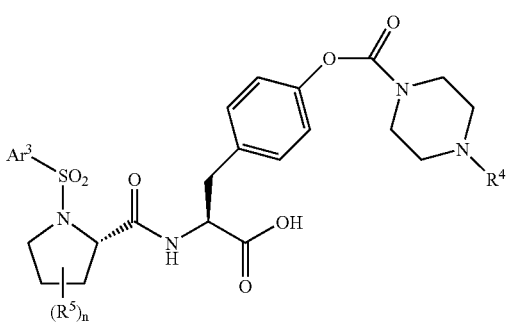

and pharmaceutically acceptable salts thereof, wherein $R^4$ is a POAM moiety covalently bonded to the ring optionally by a linker;

$R^5$ is selected from the group consisting of alkyl and substituted alkyl;

$Ar^3$ is selected from the group consisting of aryl, substituted aryl, heteroaryl and substituted heteroaryl;

n is an integer equal to 0 to 2;

provided that the conjugate of formula VII has a molecular weight of no more than 100,000.

Preferred conjugates of formula I and Ia include conjugates of formula VIII:

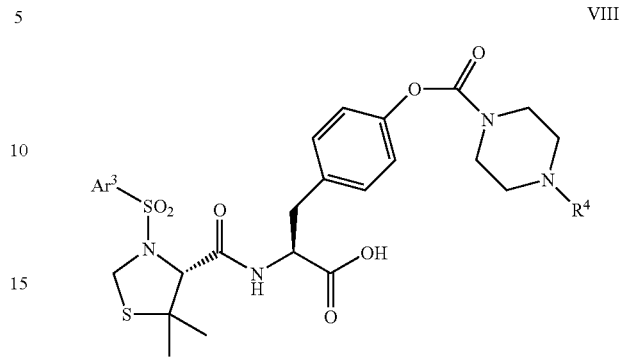

and pharmaceutically acceptable salts thereof, wherein $R^4$ is a POAM moiety POAM covalently bonded to the ring optionally by a linker;

$Ar^3$ is selected from the group consisting of aryl, substituted aryl, heteroaryl and substituted heteroaryl;

provided that the conjugate of formula VII has a molecular weight of no more than 100,000.

Preferably, when $Ar^1$ does not contain a POAM moiety, $Ar^1$ in formulas I-V and $Ar^3$ in formulas VI-VIII is selected from the group consisting of: phenyl; 4-methylphenyl; 4-t-butylphenyl; 2,4,6-trimethylphenyl; 2-fluorophenyl; 3-fluorophenyl; 4-fluorophenyl; 2,4-difluorophenyl; 3,4-difluorophenyl; 3,5-difluorophenyl; 2-chlorophenyl; 3-chlorophenyl; 4-chlorophenyl; 3,4-dichlorophenyl; 3,5-dichlorophenyl; 3-chloro-4-fluorophenyl; 4-bromophenyl; 2-methoxyphenyl; 3-methoxyphenyl; 4-methoxyphenyl; 3,4-dimethoxyphenyl; 4-t-butoxyphenyl; 4-(3'-dimethylamino-n-propoxy)-phenyl; 2-carboxyphenyl; 2-(methoxycarbonyl)phenyl; 4-(H$_2$NC(O)-)phenyl; 4-(H$_2$NC(S)-)phenyl; 4-cyanophenyl; 4-trifluoromethylphenyl; 4-trifluoromethoxyphenyl; 3,5-di-(trifluoromethyl)phenyl; 4-nitrophenyl; 4-aminophenyl; 4-(CH$_3$C(O)NH-)phenyl; 4-(PhNHC(O)NH-)phenyl; 4-amidinophenyl; 4-methylamidinophenyl; 4-[CH$_3$SC(=NH)-]phenyl; 4-chloro-3-[H$_2$NS(O)$_2$-]phenyl; 1-naphthyl; 2-naphthyl; pyridin-2-yl; pyridin-3-yl; pyridine-4-yl, pyrimidin-2-yl; quinolin-8-yl; 2-(trifluoroacetyl)-1,2,3,4-tetrahydroisoquinolin-7-yl; 2-thienyl; 5-chloro-2-thienyl; 2,5-dichloro-4-thienyl; 1-N-methylimidazol-4-yl; 1-N-methylpyrazol-3-yl; 1-N-methylpyrazol-4-yl; 1-N-butylpyrazol-4-yl; 1-N-methyl-3-methyl-5-chloropyrazol-4-yl; 1-N-methyl-5-methyl-3-chloropyrazol-4-yl; 2-thiazolyl and 5-methyl-1,3,4-thiadiazol-2-yl.

When $Ar^1$ is substituted via an optional linker with a POAM group, $Ar^1$, the POAM group and the optional linker are preferably represented by the formula:

—Ar$^1$—Z—(CH$_2$CHR$^7$O)$_p$R$^8$ wherein $Ar^1$ is selected from the group consisting of aryl, substituted aryl, heteroaryl, and substituted heteroaryl, Z is selected from the group consisting of a covalent bond, a linking group of from 1 to 40 atoms, —O—, —S— and —NR$^9$—, where R$^9$ is selected from the group consisting of hydrogen and C$_1$-C$_5$ alkyl, $R^7$ is selected from the group consisting of hydrogen and methyl;

$R^8$ is selected from the group consisting of hydrogen, alkyl, substituted alkyl, aryl, substituted aryl, and —CH$_2$CHR$^7$NR$^{10}$R$^{11}$ where $R^7$ is as defined above and $R^{10}$ and $R^{11}$ are independently selected from the group consisting of hydrogen and alkyl; and p is an integer such that the molecular weight of the POAM moiety ranges from about 100 to 100,000.

Preferably, when R does not contain a POAM moiety, the substituent of the formula:

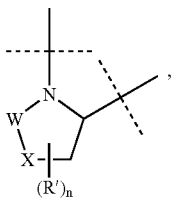

where W, X, m and n are as defined above, and R' is optionally substituted C$_1$-C$_5$ alkyl, is preferably selected from the group consisting of:

azetidinyl, thiazolidinyl, thiazolidonyl, piperidinyl, piperazinyl, thiomorpholinyl, pyrrolidinyl, pyroglutamyl, 4-hydroxypyrrolidinyl, 4-oxopyrrolidinyl, 4-fluoropyrrolidinyl, 4,4-difluoropyrrolidinyl, 4-(thiomorpholin-4-ylC(O)O-)pyrrolidinyl, 4-[CH$_3$S(O)$_2$O-]pyrrolidinyl, 3-phenylpyrrolidinyl, 3-thiophenylpyrrolidinyl, 4-aminopyrrolidinyl, 3-methoxypyrrolidinyl, 4,4-dimethylpyrrolidinyl, 4-N-Cbz-piperazinyl, 4-[CH$_3$S(O)$_2$-]piperazinyl, 5,5-dimethylthiazolindin-4-yl, 1,1-dioxo-thiazolidinyl, 1,1-dioxo-5,5-dimethylthiazolidin-2-yl and 1,1-dioxothiomorpholinyl.

When the substituent of the formula:

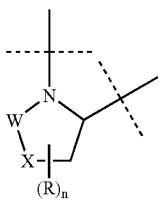

contains a POAM moiety, then preferably the substituent is of the formula:

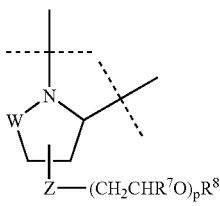

wherein

W is —(CH$_2$)$_m$— and m is an integer equal to zero, one or two;

Z is selected from the group consisting of a covalent bond, a linking group of from 1 to 40 atoms, —O—, —S— and —NR$^9$—, where R$^9$ is selected from the group consisting of hydrogen and C$_1$-C$_5$ alkyl, $R^7$ is selected from the group consisting of hydrogen and methyl;

$R^8$ is selected from the group consisting of hydrogen, alkyl, substituted alkyl, aryl, substituted aryl, and —CH$_2$CHR$^7$NR$^{10}$R$^{11}$ where $R^7$ is as defined above and $R^{10}$ and $R^{11}$ are independently selected from the group consisting of hydrogen and alkyl; and p is an integer such that the molecular weight of the POAM moiety ranges from about 100 to 100,000.

Preferably, when Ar$^2$ does not contain a POAM moiety, Ar$^2$ in formulas I-V is preferably selected from the group consisting of phenyl, 2-pyridyl, 3-pyridyl, 4-pyridyl, and 4-pyrid-2-onyl.

When Ar$^2$ contains a POAM moiety, Ar$^2$ in formulas I-V is preferably represented by the formula:

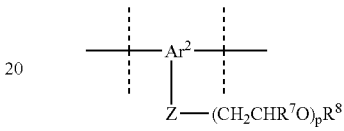

where Ar$^2$ is selected from the group consisting of aryl, substituted aryl, heteroaryl and substituted heteroaryl;

Z is selected from the group consisting of a covalent bond, a linking group of from 1 to 40 atoms, —O—, —S— and —NR$^9$—, where R$^9$ is selected from the group consisting of hydrogen and C$_1$-C$_5$ alkyl, $R^7$ is selected from the group consisting of hydrogen and methyl;

$R^8$ is selected from the group consisting of hydrogen, alkyl, substituted alkyl, aryl, substituted aryl, and —CH$_2$CHR$^7$NR$^{10}$R$^{11}$ where $R^7$ is as defined above and $R^{10}$ and $R^{11}$ are independently selected from the group consisting of hydrogen and alkyl; and p is an integer such that the molecular weight of the POAM moiety ranges from about 100 to 100,000.

Preferably, in formulas I-III, —YC(O)V is —OC(O)NR$^2$R$^3$. When R$^2$ and R$^3$ do not contain a POAM moiety, —OC(O)NR$^2$R$^3$ in formulas I-V is preferably selected from the group:

(CH$_3$)$_2$NC(O)O—; (piperidin-1-yl)C(O)O—; (4-hydroxypiperidin-1-yl)C(O)O—; (4-formyloxypiperidin-1-yl)C(O)O—; (4-ethoxycarbonylpiperidin-1-yl)C(O)O—; (4-carboxylpiperidin-1-yl)C(O)O—; (3-hydroxymethylpiperidin-1-yl)C(O)O—; (4-hydroxymethylpiperidin-1-yl)C(O)O—; (4-piperidon-1-yl ethylene ketal)C(O)O—; (piperazin-1-yl)-C(O)O—; (1-Boc-piperazin-4-yl)-C(O)O—; (4-methylpiperazin-1-yl)C(O)O—; (4-methylhomopiperazin-1-yl)C(O)O—; (4-(2-hydroxyethyl)piperazin-1-yl)C(O)O—; (4-phenylpiperazin-1-yl)C(O)O—; (4-(pyridin-2-yl)piperazin-1]-yl)C(O)O—; (4-(4-trifluoromethylpyridin-2-yl)piperazin-1-yl)C(O)O—; (4-(pyrimidin-2-yl)piperazin-1-yl)C(O)O—; (4-acetylpiperazin-1-yl)C(O)O—; (4-(phenylC(O)-)piperazin-1-yl)C(O)O—; (4-(pyridin-4'-ylC(O)-)piperazin-1-yl)C(O)O; (4-(phenylNHC(O)-)piperazin-1-yl)C(O)O—; (4-(phenylNHC(S)-)piperazin-1-yl)C(O)O—; (4-methanesulfonylpiperazin-1-yl-C(O)O—; (4-trifluoromethanesulfonylpiperazin-1-yl-C(O)O—; (morpholin-4-yl)C(O)O—; (thiomorpholin-4-yl)C(O)O—; (thiomorpholin-4'-yl sulfone)-C(O)O—; (pyrrolidin-1-yl)C(O)O—; (2-methylpyrrolidin-1-yl)C(O)O—; (2-(methoxycarbonyl)pyrrolidin-1-yl)C(O)O—; (2-(hydroxymethyl)pyrrolidin-1-yl)C(O)O—; (2-(N,N-dimethylamino)ethyl)(CH$_3$)NC(O)

O—; (2-(N-methyl-N-toluene-4-sulfonylamino)ethyl)(CH$_3$)N—C(O)O—; (2-(morpholin-4-yl)ethyl)(CH$_3$)NC(O)O—; (2-(hydroxy)ethyl)(CH$_3$)NC(O)O—; bis(2-(hydroxy)ethyl)NC(O)O—; (2-(formyloxy)ethyl)(CH$_3$)NC(O)O—; (CH$_3$OC(O)CH$_2$)HNC(O)O—, and 2-[(phenylNHC(O)O-)ethyl-]HNC(O)O—.

When R$^2$ and/or R$^3$ are covalently bonded to a POAM moiety, the linker-POAM group is preferably represented by the formula:

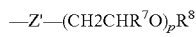

Z' is selected from the group consisting of a covalent bond and a linking group of from 1 to 40 atoms;

R7 is selected from the group consisting of hydrogen and methyl;

R8 is selected from the group consisting of hydrogen, alkyl, substituted alkyl, aryl, substituted aryl, and —CH$_2$CHR$^7$NR$^{10}$R$^{11}$ where R$^7$ is as defined above and R$^{10}$ and R$^{11}$ are independently selected from the group consisting of hydrogen and alkyl; and p is an integer such that the molecular weight of the POAM moiety ranges from about 100 to 100,000.

Preferred —YC(O)V substituents comprising a POAM moiety include the following:

—OC(O)NH(CH$_2$CH$_2$O)$_p$CH$_2$CH$_2$NH$_2$;
—OC(O)NH(CH$_2$CH(CH$_3$)O)$_p$CH$_2$CH(CH$_3$)NH$_2$;
—NHC(O)O(CH$_2$CH$_2$O)$_p$H;
—NHC(O)O(CH$_2$CH(CH$_3$)O)$_p$H;
—NHC(O)O(CH$_2$CH$_2$O)$_p$CH$_3$;
—NHC(O)O(CH$_2$CH(CH$_3$)O)$_p$CH$_3$;
—NHC(O)O(CH$_2$CH$_2$O)$_p$-φ;
—NHC(O)O(CH$_2$CH(CH$_3$)O)$_p$-φ;
—NHC(O)NH(CH$_2$CH$_2$O)$_p$CH$_2$CH$_2$NH$_2$;
—NHC(O)NH(CH$_2$CH(CH$_3$)O)$_p$CH$_2$CH(CH$_3$)NH$_2$;
—OC(O)NH—(1,4)-φ-O—(CH$_2$CH$_2$O)$_p$H;
—OC(O)NH—(1,4)-φ-O—(CH$_2$CH(CH$_3$)O)$_p$H;
—OC(O)NH—(1,4)-φ-O—(CH$_2$CH$_2$O)$_p$CH$_3$;
—OC(O)NH—(1,4)-φ-O—(CH$_2$CH(CH$_3$)O)$_p$CH$_3$;
—OC(O)NH(CH$_2$CH(CH$_3$)O)$_p$CH$_2$CH(CH$_3$)OCH$_3$;
—NHC(O)NH(CH$_2$CH$_2$O)$_p$CH$_3$;
—NHC(O)NH(CH$_2$CH(CH$_3$)O)$_p$CH$_3$;

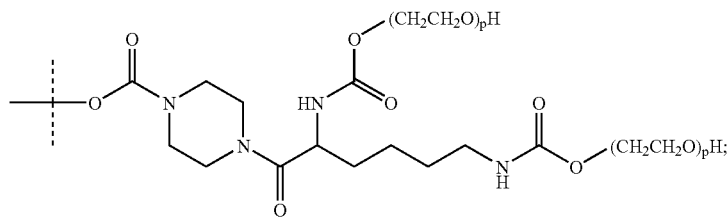

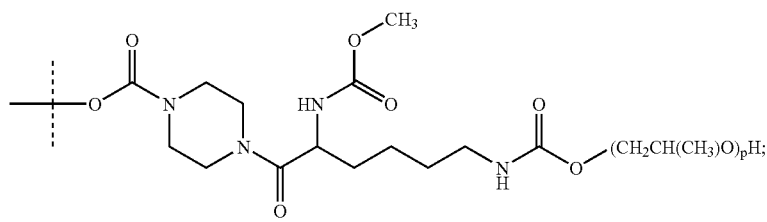

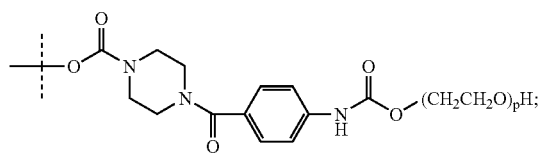
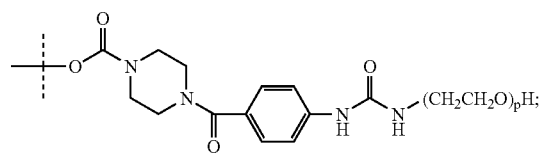

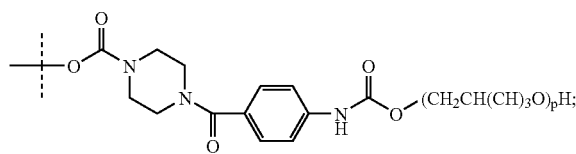
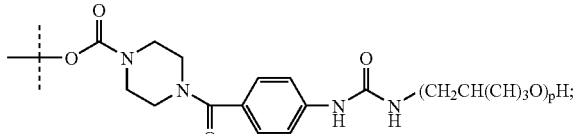

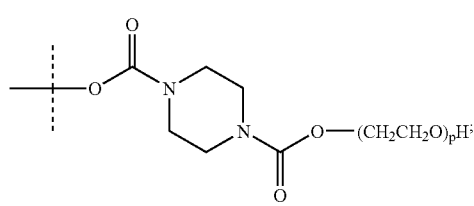
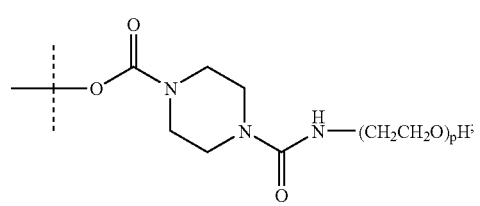

-continued
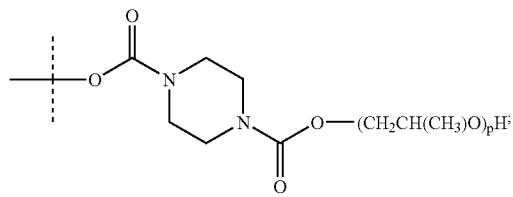
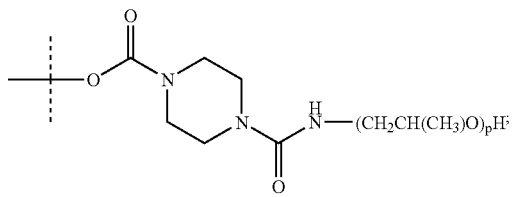
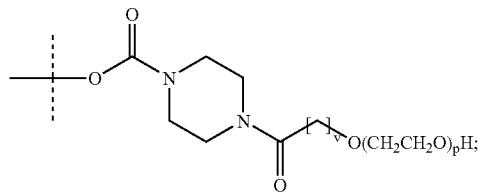
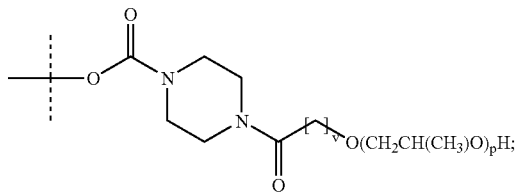
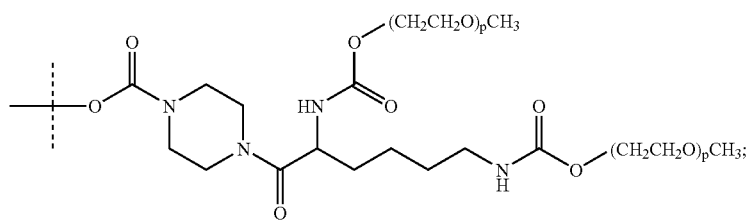
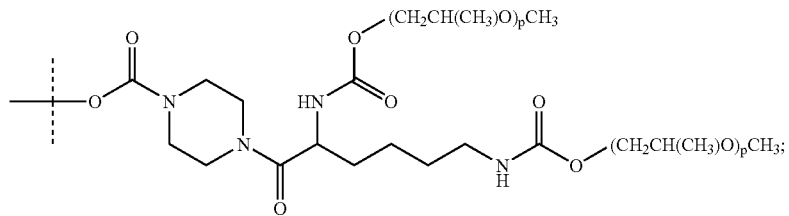
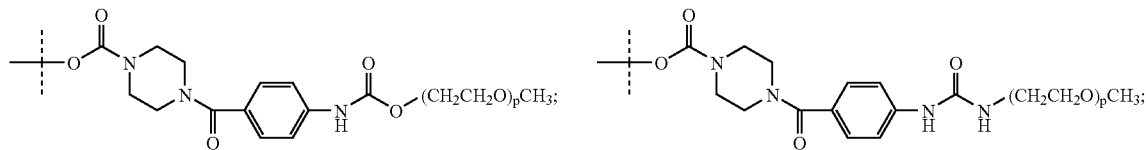
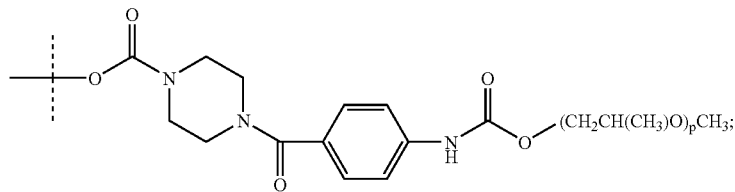
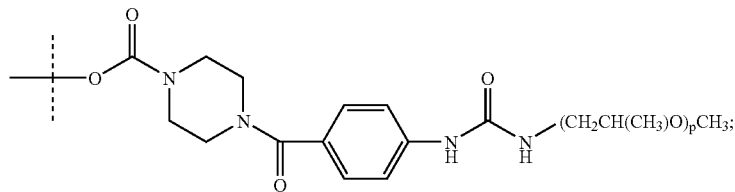
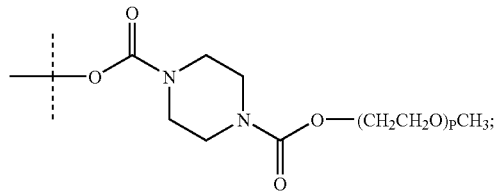
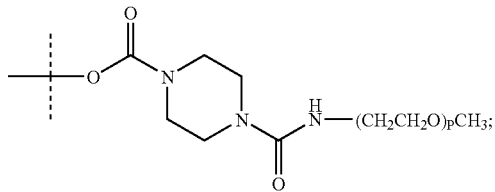

-continued
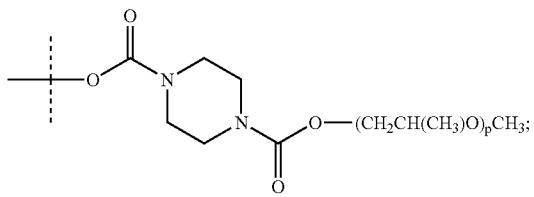
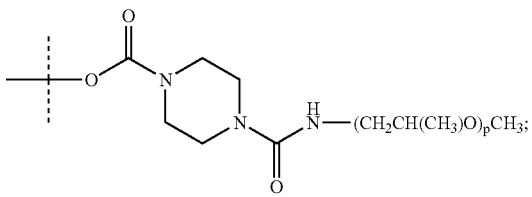
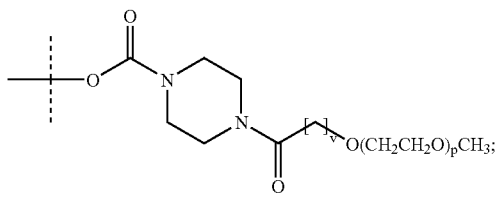
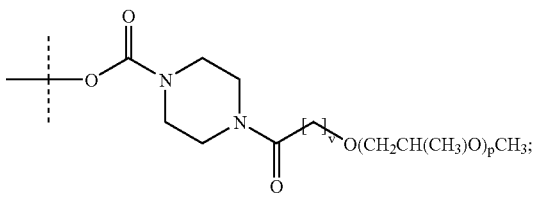
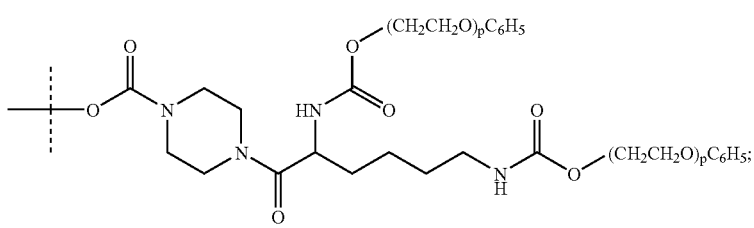
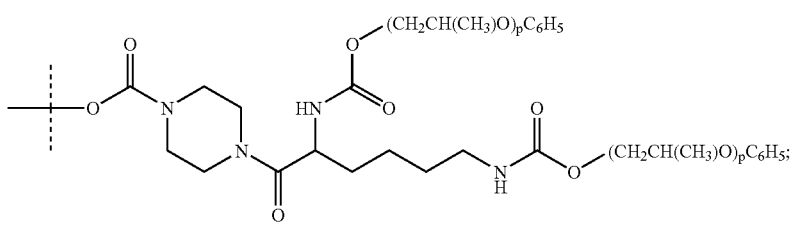
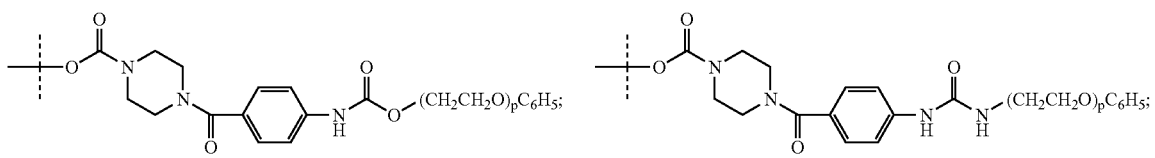
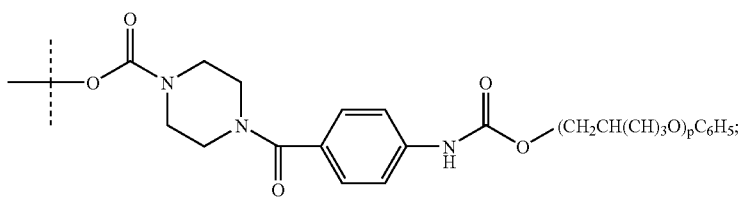
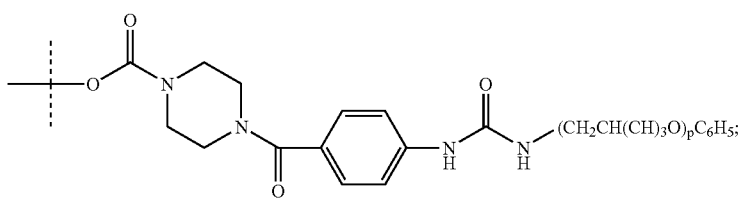
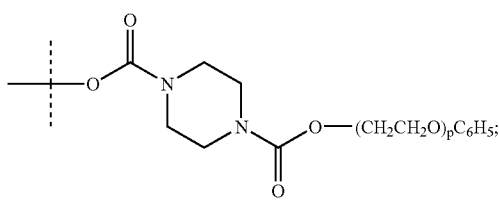
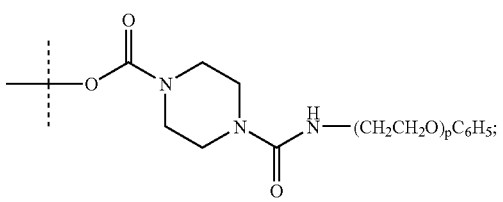

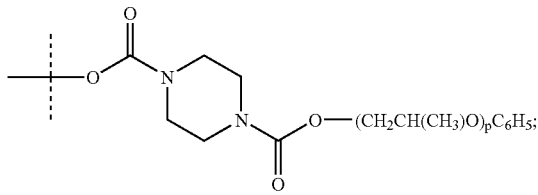
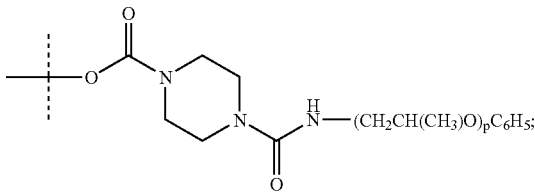
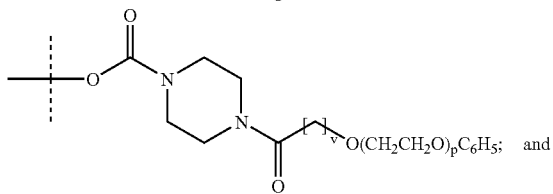
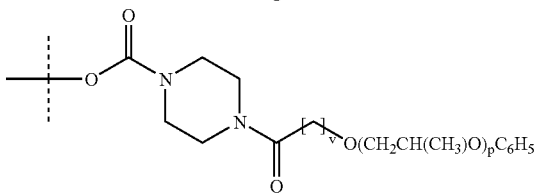
where φ or $C_6H_5$ is phenyl and p is an integer such that the molecular weight of the POAM moiety ranges from about 100 to 100,000 and v is 1 to 5.
Preferred conjugates of this invention include those set forth below:
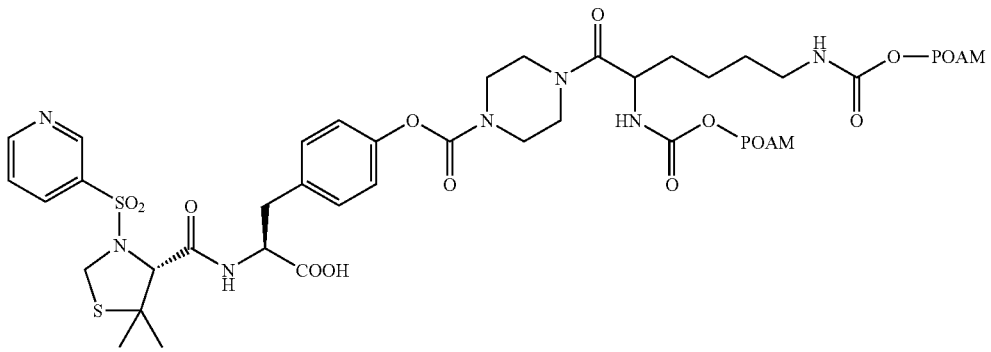
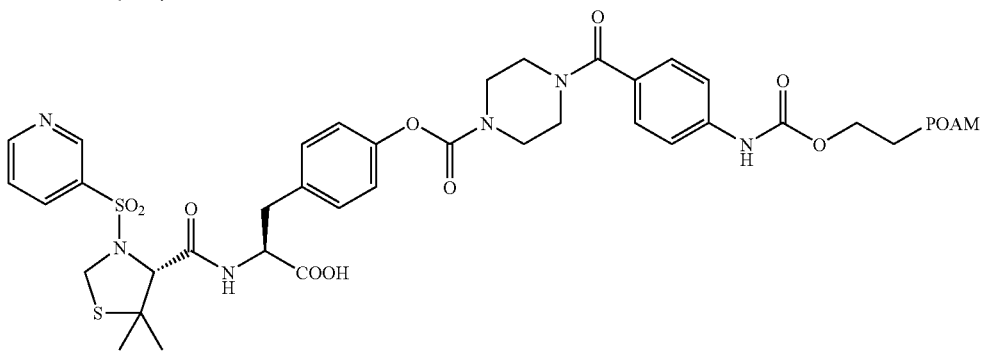
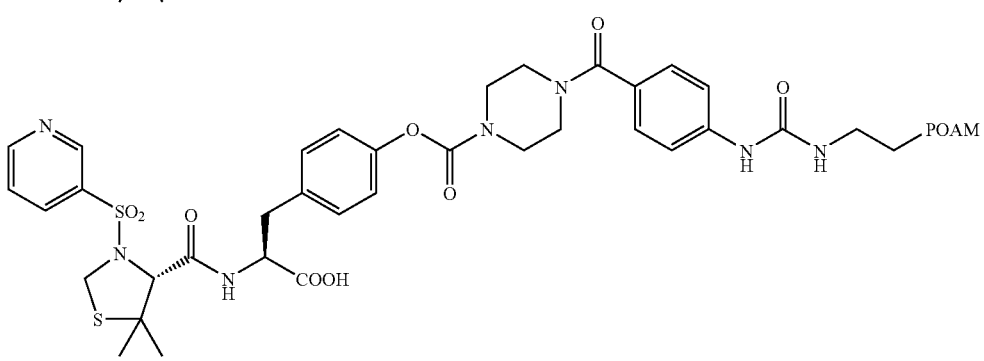

-continued
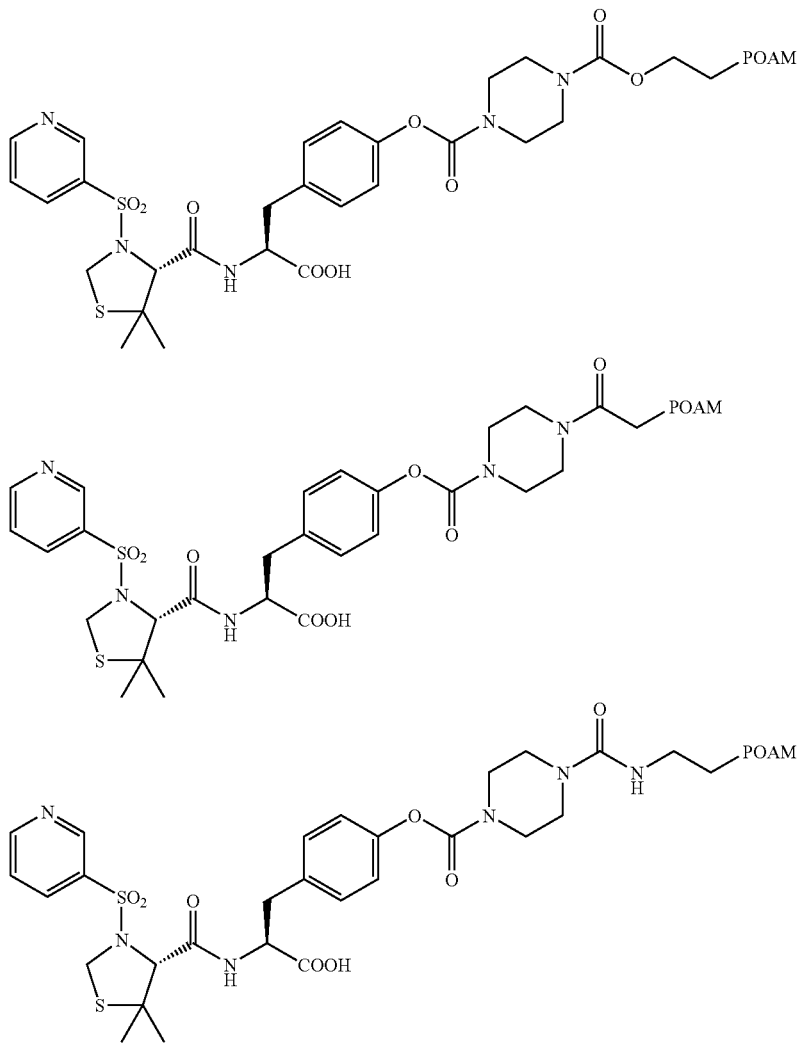
where, in each case, POAM is a methyl capped polyethylene oxide group having a molecular weight (Mw) of approximately 20,000.
Other representative conjugates include:
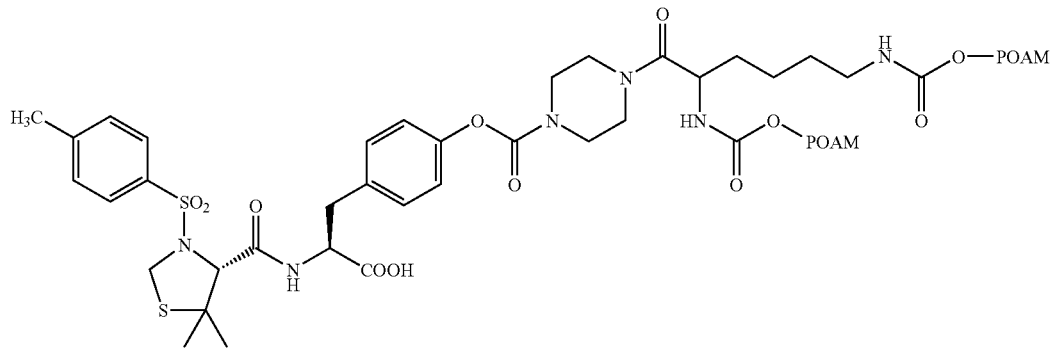

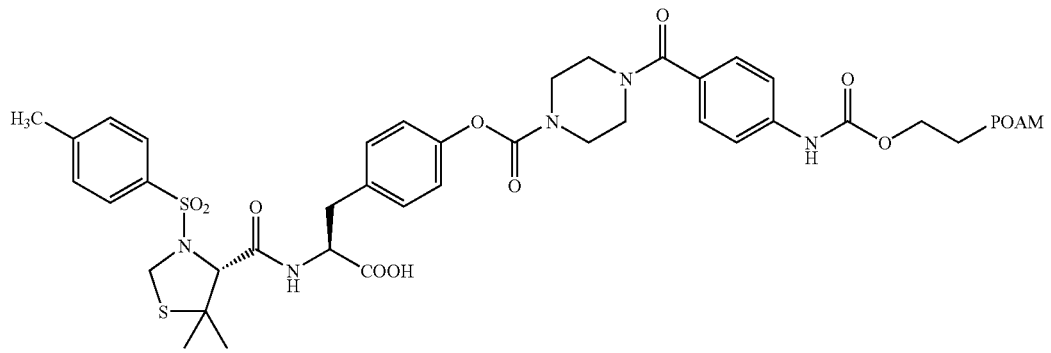
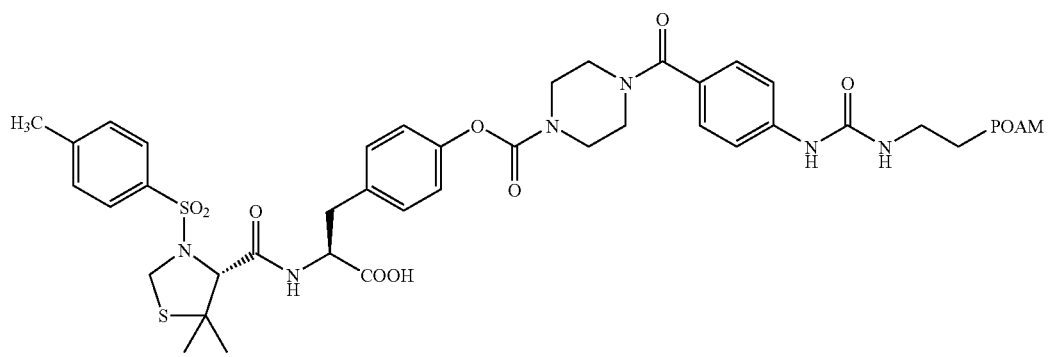
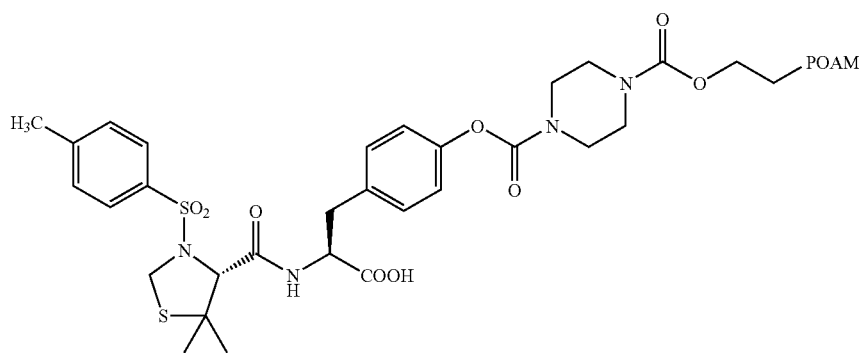
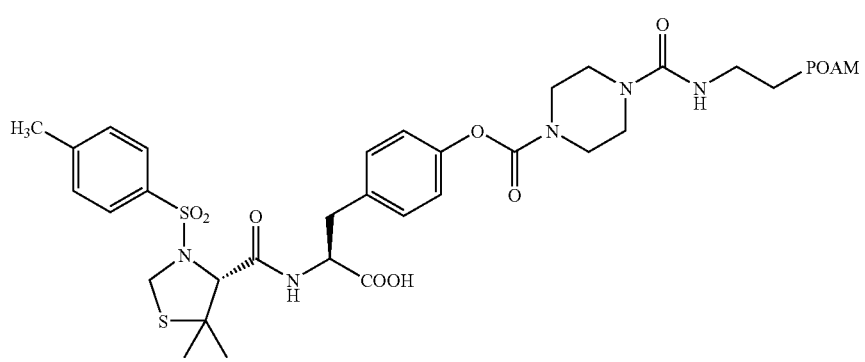

-continued

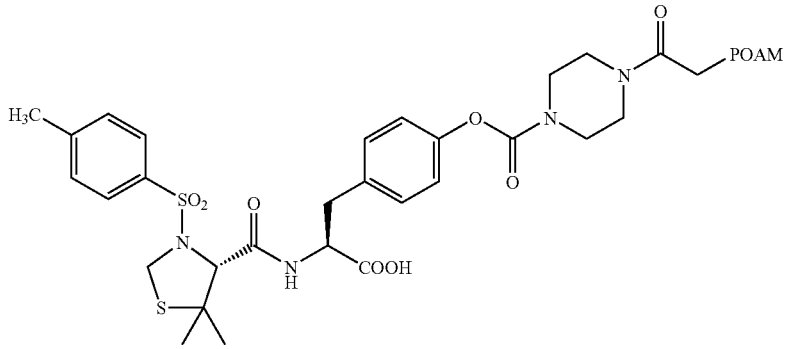

where, in each case, POAM is a methyl capped polyethylene oxide group having a molecular weight (Mw) of approximately 20,000.

Intermediates useful in this invention include those of formula IX:

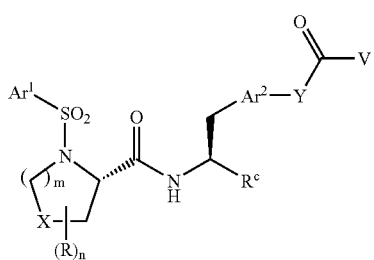

IX wherein

R is a POAM moiety or $R_a$, where $R_a$ is selected from the group consisting of amino, hydroxyl, alkoxy, substituted alkoxy, substituted amino, alkyl and substituted alkyl, -alkyl-O-alkyl, substituted -alkyl-O-alkyl, wherein each $R_a$ is optionally substituted with a POAM moiety covalently bonded to $R_a$ optionally by a linker;

$R^c$ is a carboxyl ester;

$Ar^1$ is selected from the group consisting of aryl, substituted aryl, heteroaryl and substituted heteroaryl, wherein each $Ar^1$ is optionally substituted with a POAM moiety covalently bonded to $Ar^1$ optionally by a linker;

$Ar^2$ is selected from the group consisting of aryl, substituted aryl, heteroaryl and substituted heteroaryl, wherein each $Ar^2$ is optionally substituted with a POAM moiety covalently bonded to $Ar^2$ optionally by a linker;

X is selected from the group consisting of —S—, —SO—, —$SO_2$ and optionally substituted —$CH_2$—;

Y is selected from the group consisting of —O—, —S— and —$NR^1$— wherein $R^1$ is selected from the group consisting of hydrogen and $C_1$-$C_5$ alkyl;

V is selected from the group consisting of
(a) a POAM moiety covalently bonded to —Y(CO)— optionally by a linker; and
(b) $V_a$, which is —$NR^2R^3$ wherein $R^2$ and $R^3$ are independently selected from the group consisting of alkyl and substituted alkyl; and
(c) $V_b$, which is —$NR^2R^3$ and represents a heterocyclic ring or a substituted heterocyclic ring, wherein each of $V_a$ and $V_b$ is optionally substituted with a POAM moiety and where the POAM moiety is covalently bonded to the alkyl, substituted alkyl, heterocyclic rings, or substituted heterocyclic rings within $V_a$ and $V_b$ optionally by a linker;

m is an integer equal to 0, 1 or 2 and when m is 0, then X is optionally substituted —$CH_2$—; and n is an integer equal to 0, 1 or 2;

provided that at least one of R, $Ar^1$, $Ar^2$, V and —$NR^2R^3$ contains a POAM moiety;

further provided that when R is a POAM moiety, n is one and X is not —S—, —SO—, or —$SO_2$—;

and still further provided that the conjugate of formula IX has a molecular weight of no more than 100,000.

DEFINITIONS

As used herein, "alkyl" refers to linear and branched alkyl groups having from 1 to 10 carbon atoms and more preferably 1 to 6 carbon atoms. This term is exemplified by groups such as methyl, t-butyl, n-heptyl, octyl and the like. Inclusion of $C_x$ wherein x is an integer, before the term alkyl denotes the number of carbon atoms in the alkyl chain, where a range is specified, both the smaller integer and the larger are included in the range.

"Substituted alkyl" refers to an alkyl group having from 1 to 5 substituents independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkylene" refers to linear and branched divalent alkylene groups having from 1 to 10 carbon atoms and more preferably 1 to 6 carbon atoms. This term is exemplified by groups such as methylene, 1,6-heptylene, 1,8-octylene and the like which are optionally substituted with from 1 to 5 substituents as defined for substituted alkyl above.

"Alkoxy" refers to the group "alkyl-O-" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O-".

Each alkyl of "alkyl-O-alkyl" is optionally independently substituted with 1 to 5 substituents independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkenyl" refers to alkenyl groups having from 2 to 10 carbon atoms and more preferably 2 to 6 carbon atoms and having at least 1 and preferably from 1-2 sites of alkenyl unsaturation.

"Substituted alkenyl" refers to alkenyl groups having from 1 to 5 substituents independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)NR$^{20}$R$^{20}$ where each R$^{20}$ is independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where each R$^{20}$ is joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Amino" refers to the group —NH$_2$.

"Substituted amino" refers to the group —NR$^{21}$R$^{21}$, where each R$^{21}$ group is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic, and substituted heterocyclic, provided that both R$^{21}$ groups are not hydrogen; or where the R$^{21}$ groups can be joined together with the nitrogen atom to form a heterocyclic or substituted heterocyclic ring.

"Aminoacyl" refers to the groups —NR$^{22}$C(O)alkyl, —NR$^{22}$C(O)substituted alkyl, —NR$^{22}$C(O)cycloalkyl, —NR$^{22}$C(O)substituted cycloalkyl, —NR$^{22}$C(O)alkenyl, —NR$^{22}$C(O)substituted alkenyl, —NR$^{22}$C(O)aryl, —NR$^{22}$C(O)substituted aryl, —NR$^{22}$C(O)heteroaryl, —NR$^{22}$C(O)substituted heteroaryl, —NR$^{22}$C(O)heterocyclic, and —NR$^{22}$C(O)substituted heterocyclic where each R$^{22}$ is hydrogen or alkyl.

"Aminocarbonyloxy" refers to the groups —NR$^{22}$C(O)O-alkyl, —NR$^{22}$C(O)O-substituted alkyl, —NR$^{22}$C(O)O-alkenyl, —NR$^{22}$C(O)O-substituted alkenyl, —NR$^{22}$C(O)O-cycloalkyl, —NR$^{22}$C(O)O-substituted cycloalkyl, —NR$^{22}$C(O)O-aryl, —NR$^{22}$C(O)O-substituted aryl, —NR$^{22}$C(O)O-heteroaryl, —NR$^{22}$C(O)O-substituted heteroaryl, —NR$^{22}$C(O)O-heterocyclic, and —NR$^{22}$C(O)O-substituted heterocyclic where R$^{22}$ is hydrogen or alkyl.

"Oxycarbonylamino" refers to the groups —OC(O)—amino and —OC(O)— substituted amino.

"Aminocarbonylamino" refers to the groups —NR$^{22}$C(O)-amino and —NR$^{22}$C(O)— substituted amino where R$^{22}$ is hydrogen or alkyl.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like) provided that the point of attachment is through an aromatic ring atom. Preferred aryls include phenyl, naphthyl and 5,6,7,8-tetrahydronaphth-2-yl.

"Substituted aryl" refers to aryl groups which are substituted with from 1 to 3 substituents selected from the group consisting of hydroxy, acyl, acylamino, acyloxy, alkyl, substituted alkyl, alkoxy, substituted alkoxy, alkenyl, substituted alkenyl, amino, substituted amino, aminoacyl, aminocarbonyloxy, aminocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, cycloalkyl, substituted cycloalkyl, halo, nitro, heteroaryl, substituted heteroaryl, heterocyclic, substituted heterocyclic, and oxycarbonylamino.

"Aryloxy" refers to the group aryl-O— which includes, by way of example, phenoxy, naphthoxy, and the like.

"Substituted aryloxy" refers to substituted aryl-O— groups.

"Carboxyl" refers to the group —COOH and pharmaceutically acceptable salts thereof.

"Carboxyl esters" refers —C(O)O-alkyl, —C(O)O-substituted alkyl, —C(O)O-alkenyl, —C(O)O-substituted alkenyl, —C(O)O-aryl, —C(O)O-substituted aryl, —C(O)O-cycloalkyl, —C(O)O-substituted cycloalkyl, —C(O)O-heteroaryl —C(O)O-substituted heteroaryl, —C(O)O-heterocyclic, and —C(O)O-substituted heterocyclic.

"Cycloalkyl" refers to cyclic alkyl groups of from 3 to 12 carbon atoms having a single or multiple condensed rings including, by way of example, adamantyl, cyclopropyl, cyclobutyl, cyclopentyl, cyclohexyl, cyclooctyl and the like.

"Substituted cycloalkyl" refers to a cycloalkyl group having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro, chloro or bromo.

"Heteroaryl" refers to an aromatic group of from 2 to 10 carbon atoms and 1 to 4 heteroatoms selected from oxygen, nitrogen and sulfur within the ring or oxides thereof. Such heteroaryl groups can have a single ring (e.g., pyridyl or furyl) or multiple condensed rings wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Preferred heteroaryls include pyridyl, pyrrolyl, indolyl, furyl, pyridazinyl, pyrimidinyl, pyrazinyl, 1-oxo-1,2,5-thiadiazolyl and 1,1-dioxo-1,2,5-thiadiazolyl.

"Substituted heteroaryl" refers to heteroaryl groups which are substituted with from 1 to 3 substituents selected from the group consisting of those defined above for substituted aryl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl, provided that the point of attachment is through a heterocyclic ring atom.

"Substituted heterocyclic" refers to heterocycle groups which are substituted with from 1 to 3 substituents selected from the group consisting of those defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic. The terms "conjugate," and "polymer conjugate" refer to the moiety comprising a VLA-4 antagonist ("compound" or "active compound" as defined below) conjugated to one or more POAM polymers.

The terms "compound" and "active compound" are used to refer to the VLA-4 antagonist portion of a conjugate of the invention or to a VLA-4 antagonist as it exists prior to conjugation to a POAM polymer.

The term "polyoxyalkylene macromolecule" ("POAM" or "POAM moiety") refers to macromolecules that include at least one polyalkylene oxide portion that is optionally covalently bonded to one or more additional polyakylene oxides, wherein the polyalkylene oxides are the same or different. Non-limiting examples include polyethylene glycol (PEG), polypropylene glycol (PPG), polyisopropylene glycol (PIPG), PEG-PEG, PEG-PPG, PPG-PIPG, and the like. In addition, the term "polyoxyalkylene macromolecule" refers to macromolecules wherein the polyalkylene oxide portions are optionally connected to each other by a linker. Illustrative examples are PEG-linker-PEG, PEG-linker-PIPG, and the like. More specific examples include the commercially available poly[di(ethylene glycol)adipates, poly[di(ethylene glycol)phthalate diols, and the like. Other examples are block copolymers of oxyalkylene, polyethylene glycol, polypropylene glycol, and polyoxyethylenated polyol units. Generally, the polyoxyalkylene macromolecules are mono-capped with a substituent preferably selected from alkyl, aryl, substituted alkyl, and substituted aryl.

The terms "Linker", "linking group" or "linker of from 1 to 40 atoms" refer to a group or groups that (1) covalently links a POAM to the active compound and/or (2) covalently link the polyalkylene oxide moieties of a POAM one to another. Within any particular polymer conjugate, the linker connecting the polyalkylene oxide moieties of a POAM together, and the linker bonding a POAM to an active compound may be the same or different (i.e., may have the same or different chemical structures). Representative functional group linkages, of which a linking group may have one or more, are amides, ethers, carbamates, thiocarbamates, ureas, thioureas, amino groups, carbonyl groups, alkoxy groups, etc. The linker may be homogenous or heterogeneous in its atom content (e.g., linkers containing only carbon atoms or linkers containing carbon atoms as well as one or more heteroatoms present on the linker. Preferably, the linker contains 1 to 25 carbon atoms and 0 to 15 heteroatoms selected from oxygen, $NR^{22}$, sulfur, —S(O)— and —S(O)$_2$—, where $R^{22}$ is as defined above. The linker may also be chiral or achiral, linear, branched or cyclic.

Intervening between the functional group linkages or bonds within the linker, the linker may further contain spacer groups including, but not limited to, spacers selected from alkyl, substituted alkyl, aryl, substituted aryl, cycloalkyl, substituted cycloalkyl, heteroaryl, substituted heteroaryl, heterocyclic, substituted heterocyclic, and combinations thereof. The spacer may be homogenous or heterogeneous in its atom content (e.g., spacers containing only carbon atoms or spacers containing carbon atoms as well as one or more heteroatoms present on the spacer. Preferably, the spacer contains 1 to 25 carbon atoms and 0 to 15 heteroatoms selected from oxygen, $NR^{22}$, sulfur, —S(O)— and —S(O)$_2$—, where $R^{22}$ is as defined above. The linker may also be chiral or achiral, linear, branched or cyclic. Preferred linkers are described below.

Non-limiting examples of spacers are straight or branched alkylene chains, phenylene, biphenylene, etc. rings, all of which are capable of carrying one or more than one functional group capable of forming a linkage with the active compound and one or more polyalkylene oxide moieties. One particular example of a polyfunctional linker-spacer group is lysine, which may link any of the active compounds to two polyalkylene oxide moieties via the two amino groups substituted on a $C_4$ alkylene chain. Other non-limiting examples include p-aminobenzoic acid and 3,5-diaminobenzoic acid which have 2 and 3 functional groups respectively available for linkage formation. Other such polyfunctional linkage plus spacer groups can be readily envisaged by one of skill in the art.

The POAM group or groups are covalently attached to the linker using conventional chemical techniques providing for covalent linkage of the POAM to the linker. The linker, in turn, is covalently attached to the active compound. Reaction chemistries resulting in such linkages are well known in the art. Such reaction chemistries involve the use of complementary functional groups on the linker, the active compound and the POAM groups. Preferably, the complementary functional groups on the linker are selected relative to the functional groups available on the POAM group for bonding or which can be introduced onto the POAM group for bonding. Again, such complementary functional groups are well known in the art. For example, reaction between a carboxylic acid of either the linker or the POAM group and a primary or secondary amine of the POAM group or the linker in the presence of suitable, well-known activating agents results in formation of an amide bond covalently linking the POAM group to the linker; reaction between an amine group of either the linker or the POAM group and a sulfonyl halide of the POAM group or the linker results in formation of a sulfonamide bond covalently linking the POAM group to the linker; and reaction between an alcohol or phenol group of either the linker or the POAM group and an alkyl or aryl halide of the POAM group or the linker results in formation of an ether bond covalently linking the POAM group to the linker.

Table I below illustrates numerous complementary reactive groups and the resulting bonds formed by reaction there between.

TABLE I

Representative Complementary Binding Chemistries

| First Reactive Group | Second Reactive Group | Linkage |
|---|---|---|
| hydroxyl | isocyanate | carbamate (urethane) |
| amine | epoxide | β-hydroxyamine |
| sulfonyl halide | amine | sulfonamide |
| carboxyl | amine | amide |
| hydroxyl | alkyl/aryl halide | ether |

Preferred linkers include, by way of example, the following —O—, —NR$^{22}$—, —NR$^{22}$C(O)O—, —OC(O)NR$^{22}$—, —NR$^{22}$C(O)—, —C(O)NR$^{22}$—, —NR$^{22}$C(O)NR$^{22}$—, -alkylene-NR$^{22}$C(O)O—, -alkylene-NR$^{22}$C(O)NR$^{22}$—, -alkylene-OC(O)NR$^{22}$—, -alkylene-NR$^{22}$—, -alkylene-O—, -alkylene-NR$^{22}$C(O)—, -alkylene-C(O)NR$^{22}$—, —NR$^3$C(O)O-alkylene-, —NR$^{22}$C(O)NR$^{22}$-alkylene-, —OC(O)NR$^{22}$-alkylene, —NR$^{22}$-alkylene-, —O-alkylene-, —NR$^{22}$C(O)-alkylene-, —C(O)NR$^{22}$-alkylene-, -alkylene-NR$^{22}$C(O)O-alkylene-, -alkylene-NR$^3$C(O)NR$^{22}$-alkylene-, -alkylene-OC(O)NR$^{22}$-alkylene-, -alkylene-NR$^{22}$-alkylene-, alkylene-O-alkylene-, -alkylene-NR$^{22}$C(O)-alkylene-, —C(O)NR$^{22}$-alkylene-, and

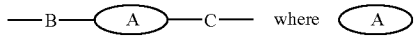

is selected from the group consisting of aryl, substituted aryl, cycloalkyl, substituted cycloalkyl, heteroaryl, substituted heteroaryl, heterocyclic and substituted heterocyclic, and B and C are independently selected from the group consisting of a bond, —O—, CO, —NR$^{22}$—, —NR$^{22}$C(O)O—, —OC(O)NR$^{22}$—, —NR$^{22}$C(O)—, —C(O)NR$^{22}$—, —NR$^{22}$C(O)NR$^{22}$—, -alkylene-NR$^{22}$C(O)O—, -alkylene-NR$^{22}$C(O)NR$^{22}$—, -alkylene-OC(O)NR$^{22}$—, -alkylene-NR$^{22}$—, -alkylene-O—, -alkylene-NR$^{22}$C(O)—, alkylene-C(O)NR$^{22}$—, —NR$^{22}$C(O)O-alkylene-, —NR$^{22}$C(O)NR$^{22}$-alkylene-, —OC(O)NR$^{22}$-alkylene-, —NR$^{22}$-alkylene-, —O-alkylene-, —NR$^{22}$C(O)-alkylene-, —C(O)NR$^{22}$-alkylene-, -alkylene-NR$^{22}$C(O)O-alkylene-, -alkylene-NR$^{22}$C(O)NR$^{22}$-alkylene-, -alkylene-OC(O)NR$^{22}$-alkylene-, -alkylene-NR$^{22}$-alkylene-, alkylene-O-alkylene-, -alkylene-NR$^{22}$C(O)-alkylene-, and —C(O)NR$^{22}$-alkylene-, where R$^{22}$ is as defined above.

Preferred alkylene groups in the above linkers include $C_1$-$C_{15}$ alkylene groups, more preferably $C_1$-$C_6$ alkylene groups, and most preferably $C_1$-$C_3$ alkylene groups. Preferred heterocyclic groups include piperazinyl, piperidinyl, homopiperazinyl, homopiperidinyl, pyrrolidinyl, and imidazolidinyl.

The term "oxyalkylene" refers to —OCH$_2$(CHR$^d$)$_q$— where q is 1, 2, 3, or 4, and R$^d$ at each occurrence is independently H or alkyl. Preferably, q is 1. Polymerized oxyalkylenes are referred to as polyalkylene oxides or polyalkylene glycols, non-limiting examples of which include PEG, poly propylene glycol, polybutylene glycol, polyisopropylene glycol, and the like.

Polyoxyalkylene macromolecules (POAMs) used in the invention preferably have a number average molecular weight of from about 100 to 100,000; preferably from about 1,000 to 50,000; more preferably from about 10,000 to about 40,000. In a particularly preferred embodiment, the molecular weight of the total amount of POAM arising from single or multiple POAM moieties bound in the molecule does not exceed 100,000; more preferably 50,000 and even more preferably 40,000.

In a preferred embodiment, the -[linking group]$_u$-POAM group where u is zero or one can be represented by the formula:

$$-Z'-[(CH_2CHR^7O)_pR^8]_t$$

where Z' is selected from the group consisting of a covalent bond, a linking group of from 1 to 40 atoms, —O—, —S—, —NR$^{22}$—, —C(O)O—, —C(O)NR$^{22}$—, and —C(O)— where R$^{22}$ is selected from the group consisting of hydrogen and alkyl, R$^7$ is selected from the group consisting of hydrogen and methyl;

R$^8$ is selected from the group consisting of hydrogen, alkyl, substituted alkyl, aryl, substituted aryl, —CH$_2$CHR$^7$SR$^7$ and —CH$_2$CHR$^7$NR$^{10}$R$^{11}$ where R$^7$ is as defined above and R$^{10}$ and R$^{11}$ are independently selected from the group consisting of hydrogen and alkyl;

p is an integer such that the molecular weight of the POAM moiety ranges from about 100 to 100,000; and t is an integer from 1 to 5 provided that t is one less than the valency of the linking group and is one when there is no linking group.

When Z' is linking group, multiple POAM groups can be present. For example, if the linking group is trivalent, then 2 POAM groups can be attached and the remaining valency is employed to link to the molecule of formula I. Preferably the number of POAM groups is 1 or 2. In any event, when multiple POAM groups are present, the total aggregate molecular weight of the POAM groups does not exceed 100,000.

"Pharmaceutically acceptable salt" refers to salts which retain the biological effectiveness and properties of the conjugates of this invention and which are not biologically or otherwise undesirable. In many cases, the conjugates of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of non-limiting example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

It is understood that in all substituted groups defined herein, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-(substituted aryl).

Similarly, it is understood that the above definitions are not intended to include impermissible substitution patterns (e.g., methyl substituted with 5 fluoro groups or a hydroxyl group alpha to ethylenic or acetylenic unsaturation). Such impermissible substitution patterns are well known to the skilled artisan.

Compound Preparation

The conjugates of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Second Edition, Wiley, New York, 1991, and references cited therein.

Furthermore, the compounds that form the conjugates of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

The conjugates of this invention contain one or more POAM moieties at one or more of several sites on the active compound of formula I:

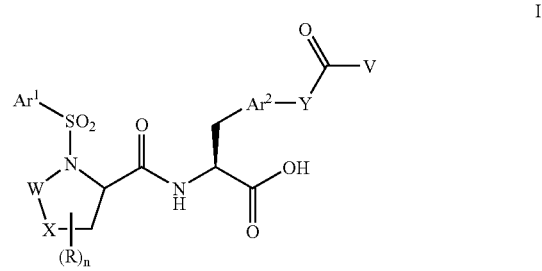

Specifically, the POAM moiety can be incorporated into the $Ar^1$ substituent, the R substituent, the $Ar^2$ substituent and/or in the —YC(O)V substituent wherein the POAM moiety is either directly attached or is attached via a linker. The synthetic protocol for insertion of a POAM moiety at each of these positions is similar and entails reaction of a functional group on the POAM moiety or the linking group covalently bound to the POAM moiety with a complementary functional group on the non-POAM substituted compound.

Initially, non-POAM substituted compounds of formula I are well known in the art and are exemplified in a number of issued patents including, without limitation, U.S. Pat. Nos. 6,489,300 and 6,436,904 both of which are incorporated herein by reference in their entirety. Non-POAM variants of compounds of formula I include those having complementary functional groups or groups derivatizable to complementary functional groups on one or more of the $Ar^1$, R, $Ar^2$ and —YC(O)V moieties. For illustrative purposes, compounds having a complementary functional group (—OH) on the $Ar^2$ moiety (e.g., tyrosine) are recited below as a suitable starting point for addition of a POAM group to the molecule either directly or through a linker.

Such compounds can be prepared by first coupling a heterocyclic amino acid, 1, with an appropriate aryl sulfonyl chloride as illustrated in Scheme 1 below:

Scheme 1

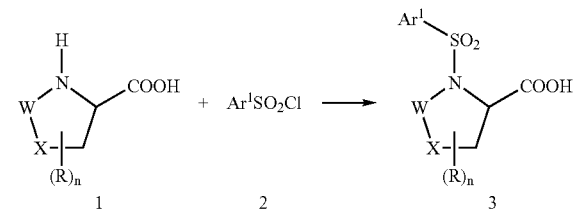

where R, $Ar^1$, X, m and n are as defined above.

Specifically, in Scheme 1 above, heterocyclic amino acid, 1, is combined with a stoichiometric equivalent or excess amount (preferably from about 1.1 to about 2 equivalents) of arylsulfonyl halide, 2, in a suitable inert diluent such as dichloromethane and the like. Generally, the reaction is conducted at a temperature ranging from about −70° C. to about 40° C. until the reaction is substantially complete, which typically occurs within 1 to 24 hours. Preferably, the reaction is conducted in the presence of a suitable base to scavenge the acid generated during the reaction. Suitable bases include, by way of example, tertiary amines, such as triethylamine, diisopropylethylamine, N-methyl-morpholine and the like. Alternatively, the reaction can be conducted under Schotten-Baumann-type conditions using an aqueous alkali solution such as an aqueous solution of sodium hydroxide, an aqueous phosphate solution buffered to pH 7.4, and the like. The resulting product, 3, can be recovered by conventional methods, such as chromatography, filtration, evaporation, crystallization, and the like or, alternatively, used in the next step without purification and/or isolation.

Heterocyclic amino acids, 1, employed in the above reaction are either known compounds or compounds that can be prepared from known compounds by conventional synthetic procedures. Examples of suitable amino acids for use in this reaction include, but are not limited to, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-thiazolidine-4-carboxylic acid, L-(5,5-dimethyl)thiazolidine-4-carboxylic acid, L-thiamorpholine-3-carboxylic acid. If desired, the corresponding carboxylic acid esters of the amino acids, 1, such as the methyl esters, ethyl esters, t-butyl esters, and the like, can be employed in the above reaction with the arylsulfonyl chloride. Subsequent hydrolysis of the ester group to the carboxylic acid using conventional reagents and conditions, i.e., treatment with an alkali metal hydroxide in an inert diluent such as methanol/water, then provides the N-sulfonyl amino acid, 3.

Similarly, the arylsulfonyl chlorides, 2, employed in the above reaction are either known compounds or compounds that can be prepared from known compounds by conventional synthetic procedures. Such compounds are typically prepared from the corresponding sulfonic acid, i.e., from compounds of the formula $Ar^1SO_3H$ where $Ar^1$ is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the arylsulfonyl chlorides, 2, can be prepared from the corresponding thiol compound, i.e., from compounds of the $Ar^1$—SH where $Ar^1$ is as defined herein, by treating the thiol with chlorine ($Cl_2$) and water under conventional reaction conditions.

Alternatively, arylsulfonyl chlorides, 2, employed in the above reaction may be prepared by chlorosulfonylation of substituted benzene or heterocycloalkyl group using Cl—$SO_3H$.

Examples of arylsulfonyl chlorides suitable for use in this invention include, but are not limited to, benzenesulfonyl chloride, 1-naphthalenesulfonyl chloride, 2-naphthalenesulfonyl chloride, p-toluenesulfonyl chloride, o-toluenesulfonyl chloride, 4-acetamidobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethyl-benzenesulfonyl chloride, 4-fluorobenzenesulfonyl chloride, 4-methoxybenzenesulfonyl chloride, 2-methoxycarbonyl-benzenesulfonyl chloride, 4-methylamido-benzenesulfonyl chloride, 4-nitrobenzenesulfonyl chloride, 4-trifluoromethyl-benzenesulfonyl chloride, 4-trifluoromethoxybenzene-sulfonyl chloride, 2,4,6-trimethylbenzenesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazole-sulfonyl chloride, 3-pyridinesulfonyl chloride, 2-pyrimidine-sulfonyl chloride and the like. If desired, a sulfonyl fluoride, sulfonyl bromide or sulfonic acid anhydride may be used in place of the sulfonyl chloride in the above reaction to form the N-sulfonyl amino acid, 3.

The N-arylsulfonyl amino acid, 3, is then coupled to commercially available tyrosine esters as shown in Scheme 2 below:

Scheme 2

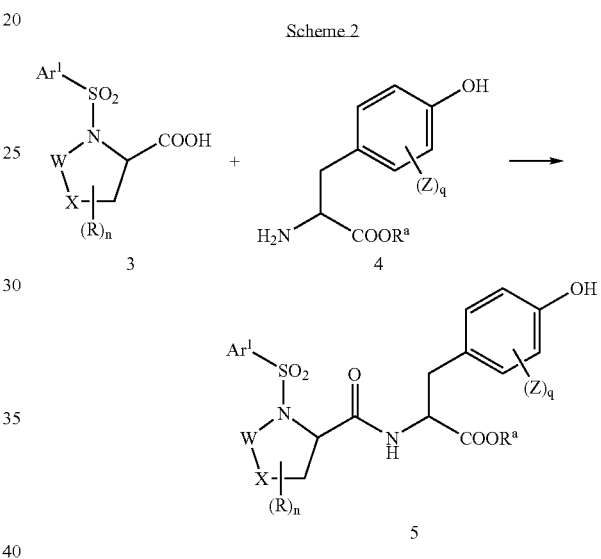

where R, $Ar^1$, X, m and n are as defined above, $R^a$ is hydrogen or alkyl but preferably is an alkyl group such as t-butyl, Z represents optional substitution on the aryl ring and q is zero, one or two.

This coupling reaction is typically conducted using well-known coupling reagents such as carbodiimides, BOP reagent (benzotriazol-1-yloxy-tris(dimethylamino)-phosphonium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in Tetrahedron Letters, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid, 3, with about 1 to about 2 equivalents of the coupling reagent and at least one equivalent, preferably about 1 to about 1.2 equivalents, of tyrosine derivative, 4, in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound 5 is recovered by conventional methods including neutralization, evaporation, extraction, precipitation, chromatography, filtration, and the like.

Alternatively, the N-sulfonyl amino acid, 3, can be converted into an acid halide which is then coupled with compound, 4, to provide compound 5. The acid halide can be prepared by contacting compound 3 with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide of N-sulfonyl amino acid, 3, is then contacted with at least one equivalent, preferably about 1.1 to about 1.5 equivalents, of the tyrosine derivative, 4, in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, compound 5 is recovered by conventional methods including neutralization, evaporation, extraction, precipitation, chromatography, filtration, and the like.

Alternatively, compound 5 can be prepared by first forming a diamino acid derivative and then coupling the diamino acid to the arylsulfonyl halide, 2, as shown in scheme 3 below:

Scheme 3

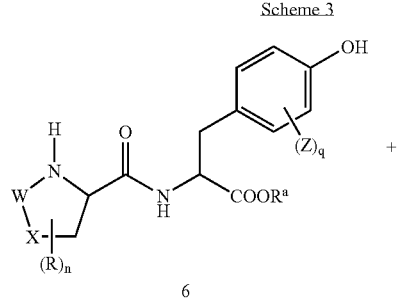

6

-continued

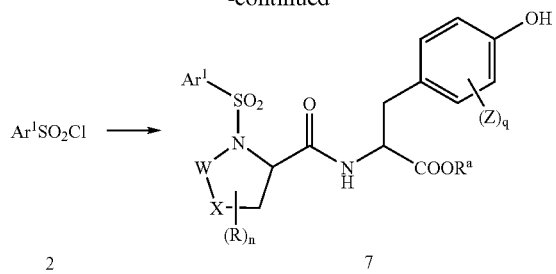

where R, $R^a$, $Ar^1$, X, Z, m, n and q are as defined above.

The diamino acid, 6, can be readily prepared by coupling amino acid, 1, with amino acid, 4, using conventional amino acid coupling techniques and reagents, such carbodiimides, BOP reagent and the like, as described above. Diamino acid, 6, can then be sulfonated using sulfonyl chloride, 2, and using the synthetic procedures described above to provide compound 7.

The tyrosine derivatives, 4, employed in the above reactions are either known compounds or compounds that can be prepared from known compounds by conventional synthetic procedures. For example, tyrosine derivatives, 4, suitable for use in the above reactions include, but are not limited to, L-tyrosine methyl ester, L-tyrosine t-butyl ester, L-3,5-diiodotyrosine methyl ester, L-3-iodotyrosine methyl ester, β-(4-hydroxy-naphth-1-yl)-L-alanine methyl ester, β-(6-hydroxy-naphth-2-yl)-L-alanine methyl ester, and the like. If desired, of course, other esters or amides of the above-described compounds may also be employed.

The N-arylsulfonyl-heterocyclic amino acid-tyrosine derivative, 7, can be used as a starting point to prepare POAM derivatives at the $Ar^2$ group by coupling reactions shown in Schemes 4-14 below which coupling reactions are illustrative only in demonstrating how POAM moieties, such as polythylene glycol derivatives (PEG) can be introduced. In some cases, the POAMmoiety can be directly introduced onto the phenoxy group and, in other cases, the POAMmoiety can be introduced by linkage through a linker moiety.

Specifically, Scheme 4 illustrates the following:

Scheme 4

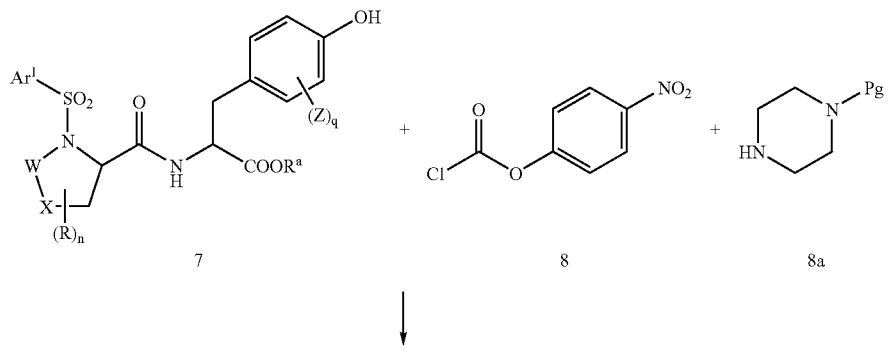

-continued
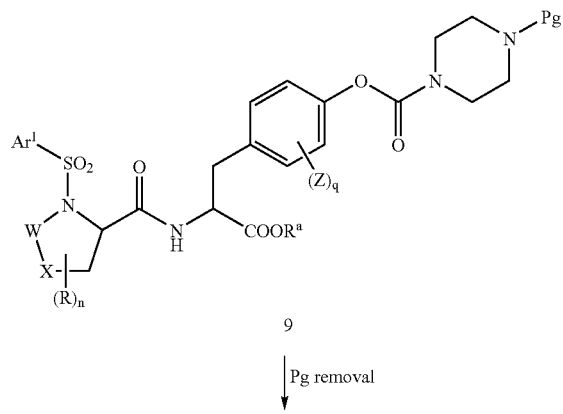
9
↓ Pg removal
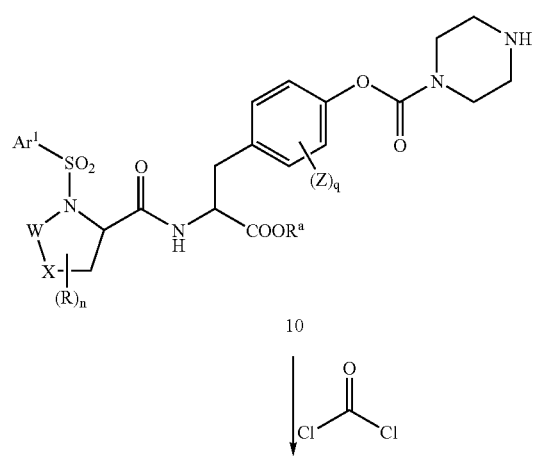
10
↓ Cl—C(O)—Cl
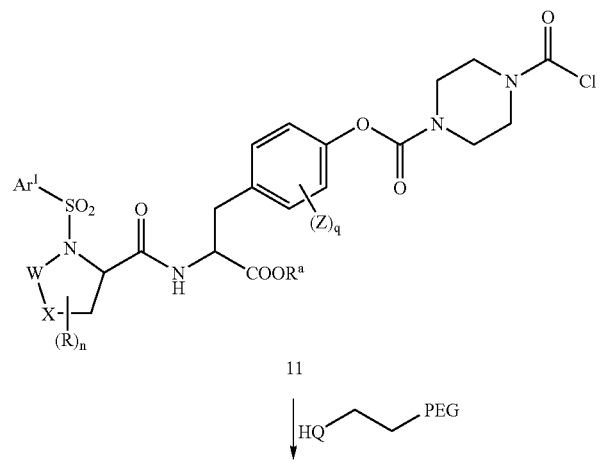
11
↓ HQ—CH2CH2—PEG

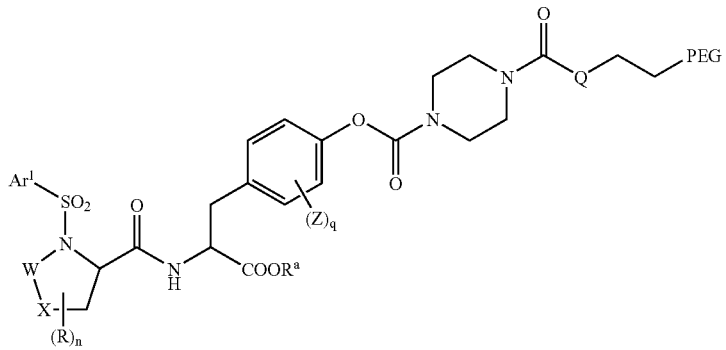

12 wherein $Ar^1$, R, $R^a$, m, n, q, X, and Z are as defined above whereas Q is oxygen, sulfur and NH, Pg is an amine protecting group such as CBZ, Boc, etc, which is preferably orthogonally removeable as compared to the $R^a$ carboxyl protecting group and PEG is preferably a methyl capped poly(oxyethylene) group having a molecular weight of from about 100 to 100,000.

In Scheme 4, the PEG moiety is covalently attached to the N-piperazinylcarbonyltyrosine moiety ($R^2/R^3$ are joined together with the nitrogen atom attached thereto to form a piperazine ring) via a linker entity which constitutes the group:

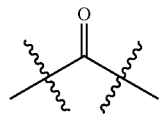

Specifically, in Scheme 4, compound 7, prepared as above, is combined with at least an equivalent and preferably an excess of 4-nitrophenyl chloroformate, 8, in a suitable solvent such as methylene chloride, chloroform and the like and preferably under an inert atmosphere. The reaction is preferably conducted at a temperature of from about −40° to about 0° C. in the presence of a suitable base to scavenge the acid generated. Suitable bases include, by way of example, triethylamine, diisopropylethylamine, and the like. After formation of the intermediate mixed carbonate (not shown), at least an approximately equimolar amount of N-Pg piperazine, 8a, is added to the reaction solution. This reaction is allowed to continue at room temperature for about 1 to 24 hours. Upon completion of the reaction, the compound 9 is recovered by conventional methods including neutralization, evaporation, extraction, precipitation, chromatography, filtration, and the like, or, alternatively, is used in the next reaction without purification and/or isolation.

Conventional removal of the protecting group provides the free piperazine derivative, 10. Removal is accomplished in accordance with the blocking group employed. For example, a trifluoromethylcarbonyl protecting group is readily removed via an aqueous solution of potassium carbonate. Further, suitable protecting groups for various functional groups as well as suitable conditions for protecting and deprotecting particular functional groups are well known in the art. See, for example, T. W. Greene and G. M. Wuts, Protecting Groups in Organic Chemistry, Second Edition, Wiley, New York, 1991, and references cited therein.

The free piperazine derivative, 10, is then converted to the corresponding carbamyl chloride, 11, by reaction in a biphasic reaction mixture of phosgene in toluene (Fluka), dichloromethane and aqueous bicarbonate solution. Subsequent reaction of the carbamyl chloride, 11, with a mono-capped PEG such as commercially available $CH_3(OCH_2CH_2)_pOH$ provides PEG derivative 12. The reaction is conducted in a suitable solvent such as methylene chloride, chloroform, etc. typically in the presence of a catalytic amount of DMAP and a base to scavenge the acid generated during reaction. The reaction is continued until substantially complete which typically occurs within 4 to 24 hours.

When $R^a$ is alkyl, subsequent hydrolysis of the ester derivative provides the free carboxyl group or a salt thereof.

A specific example of this reaction scheme up to formation of the piperazine derivative 10 is illustrated in Scheme 5 below:

Scheme 5

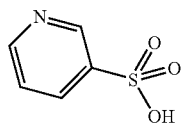

21

$POCl_3, PCl_5$

-continued
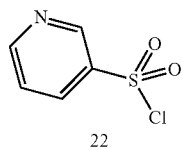
22
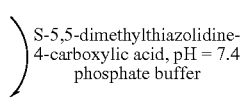
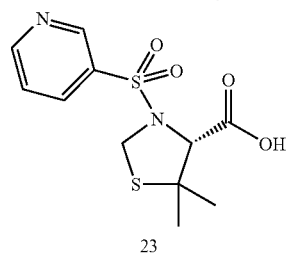
23
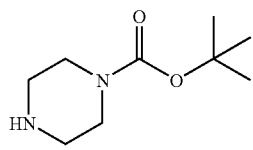
25
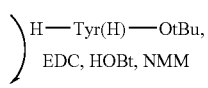     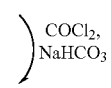
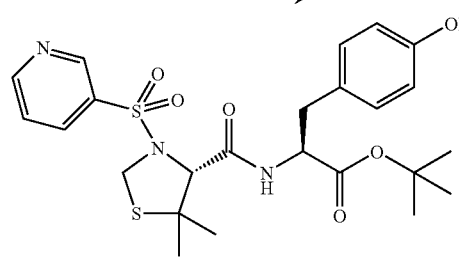
24
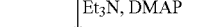
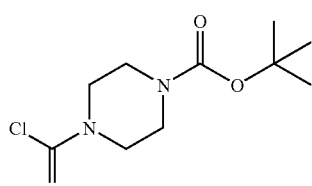
26
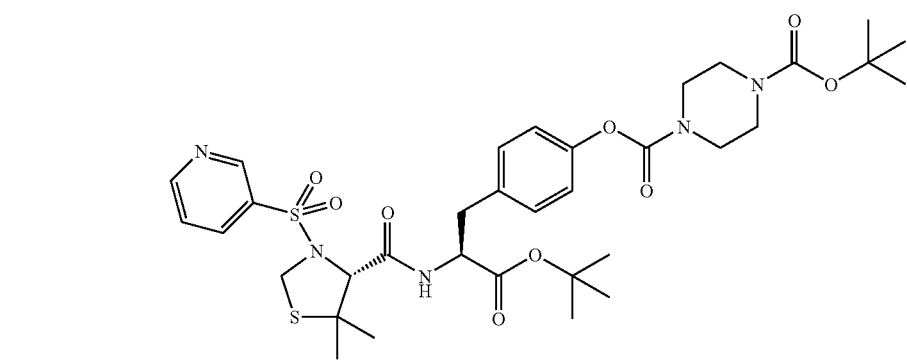
27
TFA
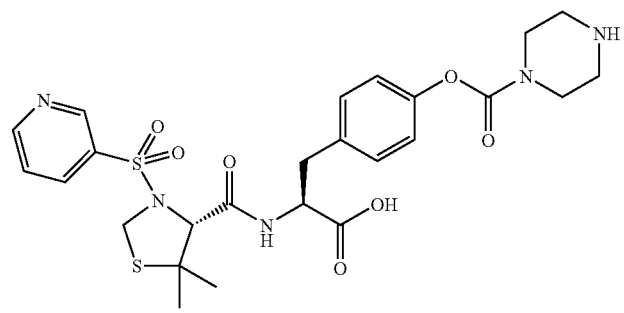
28

Specifically, commercially available 3-pyridinesulfonic acid, 21, is converted under conventional conditions to the corresponding sulfonyl chloride, 22, by contact with POCl$_3$/PCl$_5$ using conditions well known in the art. Coupling of sulfonyl chloride, 22, with commercially available S-5,5-dimethylthiazolidine-4-carboxylic acid, 23, is accomplished under conventional conditions preferably in the presence of a phosphate buffer (pH 7.4) using an excess of sulfonyl chloride. The reaction is preferably conducted at a temperature of from about −10 to 20° C. until the reaction is substantially complete, which typically occurs within 0.5 to 5 hours. The resulting product, 24, can be recovered by conventional methods, such as chromatography, filtration, evaporation, crystallization, and the like or, alternatively, used in the next step without purification and/or isolation.

The N-pyridyl sulfonyl-5,5-dimethylthiazolidine-4-carboxylic acid compound, 23, is next coupled to t-butyl tyrosine using conventional amino acid coupling conditions. Specifically, this coupling reaction is conducted using well known coupling reagents such as 1-(3-dimethylaminopropyl)-3-ethylcarbodiimide (EDC), 1-hydroxy-benzotriazole (HOBt) and N-methylmorpholine to facilitate the coupling reaction.

This coupling reaction is typically conducted by contacting the N-sulfonylamino acid, 23, with about 1 to about 2 equivalents of the coupling reagent and at least one equivalent, preferably about 1 to about 1.2 equivalents, of tyrosine t-butyl ester in an inert diluent, such as dichloromethane, chloroform, acetonitrile, tetrahydrofuran, N,N-dimethylformamide and the like. Generally, this reaction is conducted at a temperature ranging from about 0° C. to about 22° C. for about 12 to about 24 hours. Upon completion of the reaction, the compound 24 is recovered by conventional methods including neutralization, evaporation, extraction, precipitation, chromatography, filtration, and the like or, alternatively, is employed in the next step without purification and/or isolation.

Separately, mono-N-Boc-piperazine, 25, is converted to the corresponding carbamyl chloride, 26, by reaction with phosgene in the manner described above. Upon completion of the reaction, the compound 26 is recovered by conventional methods including neutralization, evaporation, extraction, precipitation, chromatography, filtration, and the like or, alternatively, is employed in the next step without purification and/or isolation.

Coupling of compound 24 with compound 26 to provide for compound 27 proceeds under conventional conditions in an inert diluent such as dichloromethane, with a catalytic amount of DMAP and preferably in the presence of a base to scavenge the acid generate. The reaction is run at a temperature of about −20 to about 22° C. for about 2 to about 24 hours. Upon completion of the reaction, compound 27 is recovered by conventional methods including neutralization, evaporation, extraction, precipitation, chromatography, filtration, and the like or, alternatively, is employed in the next step without purification and/or isolation.

Removal of both the amino Boc protecting group and the t-butyl ester proceeds in the presence of trifluoroacetic acid to provide for compound 28 which can be recovered by conventional methods including neutralization, evaporation, extraction, precipitation, chromatography, filtration, and the like.

Scheme 6 below illustrates the preparation of a piperazine compound orthogonally protected on one of the amine groups relative to the carboxyl protecting group found on the phenylalanine compound such that after coupling, the piperazine protecting group can be removed differentially from that of the carboxyl protecting group. Such orthogonal protection is necessary if subsequent reactions on the resulting compound require a carboxyl-protecting group to avoid undesired side reactions.

Scheme 6

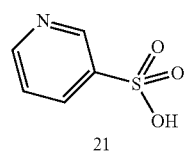
21

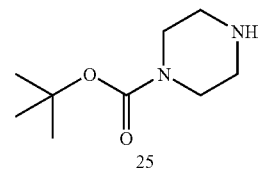
25

) POCl$_3$, PCl$_5$

) TFAA, Et$_3$N

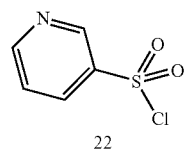
22

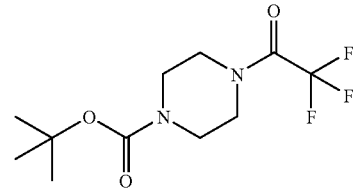
29

) S-5,5-dimethylthiazolidine-4-carboxylic acid, pH = 7.4 phosphate buffer

) HCl gas

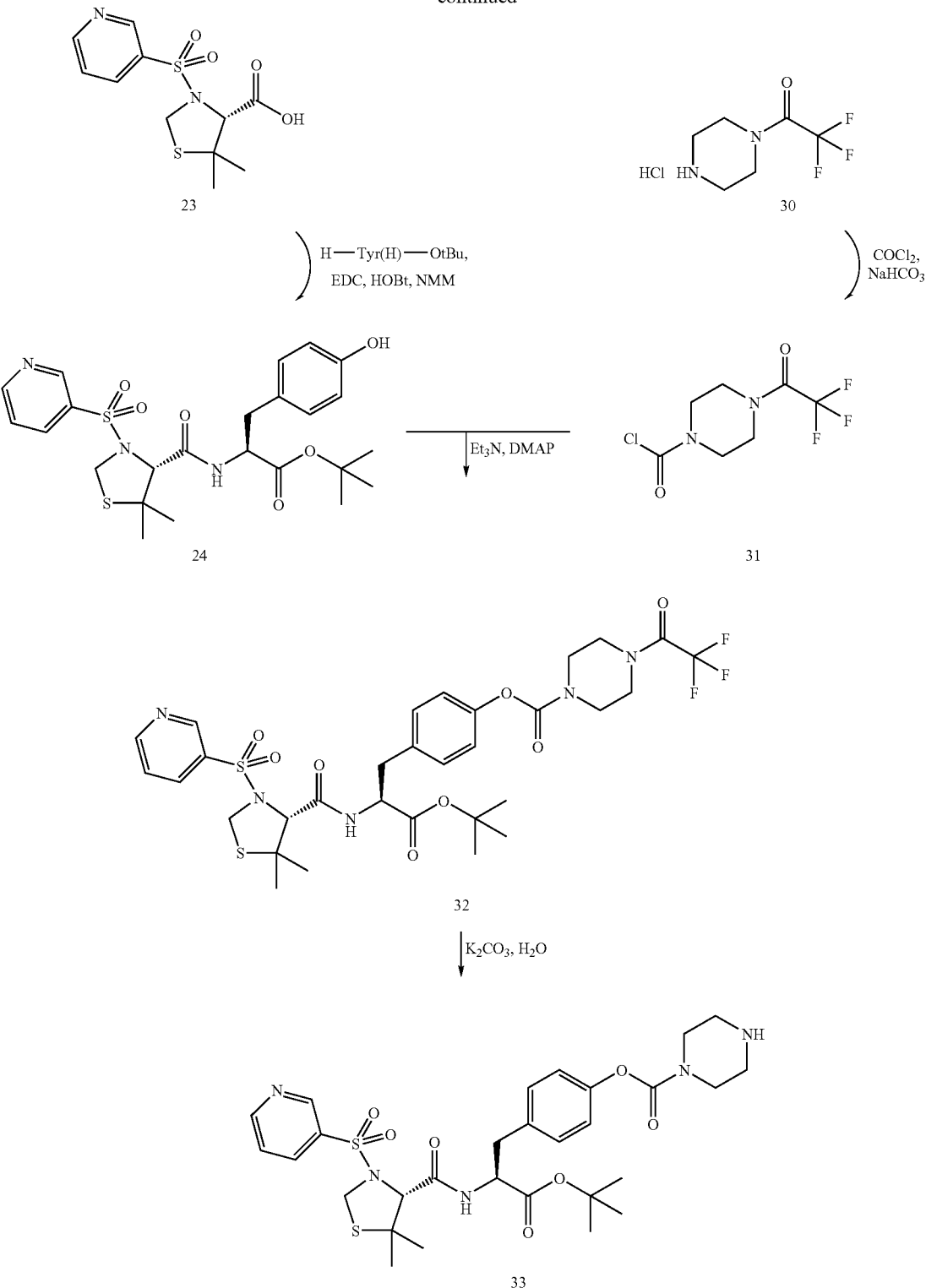

Specifically, in Scheme 6, compound 24 is prepared in the manner described above. N-t-Boc-piperazine, 25, is conventionally converted to N-t-Boc-N'-trifluoromethyl-carbonylpiperazine, 29, by contact with an excess of trifluoroacetic anhydride in the presence of a suitable amine such as triethylamine to scavenge the acid generated during reaction in a suitable solvent such as dichloromethane. Generally, this reaction is conducted at a temperature ranging from about −20° C. to about 22° C. for about 1 to about 24 hours. Upon completion of the reaction, compound 29 can be recovered by conventional methods including neutralization, evaporation, extraction, precipitation, chromatography, filtration, and the like or, alternatively and preferably, is employed in the next step without purification and/or isolation.

In turn, removal of the t-Boc protecting group on the N-t-Boc-N'-trifluoromethylcarbonylpiperazine, 29, proceeds under conventional conditions using gaseous HCl bubbled through an inert solvent such as methylene chloride, EtOAc, EtO$_2$, and the like under ambient conditions to provide for the hydrochloride salt of N'-trifluoromethylcarbonylpiperazine, 30. Generally, this reaction is conducted at a temperature ranging from about −20° C. to about 22° C. for about 0.5 to about 4 hours. Upon completion of the reaction, compound 30 can be recovered by conventional methods including neutralization, evaporation, extraction, precipitation, chromatography, filtration, and the like or, alternatively and preferably, is employed in the next step without purification and/or isolation.

Conversion of N'-trifluoromethylcarbonylpiperazine, 30, to the N-carbamyl chloride derivative, 31, conventionally proceeds by contact with phosgene in the manner described above. Upon completion of the reaction, compound 31 can be recovered by conventional methods including neutralization, evaporation, extraction, precipitation, chromatography, filtration, and the like or, alternatively and preferably, is employed in the next step without purification and/or isolation.

Compounds 31 and 24 are coupled under conditions similar to those described above to provide for compound 32 which is orthogonally protected at the amino moiety of the piperazine group as well as the carboxyl moiety of the phenylalanine group. Selective removal of the trifluoromethylcarbonyl amino protecting group proceeds under conventional conditions using an aqueous solution of potassium carbonate to provide for compound 33.

Scheme 7 below illustrates a first route for derivatization of compound 28 to provide for PEG substitution. In this scheme, the amino moiety of the piperazine group is employed as a complementary functional group to the activated carboxyl group of the lysine derivative to form a covalent amide bond thereby introducing two PEG moieties into the compound through a linker of the formula

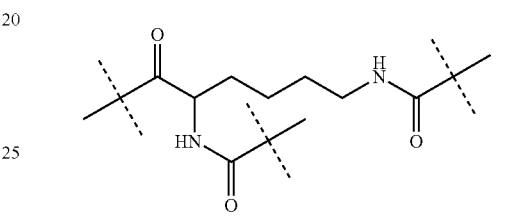

which linker comprises 8 carbon atoms and 5 heteroatoms.

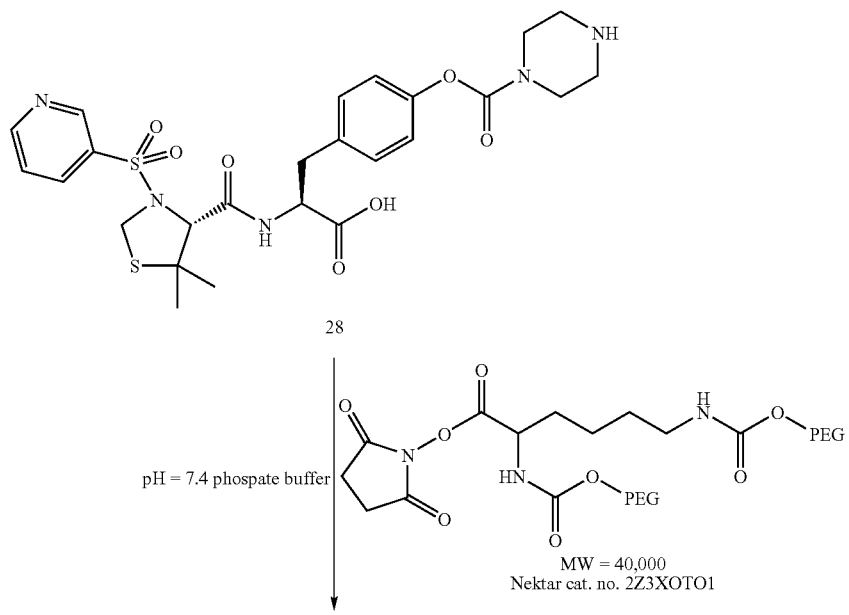

-continued

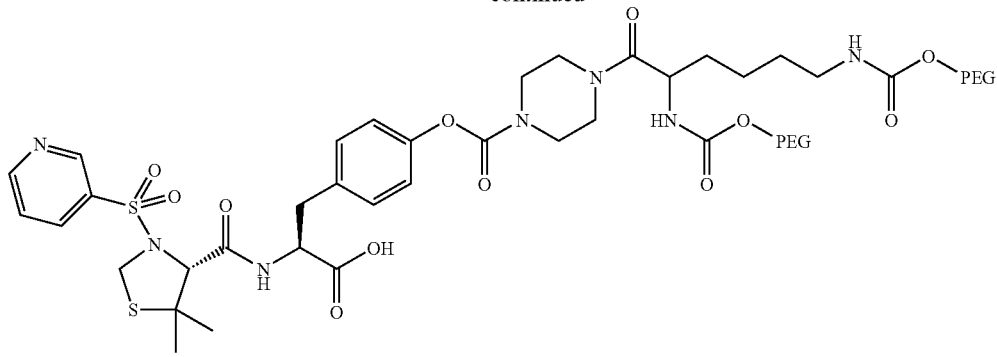

29

Specifically, in Scheme 7, conjugation of an excess of compound 28 (1.1 to 10 eq) with commercially available N-hydroxysuccinimidyl ester of a di-PEG substituted lysine derivative, in the presence of phosphate buffered aqueous solution provides conjugate 29 which is recovered by dialysis. The commercially available N-hydroxy-succinimidyl ester of a di-PEG substituted lysine derivative has a weight average molecular weight of about 40,000 which means that each PEG moiety has a number average molecular weight of about 20,000. The reaction is run at a temperature of about 0 to about 22° C.

Scheme 8 illustrates a second route for derivatization to provide for PEG substitution. In this scheme, the amino moiety of the piperazine group is employed as a complementary functional group to an in situ formed activated carboxyl group of a commercially available carboxyl-PEG which under conventional reactive conditions forms a covalent amide bond thereby introducing a single PEG moiety into the compound. In this embodiment, the carboxyl-PEG is represented by the formula $HOOC(CH_2)_v(OCH_2CH_2)_pOCH_3$ where p and v are as defined above and the resulting linker to the PEG group is represented by $—C(O)(CH_2)_v—$. Carboxylated PEGs can be made by oxidation of the hydroxy terminated PEG moiety using conventional methods and reagents.

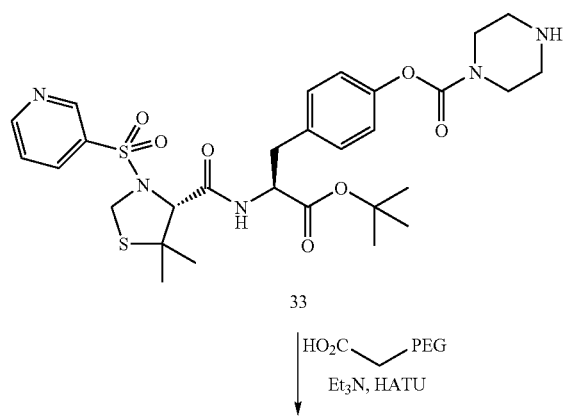

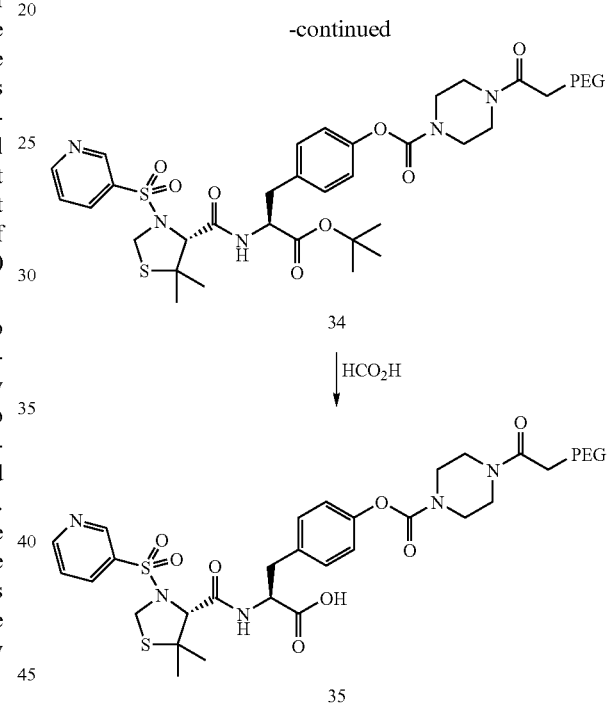

Specifically, in Scheme 8, an excess (1.1 to 10 equiv) of compound 33, prepared as in Scheme 7, is added to at least an equivalent of a commercially available carboxyl-PEG which is converted in situ to an activated ester (not shown) by contact with at least an equivalent and preferably an excess of HATU [O-(7-azabenzotriazol-1-yl)-1,1,3,3,-tetramethyluronium hexafluorophosphate] in the presence of a suitable amine such as triethylamine. Coupling of the carboxyl-PEG to compound 33 preferably proceeds at a temperature of from about 0 to about 22° C. for about 2 to about 24 hours. Upon completion of the reaction, the conjugate 34 is recovered by conventional methods including neutralization, evaporation, extraction, precipitation, chromatography, filtration, and the like or, alternatively, is employed in the next step without purification and/or isolation.

Conventional removal of the t-butyl carboxyl protecting group with an excess of formic acid provides a mono-PEG conjugate of formula I of this invention.

Scheme 9 illustrates a third route for derivatization to provide for PEG substitution. In this scheme, the amino moiety of the piperazine group is employed as a complementary functional group to an in situ formed chloroformate of a commercially available mono-hydroxy-PEG which under conventional reactive conditions forms a covalent carbamate bond thereby introducing a single PEG moiety into the compound. In this embodiment, the mono-hydroxy-PEG is represented by the formula $HOCH_2CH_2(OCH_2CH_2)_pOCH_3$ where p is as defined above and the resulting linker is represented by —C(O)—.

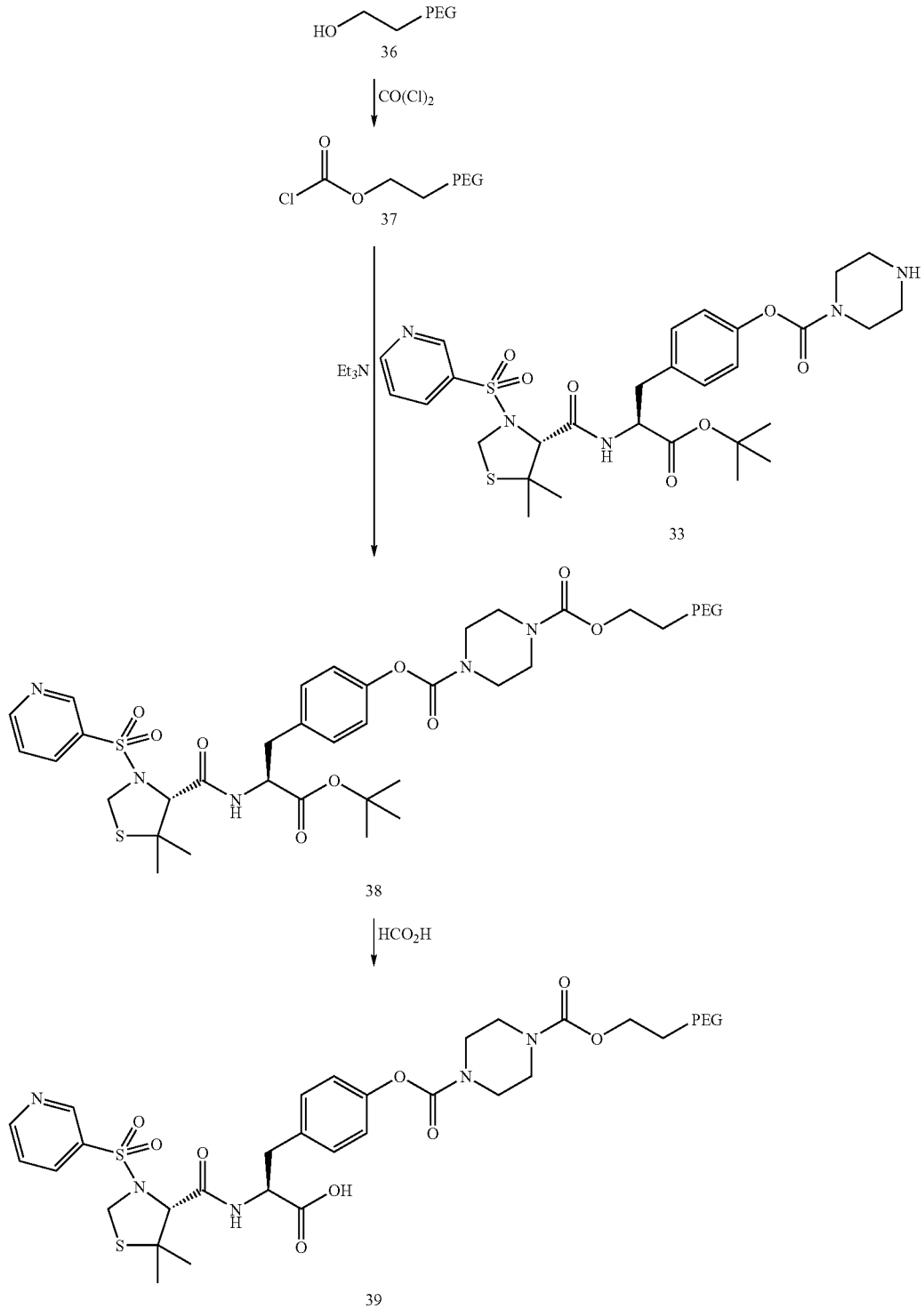

Specifically, in Scheme 9, the hydroxyl group of a commercially available mono-hydroxy PEG, 36, is converted to the corresponding chloroformate, 37, by reaction with phosgene in toluene (Fluka), in dichloromethane. The product is isolated by evaporation and is employed in the next step without further purification.

A slight excess (1.1 to 10 eq) of chloroformate 37 is contacted with compound 33, prepared as above, in the presence of a suitable base such as triethylamine to scavenge the acid generated. Coupling of the chloroformate-PEG to compound 33 preferably proceeds at a temperature of from about 0 to about 22° C. for about 2 to about 4 hours. Upon completion of the reaction, the conjugate 38 is recovered by conventional methods including neutralization, evaporation, extraction, precipitation, chromatography, filtration, and the like or, alternatively, is employed in the next step without purification and/or isolation.

Conventional removal of the t-butyl carboxyl protecting group with an excess of formic acid provides a mono-PEG conjugate, 39, of formula I of this invention.

Scheme 10 illustrates the synthesis of two intermediates useful for subsequent PEG substitution. In this scheme, the amino moiety of the piperazine group is employed as a complementary functional group which is derivatized for subsequent PEG substitution.

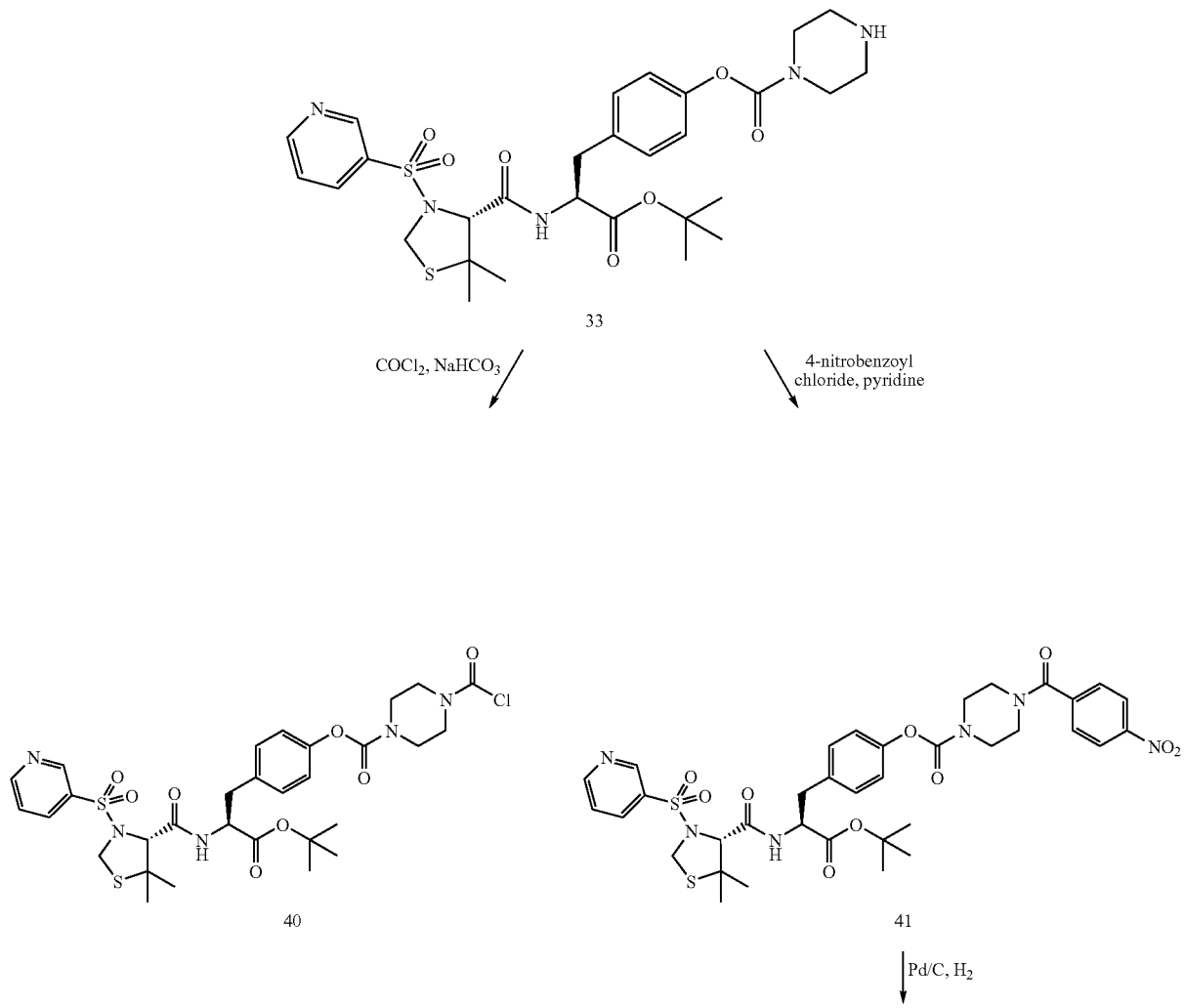

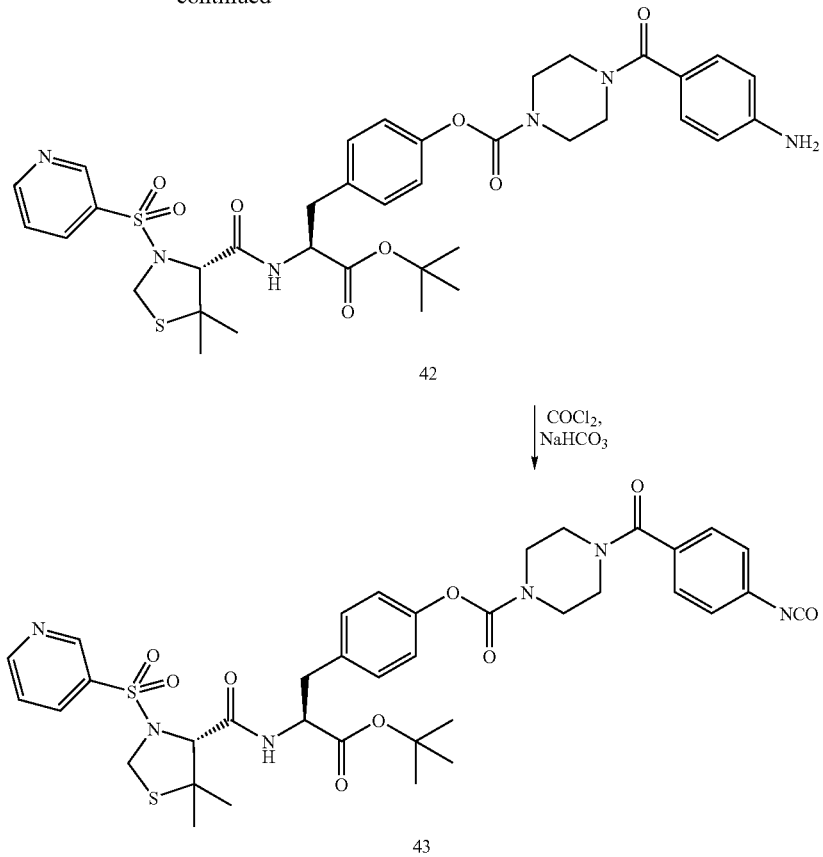

42

43

Specifically, in Scheme 10, conversion of amino moiety of the piperazine group to the corresponding N-carbamyl chloride derivative, 40, proceeds by contact with an excess of phosgene in the presence of a suitable base such as sodium bicarbonate to scavenge the acid generated during reaction. Upon completion of the reaction, compound 40 can be recovered by conventional methods including neutralization, evaporation, extraction, precipitation, chromatography, filtration, and the like or, alternatively and preferably, is employed in the next step (illustrated in Scheme 11) without purification and/or isolation.

Alternatively, the amino moiety of the piperazine group of compound 33 can be converted to the corresponding amide, compound 41, by reaction with at least an equivalent and preferably an excess of 4-nitrobenzoyl chloride in the presence of a base such as pyridine (which can also act as a solvent) to scavenge the acid generated during reaction. The reaction preferably proceeds at a temperature of from about 0 to about 22° C. for about 1 to about 24 hours. Upon completion of the reaction, compound 41 is recovered by conventional methods including neutralization, evaporation, extraction, precipitation, chromatography, filtration, and the like or, alternatively, is employed in the next step without purification and/or isolation.

Subsequent reduction of the para-nitro substituent of the phenyl group provides the amine substituent in compound 42. Reduction is conventionally conducted using palladium/carbon under a hydrogen atmosphere typically at elevated pressures in a suitable diluent such as methanol. The reaction proceeds until substantial completion which typically occurs within about 24 to about 72 hours. During the reaction, additional catalyst is added as required to affect reaction completion. Upon completion of the reaction, the compound 42 is recovered by conventional methods including neutralization, evaporation, extraction, precipitation, chromatography, filtration, and the like or, alternatively, is employed in the next step without purification and/or isolation.

Conversion of the para-amino substituent of the phenyl group of compound 42 to the corresponding isocyanate, 43, occurs by reaction with an excess of phosgene in the presence of a suitable base such as sodium bicarbonate which scavenges the acid generated. The reaction proceeds until substantial completion which typically occurs within about 0.5 to about 5 hours at about 0° C. to about 22° C. Upon completion of the reaction, the compound 43 is recovered by conventional methods including neutralization, evaporation, extraction, precipitation, chromatography, filtration, and the like or, alternatively, is employed in the next step without purification and/or isolation.

Scheme 11 illustrates a fourth route for derivatization to provide for PEG substitution. In this scheme, the carbamyl chloride moiety of the piperazine group of compound 40 is employed as a complementary functional group to form a carbamate or urea bond with a commercially available mono-hydroxy- or mono-amino-PEG which under conventional reactive conditions. In this embodiment, the PEG is represented by the formula $HQCH_2CH_2(OCH_2CH_2)_pOCH_3$ where p and Q are as defined above and the resulting linker is represented by —C(O)—.

Scheme 11

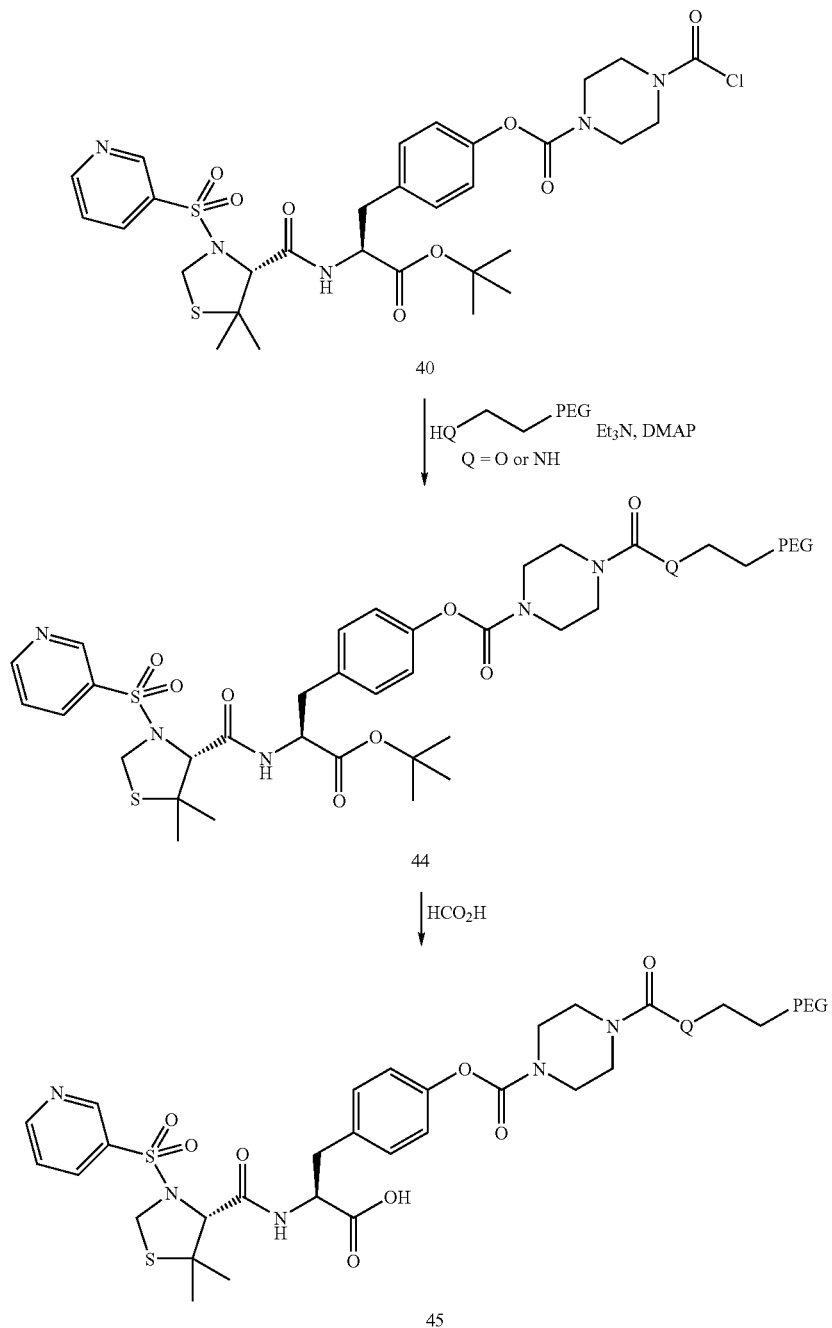

Specifically, in Scheme 11, an excess (1.1 to 10 eq) of carbamyl chloride, 40, is contacted in an inert solvent such as dichloromethane with a suitable mono-hydroxy- or mono-amino-PEG preferably in the presence of a suitable base such as triethylamine and/or catalytic amounts of 4-N,N-dimethylaminopyridine (DMAP). The reaction proceeds until substantial completion which typically occurs within about 4 to about 48 hours. Upon completion of the reaction, the conjugate 44 is recovered by conventional methods including neutralization, evaporation, extraction, precipitation, chromatography, filtration, and the like or, alternatively, is employed in the next step without purification and/or isolation.

When Q is a hydroxyl group, the resulting product contains a carbamate functionality covalently linking the PEG group to the VLA-4 antagonist through a linker represented by —C(O)—. When Q is an amino group, the resulting product contains a urea functionality covalently linking the PEG group to the VLA-4 antagonist through a linker represented by —C(O)—.

Conventional removal of the t-butyl carboxyl protecting group with an excess of formic acid provides a mono-PEG conjugate, 45, of formula Ia of this invention.

Scheme 12 illustrates a fifth route for derivatization to provide for PEG substitution. In this scheme, the isocyanate moiety of the phenyl group of compound 43 is employed as a complementary functional group to form a carbamate or urea bond with a commercially available mono-hydroxy- or mono-amino-PEG which under conventional reactive conditions. In this embodiment, the PEG compound is represented by the formula HQCH$_2$CH$_2$(OCH$_2$CH$_2$)$_p$OCH$_3$ where p and Q are as defined above and the resulting linker is represented by:

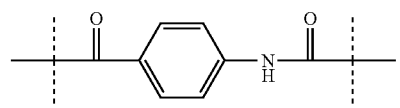

where the linker comprises 8 carbon atoms and 3 heteroatoms.

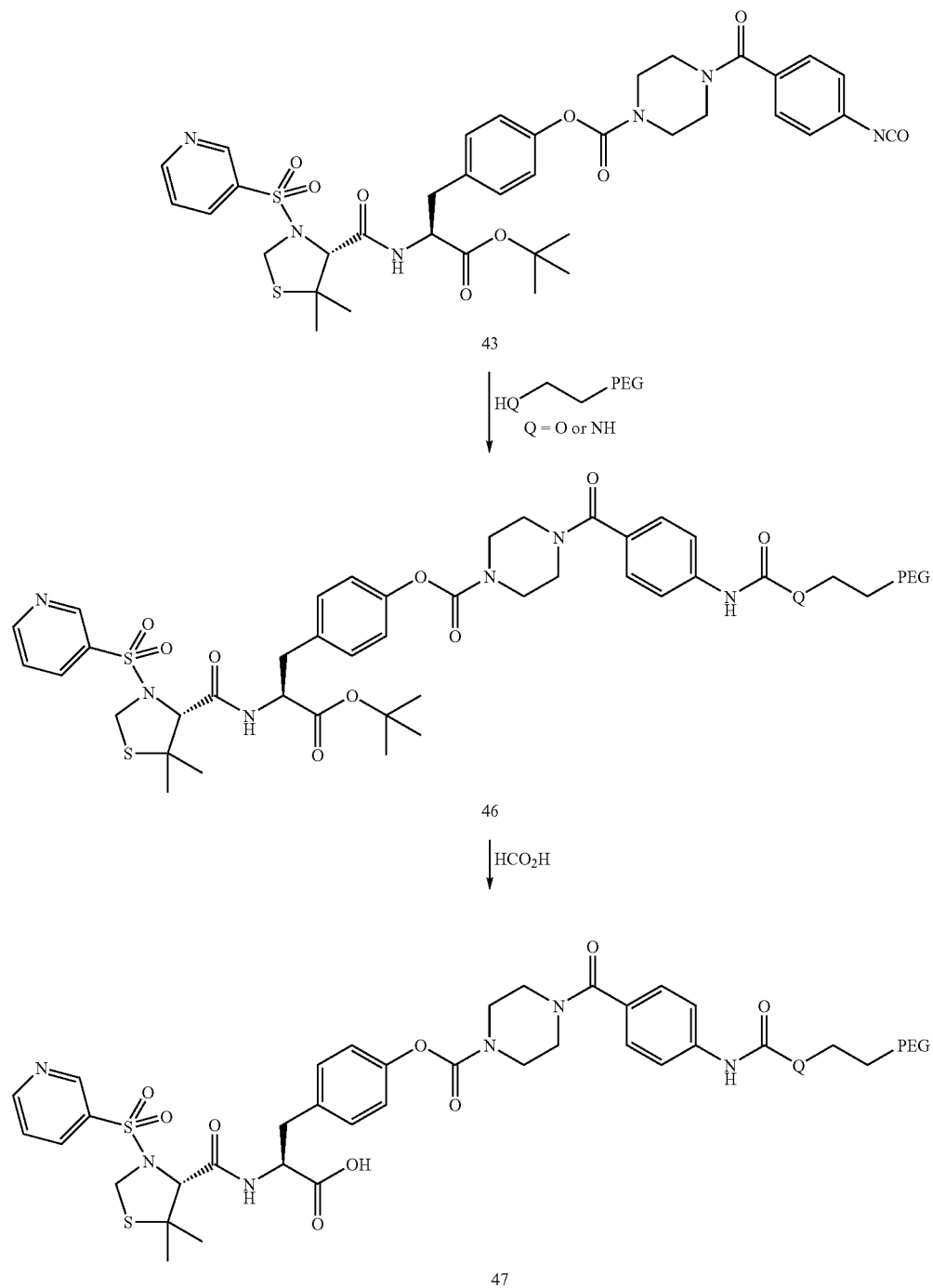

Specifically, in Scheme 12, an excess (1.1 to 10 eq) isocyanate, 43, is contacted with a suitable mono-hydroxy- or mono-amino-PEG in a suitable inert diluent such as dichloromethane or toluene. The reaction is preferably maintained at a temperature of from about 0° to about 105° C. until substantial completion which typically occurs within about 1 to about 24 hours. Upon completion of the reaction, conjugate 46 is recovered by conventional methods including neutralization, evaporation, extraction, precipitation, chromatography, filtration, and the like or, alternatively, is employed in the next step without purification and/or isolation.

When Q is a hydroxyl group, the resulting product contains a carbamate functionality covalently linking the PEG group to the VLA-4 antagonist through a —C(O)-linking group. When Q is an amino group, the resulting product contains a urea functionality covalently linking the PEG group to the VLA-4 antagonist through a —C(O)-linking group.

Conventional removal of the t-butyl carboxyl protecting group with an excess of formic acid provides a mono-PEG conjugate, 47, of formula I of this invention.

In the Schemes above, amine moieties located on other portions of the molecule can be employed in the manner described above to covalently link a PEG group to the molecule. For example, amines located on $Ar^1$, on the heterocyclic amino acid or on $Ar^2$ can be similarly derivatized to provide for PEG substitution. The amine moieties can be included in these substituents during synthesis and appropriately protected as necessary. Alternatively, amine precursors can be employed. For example, as shown in Scheme 10, reduction of a nitro group provides the corresponding amine. Similarly, reduction of a cyano group provides a $H_2NCH_2$— group. Nitro and cyano substituted $Ar^1$ groups are provided in U.S. Pat. No. 6,489,300 as is an amino substituted $Ar^1$ group.

Further, the amino substitution can be incorporated into the heterocyclic amino acid functionality and then derivatized to include a PEG moiety found in formula I as R. For example, the heterocyclic amino acid functionality can be 2-carboxyl piperazine depicted in U.S. Pat. No. 6,489,300. Alternatively, commercially available 3- or 4-hydroxyproline can be oxidized to the corresponding ketone and then reductively aminated with ammonia in the presence of sodium cyanoborohydride to form the corresponding amine moiety. Still further, 4-cyanoproline can be reduced to provide for a substituted alkyl group of the formula —$CH_2NH_2$ which can be derivatized through the amine.

Still further, the amine moiety can be incorporated into the $Ar^2$ functionality. Preferably, the amine moiety is present as an amine precursor such as a nitro or cyano group bound to $Ar^2$.

In the schemes above, the reactions of the amine with a complementary functional group can be reversed such that the carboxyl or hydroxyl group is on the VLA-4 antagonist of formula Ia (without any PEG substituents) and the amine group could be part of the PEG moiety. In such cases, the amine group, preferably terminating the PEG moiety, can be converted to an isocyanate, using phosgene and $Et_3N$, and reacted with the hydroxyl group to form a carbamate as illustrated in Scheme 13 below:

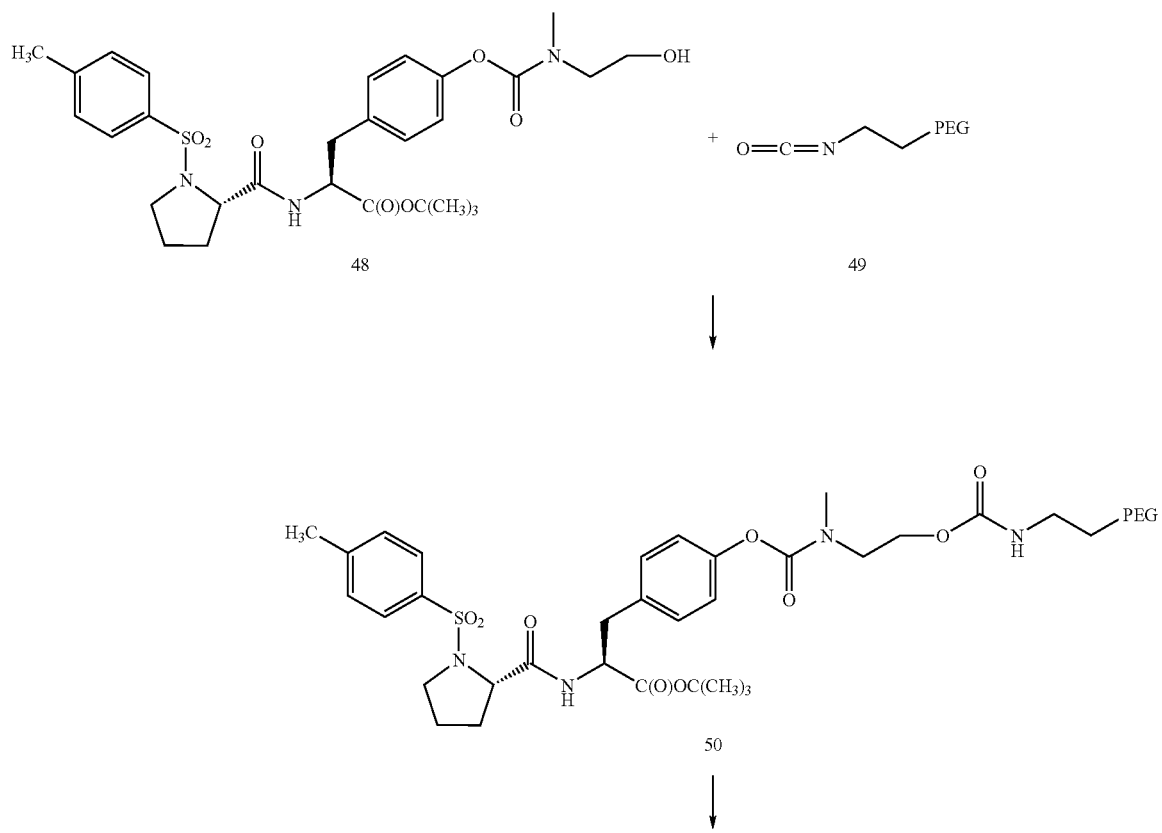

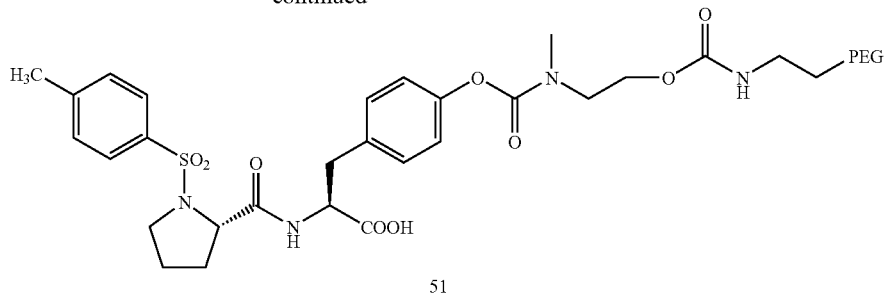

51

Specifically, compound 48 described in U.S. Pat. No. 6,489,300 is contacted with at least an equivalent and preferably an excess of 49 in the manner described above to provide for the corresponding carbamate, 50. Deprotection, as described above, then provides conjugate 51.

Alternatively, in Scheme 13, the hydroxyl functionality can be reacted with phosgene to provide for the chlorocarbonyloxy derivative which reacts with an amine group of a monoamine compound to provide for the carbamate.

Carboxyl functionality, for example on the $Ar^1$ moiety, can be converted to the corresponding amide by reaction with a mono-amino-PEG in the manner described above in Scheme 8.

Scheme 14

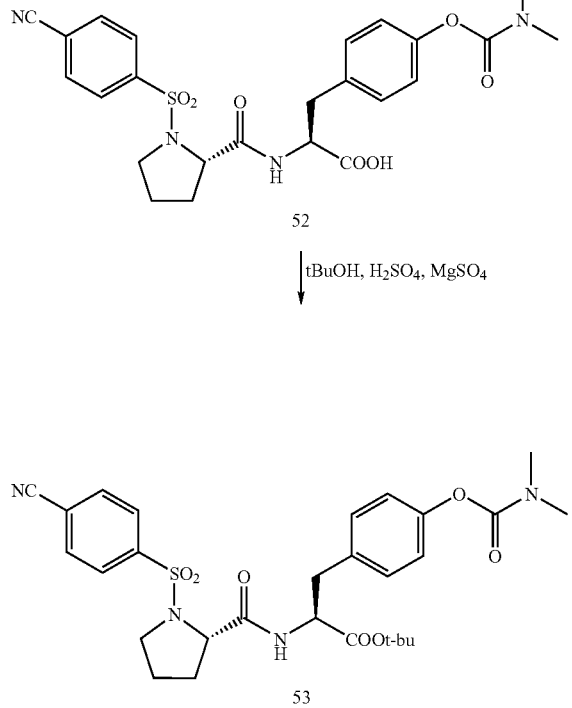

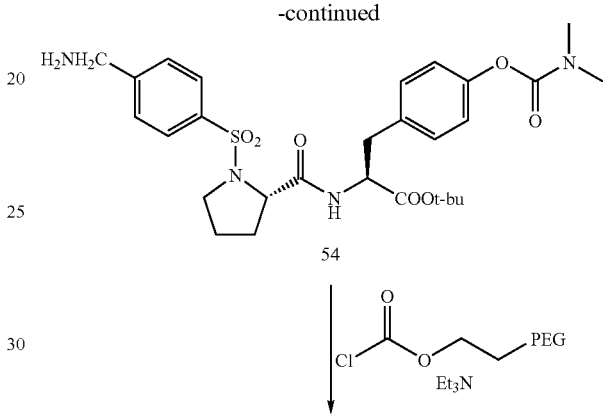

54

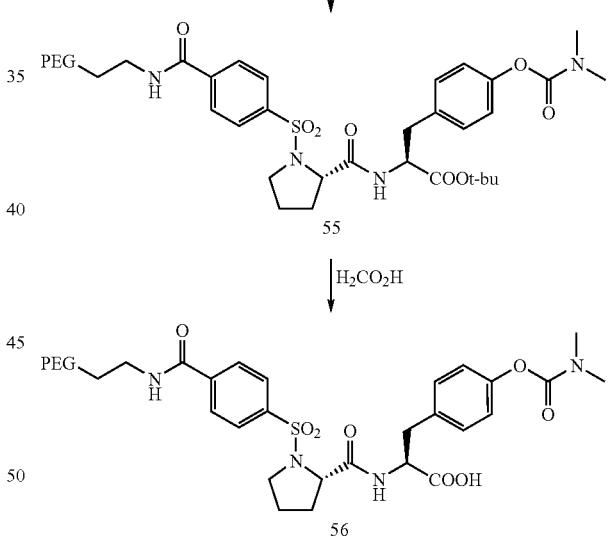

Specifically, in Scheme 14, known compound 52, described in U.S. Pat. No. 6,489,300, is t-butyl protected under convention conditions to provide-4 the cyano compound 53, which is hydrogenated under conventional conditions to provid14e the aminomethyl compound 54. The aminomethyl group is reacted with $Et_3N$ and 1a PEG chloroformate, as illustrated previously in Scheme 9, to provide the carbamate-lin1ked conjugate t-butyl ester 55. Treatment of the t-butyl ester with $HCO_2H$ provides the conj14ugate carboxylic acid 56."

Suitable PEG moieties are commercially available or can be prepared by art recognized procedures. For example, mono-capped linear PEGs with one terminal amine are available in varying molecular weights (e.g., 2 kilodaltons (kDa), 5 kDa, 10 kDa and 20 kDa from Nektar, San Carlos, Calif.). Preferred mono-capped PEGs having one terminal amine group can be represented by the formula H$_2$NCH$_2$CH$_2$(OCH$_2$CH$_2$)$_p$OCH$_3$.

Mono-capped linear PEGs with one terminal alcohol are available in varying molecular weights (e.g., 2 kilodaltons (kDa), 5 kDa, 101 kDa and 20 kDa from Nektar, San Carlos, Calif.). Preferred mono-capped linear PEGs halving one terminal alcohol can be represented by the formula HOCH$_2$CH$_2$(OCH$_2$CH$_2$)$_{p14}$OCH$_3$.

Scheme 15 below illustrates an alternative synthesis of 3-aminopyrrolidinyl derivatives useful as starting materials in this invention for subsequent PEG substitution at the amino group.

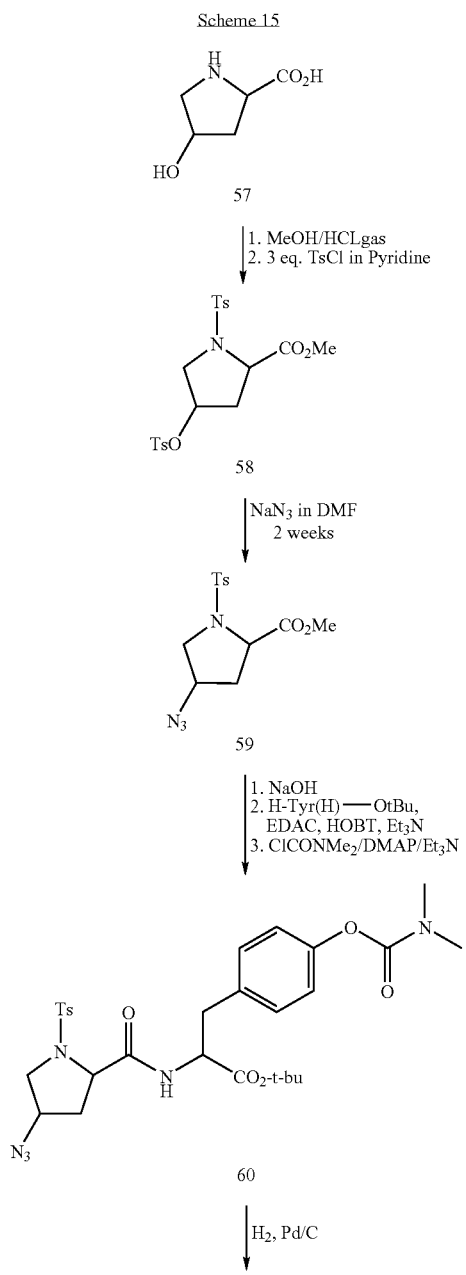

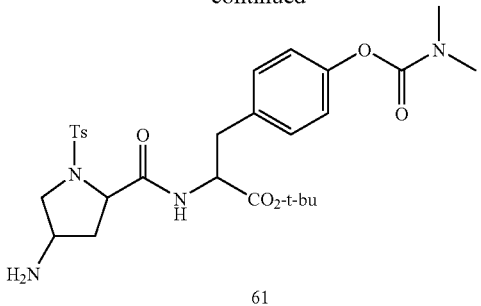

61

Using conventional methods, commercially available cis- or trans-4-hydroxy L-proline, 57, is treated with methanolic hydrogen chloride for several hours at reflux, followed by evaporation, and the so generated methyl ester hydrochloride is treated with excess tosyl chloride in pyridine for two days at room temperature, giving the product, 58. Compound 58 is isolated by neutralizing the pyridine using weak aqueous acid and extracting the product with an organic solvent such as EtOAc. The product 58 may be purified by crystallization, flash chromatography, or more preferably be used in subsequent steps without purification.

Reaction of 58 with a saturated solution of excess sodium azide in DMF at room temperature for 15 days affords compound 59. Compound 59 is isolated by dilution of the reaction mixture with water, followed by extraction with an organic solvent such as EtOAc. The product 59 may be purified by crystallization, flash chromatography, or more preferably be used in subsequent steps without purification.

Compound 59 is treated with sodium hydroxide, in a mixture of water and methanol, thus hydrolyzing the methyl ester and generating a carboxylic acid, which is isolated by acidification and extraction with an organic solvent such as EtOAc. The carboxylic acid is treated with L-tyrosine t-butyl ester [H-Tyr(H)—OtBu], EDAC, HOBt, and Et3N in DMF, generating a dipeptide, which is isolated by dilution with water and extraction with an organic solvent such as EtOAc. The dipeptide is treated with ClCONMe2, Et3N, and DMAP in DCM at reflux for 24 hours, generating the carbamate, 60, which is isolated by dilution with EtOAc, sequential washing with weak aqueous acid and base, and then evaporation. Compound 60 is rigorously purified by flash chromatography.

Finally, compound 61 is prepared by shaking of a solution of 60 in methanol, with a Pd/C catalyst under an atmosphere of hydrogen. The product, 61, is isolated by removal of the catalyst by filtration and evaporation.

Still further, the synthesis of varying mono-capped mono-hydroxy PEGs are described in detail by Campbell, U.S. Pat. No. 4,604,103 which is incorporated herein by reference in its entirety. If a mono-capped mono-amino PEG is preferred, the mono-capped mono-hydroxy PEGs can readily be converted to the corresponding chloride by conventional methods and subsequently converted to an amine by contact with an excess of ammonia.

The PEGs of this invention comprise, for example, the following:

| | |
|---|---|
| HO(alkylene-O)$_p$R$^b$ | mono-capped mono-hydroxy PEG |
| H$_2$N(alkylene-O)$_p$R$^b$ | mono-capped mono-amino PEG | where p and alkylene are as defined herein and $R^b$ is preferably selected from the group consisting of alkyl, substituted alkyl, aryl and substituted aryl.

Pharmaceutical Formulations

When employed as pharmaceuticals, the conjugates of this invention are usually administered in the form of pharmaceutical compositions. These compositions can be administered by a variety of routes including oral, rectal, transdermal, subcutaneous, intravenous, intramuscular, and intranasal. Preferred administration routes include subcutaneous and intravenous. Particularly preferred is subcutaneous. Such compositions are prepared in a manner well known in the pharmaceutical art and comprise at least one active conjugate.

The invention also provides pharmaceutical compositions comprising a conjugate according to the invention, e.g., a conjugate of Formula I, in combination with a separate compound which is an $\alpha_4\beta_7$ inhibitor. Such compositions will also comprise a pharmaceutically acceptable carrier or excipient and may be administered as discussed elsewhere herein.

This invention also includes pharmaceutical compositions which contain, as the active ingredient, one or more of the conjugate of formula I-VIII above associated with pharmaceutically acceptable carriers. In making the compositions of this invention, the active ingredient is usually mixed with an excipient, diluted by an excipient or enclosed within such a carrier which can be in, sterile injectable solutions, and sterile packaged powders. For subcutaneous administration, a simple carrier may comprise a sterile solution of water, Na2HPO4, NaH2PO4, and NaCl, in proportions that provide an isotonic and physiologically acceptable pH, also know as PBS or phosphate-buffered saline. Other options are known to those of skill in the art and include mixed solvent systems that can affect the rate of absorption and total exposure. These options include mixed solvent systems containing glycerin, Polyethylene glycol 400, and cottonseed oil. Also of potential use are ethanol, N,N'-dimethylacetamide, propylene glycol and benzyl alcohol all of which may be used to manipulate permeability enhancement and hypertonicity.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by subcutaneous or intravenous formulation is well known in the pharmaceutical industry. A subcutaneous or intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of conjugates of the present invention as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer:alendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

A useful buffer in the invention is sodium citrate/citric acid in the range of 5 to 50 mg per ml. sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The conjugate is effective over a wide dosage range and is generally administered in a pharmaceutically effective amount. It, will be understood, however, that the amount of the conjugate actually administered will be determined by a physician, in the light of the relevant circumstances, including the condition to be treated, the chosen route of administration, the actual conjugate administered, the age, weight, and response of the individual patient, the severity of the patient's symptoms, and the like.

For preparing solid compositions such as tablets, the principal conjugate is mixed with a pharmaceutical excipient to form a solid preformulation composition containing a homogeneous mixture of a conjugate of the present invention. When referring to these preformulation compositions as homogeneous, it is meant that the conjugate is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

Polymer Conjugates

Compounds of the present invention as formulated and administered are polymer conjugates. Polymer conjugates exhibit benefits over non-conjugated polymers, such as improved solubility and in vivo stability.

As such, single polymer molecule may be employed for conjugation with the compounds of the present invention, although it is also contemplated that more than one polymer molecule can be attached as well. The conjugated compounds of the present invention may find utility in both in vivo as well as non-in vivo applications. Additionally, it will be recognized that the conjugating polymer may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive and enable it to cross-link to a drug molecule and to enhance various properties or characteristics of the overall conjugated material. Accordingly, the polymer may contain any functionality, repeating groups, linkages, or other constitutent structures which do not preclude the efficacy of the conjugated compounds of the present invention composition for its intended purpose.

Illustrative polymers that are usefully employed to achieve these desirable characteristics are described supra, as well as in PCT WO 01/54690 (to Zheng et al.) incorporated by reference herein in its entirety. The polymer may be coupled to the active compound (preferably via a linker moiety) to form stable bonds that are not significantly cleavable by human enzymes. Generally, for a bond to be not 'significantly' cleavable requires that no more than about 20% of the bonds connecting the polymer and the compound to which the polymer is linked, are cleaved within a 24 hour period, as measured by standard techniques in the art including, but not limited to, high pressure liquid chromatography (HPLC).

The conjugates of the present invention are prepared most preferably via a terminal reactive group on the polymer although conjugations can also be branched from non-terminal reactive groups. The polymer with the reactive group(s) is designated herein as "activated polymer". The reactive group selectively reacts with reactive groups on the compounds. The activated polymer(s) is reacted so that attachment may occur at any available functional group on the compounds to which it is being conjugated. Amino, carbon, free carboxylic groups, suitably activated carbonyl groups, hydroxyl, guanidyl, oxidized carbohydrate moieties, amino, carbon and mercapto groups of the compounds (if available) can be used as attachment sites.

Generally, about 1.0 to about 10 moles of activated polymer per mole of the compound, depending on concentration, is employed. The final amount is a balance between maximizing the extent of the reaction while minimizing non-specific modifications of the product and, at the same time, defining chemistries that will maintain optimum activity, while at the same time optimizing the half-life of the compounds. Preferably, at least about 50% of the biological activity of the compounds is retained, and most preferably 100% is retained.

As noted above in the preferred practice of the present invention, polyoxyalkylene macromolecules (POAMs), such as polyalkylene glycol residues of C1-C4 alkyl and polyoxyethylated polyols, are advantageously incorporated in the polymer systems of interest. Thus, the POAM to which the active compound is attached is preferably soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained.

Examples of polyoxyethylated polyols include, but are not limited to, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

Those of ordinary skill in the art will recognize that the foregoing list is merely illustrative and that all polymer materials having the qualities described herein are contemplated. The polymer need not have any particular molecular weight, but it is preferred that the molecular weight be between about 100 and 100,000, more preferably between 10,000 and 40,000. In particular, sizes of 20,000 or more are most effective at preventing loss of the product due to filtration in the kidneys.

By PEG derivative is meant a polyethylene glycol polymer in which one or both of the terminal hydroxyl groups found in polyethylene glycol itself has been modified. Examples of suitable modifications include replacing one or both hydroxyl group(s) with alternative functional groups, which may be protected or unprotected, with low molecular weight ligands, or with another macromolecule or polymer. Modification of the terminal hydroxyl groups in the polyethylene glycol may be achieved by reacting the polyethylene glycol with materials comprising complementary reactive functional groups, including functional groups which are able to undergo a reaction with the hydroxyl groups in polyethylene glycol. The conjugates of this invention may contain one or more polyethylene glycol (PEG) substituents covalently attached thereto by a linking group.

The following formulation examples illustrate the pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the conjugates of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The conjugates of this invention are VLA-4 antagonists as well, some have a partial affinity for alpha4 beta7 integrins, and additionally provide enhanced in vivo retention as compared to the non-conjugated compounds. The improved retention of the conjugate within the body results in lower required dosages of the drug, which in turn results in fewer side effects and reduced likelihood of toxicity. In addition, the drug formulation may be administered less frequently to the patient while achieving a similar or improved therapeutic effect.

The conjugates of this invention have improved inhibition, in vivo, of adhesion of leukocytes to endothelial cells mediated by VLA-4 by competitive binding to VLA-4. Preferably, the conjugates of this invention can be used, e.g., by infusion, or by subcutaneous or oral administration, for the treatment of diseases mediated by VLA-4 or leucocyte adhesion. The conjugates of the invention can be used to treat a variety of inflammatory brain disorders, especially central nervous system disorders in which the endothelium/leukocyte adhesion mechanism results in destruction to otherwise healthy brain tissue. Thus, the conjugates of the invention can be used for, e.g., the treatment of experimental autoimmune encephalomyelitis (EAE), multiple sclerosis (MS), meningitis, and encephalitis.

The conjugates of the invention can also be used to treat disorders and diseases due to tissue damage in other organ systems, i.e., where tissue damage also occurs via an adhesion mechanism resulting in migration or activation of leukocytes. Examples of such diseases in mammalian patients are inflammatory diseases such as asthma, Alzheimer's disease, atherosclerosis, AIDS dementia, diabetes (including acute juvenile onset diabetes), inflammatory bowel disease (including ulcerative colitis and Crohn's disease), rheumatoid arthritis, tissue transplantation rejection, tumor metastasis, stroke, and other cerebral traumas, nephritis, retinitis, atopic dermatitis, psoriasis, myocardial ischemia and acute leukocyte-mediated lung injury such as that which occurs in adult respiratory distress syndrome.

Still other disease conditions which may be treated using conjugates of the invention include erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

The invention also provides methods for treating a disease state caused or exacerbated at least in part by alpha 4 integrin-mediated leukocyte binding in a patient, which methods comprise co-administration of an effective amount of a conjugate of the invention, e.g., a conjugate of Formula I, and an effective amount of a separate compound which is an $\alpha_4\beta_7$ inhibitor. The co-administration can be carried out simultaneously or sequentially. For example, administration of the conjugate of the invention can precede administration of the $\alpha_4\beta_7$ inhibitor by minutes or hours. Alternatively, the $\alpha_4\beta_7$ inhibitor can be administered prior to the conjugate of the invention.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha4$ integrins.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, Immunology (3d ed., Raven Press, 1993).

Another indication for the conjugates of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. $CD8^+$ cells, CD4 cells and monocytes are all involved in the rejection of transplant tissues. Conjugates of this invention which bind to alpha-4 integrin are useful, inter alia, to block alloantigen-induced immune responses in the donee thereby preventing such cells from participating in the destruction of the transplanted tissue or organ. See, e.g., Paul et al., Transplant International 9, 420-425 (1996); Georczynski et al., Immunology 87, 573-580 (1996); Georcyznski et al., Transplant. Immunol. 3, 55-61 (1995); Yang et al., Transplantation 60, 71-76 (1995); Anderson et al., APMIS 102, 23-27 (1994).

A related use for conjugates of this invention which bind to VLA-4 is in modulating the immune response involved in "graft versus host" disease (GVHD). See e.g., Schlegel et al., J. Immunol. 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

The formulations of the present invention are especially useful in the treatment of multiple sclerosis, rheumatoid arthritis and asthma.

A further use of the conjugates of this invention is inhibiting tumor metastasis. Several tumor cells have been reported to express VLA-4 and compounds which bind VLA-4 block adhesion of such cells to endothelial cells. Steinback et al., Urol. Res. 23, 175-83 (1995); Orosz et al., Int. J. Cancer 60, 867-71 (1995); Freedman et al., Leuk. Lymphoma 13, 47-52 (1994); Okahara et al., Cancer Res. 54, 3233-6 (1994).

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

A further use of the conjugates of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

The therapeutic dosage of the conjugates of the present invention will vary according to, for example, the particular use for which the treatment is made, the manner of administration of the conjugate, the health and condition of the patient, and the judgment of the prescribing physician. For example, for intravenous administration, the dose will typically be in the range of about 20 µg to about 2000 µg per kilogram body weight, preferably about 20 µg to about 500 µg, more preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

Conjugates of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, conjugates of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187-2191. Compounds that bind $\alpha_e\beta_7$ integrin are also useful for the treatment of systemic lupus erythematosus (see, for example, M. Pang et al., *Arthritis Rheum.* 1998, 41(8), 1456-1463); Crohn's disease, ulcerative colitis and inflammatory bowel disease (IBD) (see, for example, D. Elewaut et al., *Scand J. Gastroenterol* 1998, 33(7) 743-748); Sjogren's syndrome (see, for example, U. Kroneld et al., *Scand J. Gastroenterol* 1998, 27(3), 215-218); and rheumatoid arthritis (see, for example, *Scand J. Gastroenterol* 1996, 44(3), 293-298). And compounds that bind $\alpha_6\beta_1$ may be useful in preventing fertilization (see, for example, H. Chen et al., *Chem. Biol.* 1999, 6, 1-10).

In another aspect of the invention, the conjugates and compositions described herein can be used to inhibit immune cell migration from the bloodstream to the central nervous system in the instance of, for example, multiple sclerosis, or to areas which result in inflammatory-induced destruction of the myelin. Preferably, these reagents inhibit immune cell migration in a manner that inhibits demyelination and that further may promote remyelination. The reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

Inflammatory diseases that are included for treatment by the compositions, conjugates and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination. Additional diseases or conditions contemplated for treatment include meningitis, encephalitis, and spinal cord injuries and conditions generally which induce demyelination as a result of an inflammatory response. The conjugates, compositions and methods disclosed herein are not directed towards diseases and conditions wherein there is, for example, a genetic defect leading to improper myelin formation, e.g., dysmyelination.

The compositions, conjugates and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria, Tay-Sachs disease, Niemann-Pick disease, Gaucher's disease, Hurler's syndrome, Krabbe's disease and other leukodystrophies), neuropathies with abnormal myelination (e.g., Guillain Barré, chronic immune demyelinating polyneuropathy (CIDP), multifocal CIDP, anti-MAG syndrome, GALOP syndrome, anti-sulfatide antibody syndrome, anti-GM2 antibody syndrome, POEMS syndrome, perineuritis, IgM anti-GD1b antibody syndrome), drug related demyelination (e.g., caused by the administration of chloroquine, FK506, perhexiline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis or spinal cord injury) or diseases.

There are various disease models that can be used to study these diseases in vivo. For example, animal models include but are not limited to:

TABLE III

| Disease Model | Species |
| --- | --- |
| EAE | Mouse, rat, guinea pig |
| Myelin-oligodendrocyte glycoprotein (MOG) induced EAE | Rat |
| TNF-α transgenic model of demyelination | Mouse |

Multiple Sclerosis

The most common demyelinating disease is multiple sclerosis, but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

The cause of MS is yet to be determined. MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high-but not low-frequency trains of impulses or complete conduction block. Positive conduction abnormalities include ectopic impulse generation, spontaneously or following mechanical stress and abnormal "cross-talk" between demyelinated exons.

T cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include (1) treatment aimed at modification of the disease course, including treatment of acute exacerbation and directed to long-term suppression of the disease; (2) treatment of the symptoms of MS; (3) prevention and treatment of medical complications, and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather then in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-1 b, interferon beta-1a, and Copaxone® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

Congenital Metabolic Disorders

Congenital metabolic disorders include phenylketonuria (PKU) and other aminoacidurias, Tay-Sachs disease, Niemann-Pick disease, Gaucher's disease, Hurler's syndrome, Krabbe's disease and other leukodystrophies that impact the developing sheath as described more fully below.

PKU is an inherited error of metabolism caused by a deficiency in the enzyme phenylalanine hydroxylase. Loss of this enzyme results in mental retardation, organ damage, unusual posture and can, in cases of maternal PKU, severely compromise pregnancy. A model for studying PKU has been discovered in mice. Preferably infants identified with PKU are sustained on a phenylalanine free or lowered diet. An aspect of the invention would be to combine such diets with the conjugates and compositions disclosed herein to prevent demyelination and remyelinate cells damaged due to PKU.

Classical Tay-Sachs disease appears in the subject at about age 6 months and will eventually result in the death of the subject by age 5 years. The disease is due to the lack of the enzyme, hexoaminidase A (hex A), which is necessary for degrading certain fatty substances in the brain and nerve cells. The substances in the absence of the enzyme accumulate and lead to the destruction of nerve cells. Another form of hex A enzyme deficiency occurs later in life and is referred to as juvenile, chronic and adult onset forms of hex A deficiency. Symptoms are similar to those that characterize classical Tay-Sachs disease. There is also an adult onset form of the enzyme deficiency. Currently there is no cure or treatment for the disease/deficiency, only the preventative measure of in utero testing of the fetus for the disease. Thus, the conjugates and compositions disclosed herein may be useful in ameliorating or preventing the destruction of the cells.

Niemann-Pick disease falls into three categories: the acute infantile form, Type B is a less common, chronic, non-neurological form, and Type C is a biochemically and genetically distinct form of the disease. In a normal individual, cellular cholesterol is imported into lysosomes for processing, after which it is released. Cells taken from subjects with Niemann-Pick have been shown to be defective in releasing cholesterol from lysosomes. This leads to an excessive build-up of cholesterol inside lysosomes, causing processing errors. NPC1 was found to have known sterol-sensing regions similar to those in other proteins, which suggests it plays a role in regulating cholesterol traffic. No successful therapies have been identified for Types A and C forms of Neumann-Pick. For Type C, patients are recommended to follow a low-cholesterol diet. Thus, the conjugates and compositions disclosed herein may be useful in ameliorating or preventing the destruction of the cells.

Gaucher's disease is an inherited illness caused by a gene mutation. Normally, this gene is responsible for an enzyme called glucocerebrosidase that the body needs to break down the fat, glucocerebroside. In patients with Gaucher's disease, the body is not able to properly produce this enzyme and the fat cannot be broken down. Like Tay-Sachs disease, Gaucher's disease is considerably more common in the descendants of Jewish people from Eastern Europe (Ashkenazi), although individuals from any ethnic group may be affected. Among the Ashkenazi Jewish population, Gaucher's disease is the most common genetic disorder, with an incidence of approximately 1 in 450 persons. In the general public, Gaucher's disease affects approximately 1 in 100,000 persons.

In 1991, enzyme replacement therapy became available as the first effective treatment for Gaucher's disease. The treatment consists of a modified form of the glucocerebrosidase enzyme given intravenously. It is contemplated that the compositions and conjugates disclosed herein can be used alone or more preferably in combination with glycocerebrosidase administration to treat the disease in an afflicted subject.

Hurler's syndrome, also known as mucopolysaccharidosis type I, is a class of overlapping diseases. These genetic diseases share in common the cellular accumulation of mucopolysaccharides in fibroblasts. The diseases are genetically distinguishable. Fibroblast and bone marrow transplantation does not seem to be helpful, thus compounds and compositions useful in ameliorating disease severity and progression are needed. The conjugates and compositions disclosed herein may be administered to a subject to ameliorate disease progression and/or severity.

Krabbe's disease (also known as Globoid cell leukodystrophy) is an autosomal recessive condition resulting from galactosylceramidase (or galactocerebrosidase) deficiency, a lysosomal enzyme that catabolises a major lipid component of myelin. Incidence in France is an estimated 1:150,000 births. The disease leads to demyelination of the central and peripheral nervous system. Onset generally occurs during the first year of life and the condition is rapidly progressive, but juvenile, adolescent or adult onset forms have also been reported, with a more variable rate of progression. Diagnosis is established from enzyme assay (galactosylceramidase deficiency). There are several natural animal models (mouse, dog, monkey). Krabbe's disease, like all leukodystrophies, has no known cures or effective treatments. One embodiment of the instant invention is to use the compositions and conjugates disclosed herein to treat or ameliorate Krabbe's disease and other leukodystrophies.

Leukodystrophies are a group of genetically determined progressive disorders that affect the brain, spinal cord and peripheral nerves. They include adrenoleukodystrophy (ALD), adrenomyeloneuropathy (AMN), Aicardi-Goutiers syndrome, Alexander's disease, CACH (i.e., childhood ataxia with central nervous system hypomyelination or vanishing white matter disease), CADASIL (i.e., cerebral autosomal dominant arteriopathy with subcortical infarcts and leukoencephalopathy), Canavan disease (spongy degeneration), Cerebrotendinous Xanthomatosis (CTX), Krabbe's disease (discussed above), metachromatic leukodystrophy (MLD), neonatal adrenoleukodystrophy, ovarioleukodystrophy syndrome, Pelizaeus-Merzbacher disease (X-linked spastic paraglegia), Refsum disease, van der Knaap syndrome (vaculating leukodystrophy with subcortical cysts) and Zellweger syndrome. None of the diseases have effective treatments let alone cures. Consequently, means of treating or ameliorating the symptoms of the disease, such as by using the compositions and conjugates disclosed herein, is needed.

Neuropathies with Abnormal Myelination

A variety of chronic immune polyneuropathies exist which result in demyelination in the patient. The age of onset for the conditions varies by condition. Standard treatments for these diseases exist and could be combined with the compositions and conjugates disclosed herein. Alternatively, the compositions and conjugates disclosed can be used alone. Existing standard therapies include the following:

TABLE IV

| Neuropathy | Clinical Features | Treatment |
| --- | --- | --- |
| Chronic Immune Demyelinating Polyneuropathy (CIDP) | Onset between 1-80 years. Characterized by weakness, sensory loss, and nerve hypertrophy. | T-cell immunosuppression with prednisone, cyclosporine A or methotrexate, HIG, plasma exchange |

TABLE IV-continued

| Neuropathy | Clinical Features | Treatment |
| --- | --- | --- |
| Multifocal CIDP | Onset between 28 to 58 years and characterized by asymmetric weakness, sensory loss with a course that is slowly progressive or relapsing-remitting. | T cell immunosuppression with prednisone Human immunoglobulin (HIG) |
| Multifocal Motor Neuropathy (MMN) | Onset ranges from 25 to 70 years, with twice as many men as women. Features include weakness, muscle atrophy, fasciculations, and cramps which are progressive over 1-30 years. | HIG B cell immunosuppression with plasma exchange cyclophosphamide, Rituxan |
| Neuropathy with IgM binding to Myelin-Associated Glycoprotein (MAG) | Onset is usually over age 50 and is characterized by sensory loss (100%), weakness, gain disorder, tremor which is all slowly progressive. | B-cell immunosuppression plasma exchange cyclophosphamide Rituxan α-interferon cladribine or fludarabine prednisone |
| GALOP Syndrome (Gait disorder, Autoantibody, Late-age, Onset, Polyneuropathy) | A gait disorder with polyneuropathy | HIG Plasma exchange cyclophosphamide |
| POEMS Syndrome (Polyneuropathy, Organomegaly, Endocrinopathy, M-Protein and Skin changes) also known as Crow-Fukase Syndrome and Takatsuki disease | Onset occurs between 27 and 80 years with weakness, sensory loss, reduced or absent tendon reflexes, skin disorders and other features. | Osteosclerotic lesions are treated with irradiation. Widespread lesions with chemotherapy (Melphalan and prednisone). |

Drug and Radiation Induced Demyelination

Certain drugs and radiation can induce demyelination in subjects. Drugs that are responsible for demyelination include but are not limited to chloroquine, FK506, perhexiline, procainamide, and zimeldine.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of certain cancers. See for review Belka et al., 2001 Br. J. Cancer 85: 1233-9. However, radiation exposure may also be an issue for astronauts (Hopewell, 1994 Adv. Space Res. 14: 433-42) as well as in the event of exposure to radioactive substances.

Patients who have received drugs or been exposed accidentally or intentionally to radiation may experience a benefit by administered one of the conjugates or compositions disclosed herein to prevent demyelination or to promote remyelination.

Conditions Involving Demyelination

Additional inherited syndromes/diseases that result in demyelination include Cockayne's syndrome, congenital hypomyelinating, Farber's disease, metachromatic leukodystrophy, Peliszaeus-Merzbacher disease, Refsum, prion related conditions and Salla disease.

Cockayne's syndrome (CS) is a rare inherited disorder in which people are sensitive to sunlight, have short stature and have the appearance of premature aging. In the classical form of Cockayne's syndrome (Type I), the symptoms are progressive and typically become apparent after the age of one year. An early onset or congenital form of Cockayne's syndrome (Type II) is apparent at birth. Interestingly, unlike other DNA repair diseases, Cockayne's syndrome is not linked to cancer. CS is a multi-system disorder that causes both profound growth failure of the soma and brain and progressive cachexia, retinal, cochlear, and neurologic degeneration, with a leukodystrophy and demyelinating neuropathy without an increase in cancer. After exposure to UV (e.g., sunlight), subjects with Cockayne's syndrome can no longer perform transcription-coupled repair. Two genes defective in Cockayne's syndrome, CSA and CSB, have been identified so far. The CSA gene is found on chromosome 5. Both genes code for proteins that interacts with components of the transcriptional machinery and with DNA repair proteins.

To date, no cures or effective treatments for patients with this disease have been identified. Thus, one aspect of the invention is treatment of this disease with the conjugates and compositions disclosed herein.

Congenital hypomyelination has several names including congenital dysmyelinating neuropathy, congenital hypomyelinating polyneuropathy, congenital hypomyelination (Onion Bulb) polyneuropathy, congenital hypomyelination neuropathy, congenital neuropathy caused by hypomyelination, hypomyelination neuropathy and CHN. Hereditary peripheral neuropathies, among the most common genetic disorders in humans, are a complex, clinically and genetically heterogeneous group of disorders that produce progressive deterioration of the peripheral nerves. Congenital hypomyelination is one of a group of disorders. This group includes hereditary neuropathy with liability to pressure palsies, Charcot-Marie-Tooth disease, Dejerine-Sottas syndrome, and congenital hypomyelinating neuropathy. There are no known cures or effective treatments for any of these disorders.

Farber's disease has several names include: Farber lipogranulomatosis, ceremidase deficiency, acid ceramidase deficiency, AC deficiency, N-laurylsphingosine deacylase deficiency, and N-acylsphingosine amidohydrolase. As certain names reveal, the disease occurs due to a deficiency of acid ceramidase (also known as N-acylsphingosine amidohydrolase, ASAH). The lack of the enzyme results in an accumulation of non-sulfonated acid mucopolysaccharide in the neurons and glial cells. Patients with the disease usually die before the age of 2 years.

Metachromatic leukodystrophy (MLD) is a genetic disorder caused by a deficiency of the enzyme arylsulfatase A. It is one of a group of genetic disorders called the leukodystrophies that affect growth of the myelin sheath. There are three forms of MLD: late infantile, juvenile, and adult. In the late infantile form, which is the most common, onset of symptoms begins between ages 6 months and 2 years. The infant is usually normal at birth, but eventually loses previously gained abilities. Symptoms include hypotonia (low muscle tone), speech abnormalities, loss of mental abilities, blindness, rigidity (i.e., uncontrolled muscle tightness), convulsions, impaired swallowing, paralysis, and dementia. Symptoms of the juvenile form begin between ages 4 and 14, and include impaired school performance, mental deterioration, ataxia, seizures, and dementia. In the adult form, symptoms, which begin after age 16, may include impaired concentration, depression, psychiatric disturbances, ataxia, tremor, and dementia. Seizures may occur in the adult form, but are less common than in the other forms. In all three forms mental deterioration is usually the first sign.

Peliszaeus-Merzbacher disease (also known as perinatal sudanophilic leukodystrophy) is an X-linked genetic disorder that causes an abnormality of a proteolipid protein. The abnormality results in an infant's death typically before the age of one year. There are no known treatments or cures for the disease.

Refsum disease (also referred to as phytanic acid oxidase deficiency, heredopathia atactica polyneuritiformis or hereditary motor and sensory neuropathy IV, HMSN IV) is caused by mutations in the gene, which encodes phytanoyl-CoA hydroxylase (PAHX or PHYH). The major clinical features are retinitis pigmentosa, chronic polyneuropathy and cerebellar signs. Phytanic acid, an unusual branched chain fatty acid (3,7,11,15-tetramethyl-hexadecanoic acid) accumulates in the tissues and body fluids of patients with the disease and is unable to be metabolised due to the lack of PAHX. Plasmapheresis performed once or twice monthly effectively removes the acid from the body and permits liberalization of dietary restrictions limiting phytanic acid intake.

Prion related conditions include Gerstmann-Straussler disease (GSD), Creutzfeldt-Jakob disease (CJD), familial fatal insomnia and aberrant isoforms of the prion protein can act as infectious agents in these disorders as well as in kuru and scrapie (a disease found in sheep). The term prion derives from "protein infectious agent" (Prusiner, Science 216: 136-44, 1982). There is a proteolytic cleavage of the prion related protein (PRP) which results in an amyloidogenic peptide that polymerises into insoluble fibrils.

Salla disease and other types of sialurias are diseases involving problems with sialic acid storage. They are autosomal recessive neurodegenerative disorders that may present as a severe infantile form (i.e., ISSD) or as a slowly progressive adult form that is prevalent in Finland (i.e., Salla disease). The main symptoms are hypotonia, cerebellar ataxia and mental retardation. These conditions and diseases are also contemplated for palliative or ameliorating treatments.

Other conditions that result in demyelination include postinfectious encephalitis (also known as acute disseminated encephalomyelitis, ADEM), meningitis and injuries to the spinal cord. The compositions and conjugates disclosed herein are also contemplated for use in treating these other demyelinating conditions.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

ACN=acetonitrile
bs=broad singlet
Boc=N-tert-butoxylcarbonyl
BOP=benzotriazol-1-yloxy-tris(dimethylamino)phosphonium hexafluorophosphate
Cbz=carbobenzyloxy
$CH_2Cl_2$=dichloromethane
d=doublet
dd=doublet of doublets
DCC=1,3-dicyclohexylcarbodiimide
DMAP=4-N,N-dimethylaminopyridine
EDC=1-(3-dimethylaminopropyl)-3-ethylcarbodiimide hydrochloride
$Et_3N$=triethylamine
FmocONSu=N-(9-fluorenylmethoxycarbonyl)succinimide
g=grams
h and hr=hour
$H_2O$=water
HOBT=1-hydroxybenzotriazole hydrate
HPLC=High performance (or pressure) liquid chromatography
kg=kilogram
$K_2CO_3$=potassium carbonate
kDa=kilodalton
L=liter
m=multiplet
MeOH=methanol
M=Molar
mg=milligram
min=minute
mL=milliliter
mm=millimeter
mM=millimolar
mmol=millimol
N=normal
$NaHCO_3$=sodium bicarbonate
nM=nanomolar
q=quartet
s=singlet
sat.=saturated
t=triplet
t-BuOH=tert-butanol
TFA=trifluoroacetic acid
TLC or tlc=thin layer chromatography
Ts=tosyl
TsCl=tosyl chloride
TsOH=tosylate
µL=microliter
µg=microgram
µm=micron or micrometer The following methods may be used to prepare the conjugates of this invention. In one method outlined in Scheme 16 below is illustrative of such preparation.

Scheme 16

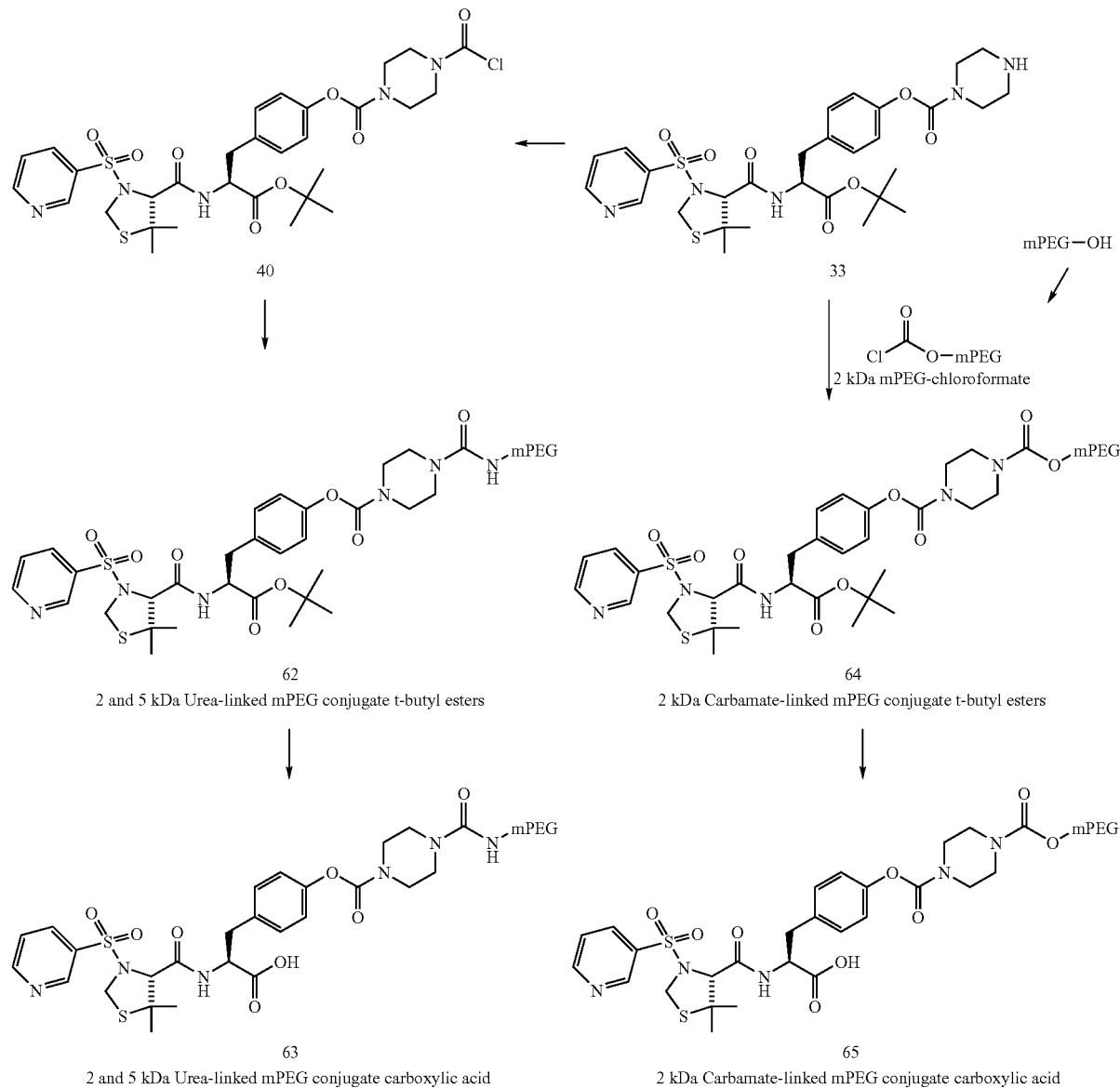

40

2 and 5 kDa Urea-linked mPEG conjugate t-butyl esters
62

2 and 5 kDa Urea-linked mPEG conjugate carboxylic acid
63

33

2 kDa mPEG-chloroformate 2 kDa Carbamate-linked mPEG conjugate t-butyl esters
64

2 kDa Carbamate-linked mPEG conjugate carboxylic acid
65

The following Examples describe methods for preparing the compounds and conjugates shown in Scheme 6 and Scheme 16 above. Unless otherwise indicated some or all of the following HPLC methods were used in the preparation of the following exemplary compounds.

Method A: Samples of conjugates of more than 100 mg were purified using reverse phase HPLC on a Phenomenex Luna C18(2), 5 μm column 250 mm×21.2 mm with a Varian UV detector, using a gradient of 40-60% ACN+0.1% TFA in 100 min at 15 mL/min.

Method B: Samples of conjugates of more than 100 mg but less than 500 mg were purified using reverse phase HPLC on a Phenomenex Luna C18(2), 10 μm column 250 mm×50 mm with a Varian UV detector using a gradient of 40-60% ACN+ 0.1% TFA in 100 min at 60 mL/min.

Method C: The purity of conjugates was confirmed using reverse phase HPLC on a Luna 3 μm C18(2) column (30×4.6 mm) with a Sedex 75 (35° C., gain=5) evaporative light scattering detector, using a gradient of 20-70% ACN w/0.1% TFA at a flow rate of 1.5 mL/min.

Example 1

Preparation of 2 kDa Urea-Linked mPEG Conjugate Carboxylic Acid

Step 1: Preparation of Compound 29:

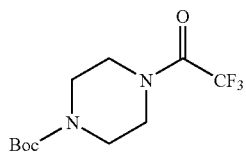

Compound 25 (20 g, 0.11 mol) (as shown in Scheme 6 above) was dissolved in CH$_2$Cl$_2$ (500 mL) under N$_2$. The reaction mixture was cooled to 0° C. Triethylamine (18.12 mL, 0.13 mol) was added, followed by trifluoroacetic anhydride (18.14 mL, 0.13 mol) in portions. The reaction was allowed to warm to room temperature overnight. The reaction mixture was concentrated in vacuo and the residue was taken up in ethyl acetate (200 mL). The organic phase was washed with $H_2O$, sat. $NaHCO_3$, brine, dried over $Na_2SO_4$, filtered, and concentrated in vacuo to yield 29.73 g (96%) of the title compound, 29, as a yellow solid.

$^1$H NMR (CDCl$_3$) δ 3.64-3.60 (m, 2H), 3.55-3.53 (m, 2H), 3.49-3.45 (m, 4H), 1.44 (s, 9H).

$^{13}$C NMR (CDCl$_3$) δ 155.7 ($J_{C-F}$=36 Hz), 154.3, 116.4 ($J_{C-F}$=288 Hz), 80.8, 45.7, 43.3, 28.3.

Step 2: Preparation of Compound 30:

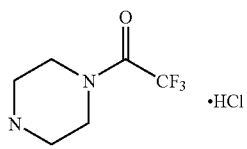

Compound 29 (29.26 g, 0.10 mol) was added in portions to a 500 mL flask containing a solution of 4N HCL in dioxane (200 mL) at 0° C. The reaction was stirred in ice bath for 4 hours when TLC (3:1 hexanes:ethyl acetate) showed 100% conversion to product. The reaction mixture was concentrated in vacuo and treated with ethyl ether (500 mL). The product was filtered and dried to yield 22.53 g (99%) compound 30 as a white mono-hydrochloride salt.

$^1$H NMR (DMSO-d$_6$) δ 3.82-3.79 (m, 4H), 3.53 (S, 1H), 3.18-3.16 (m, 4H).

$^{13}$C NMR (DMSO-d$_6$) δ 154.3 ($J_{C-F}$=35 Hz), 115.9 ($J_{C-F}$=289 Hz), 66.1, 42.0, 41.9, 41.5.

Step 3: Preparation of Compound 31:

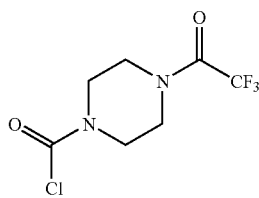

A 250 mL flask was charged with compound 30 (1.0 g, 4.6 mmol), $CH_2Cl_2$ (40 mL), and sat. $NaHCO_3$ (40 mL). The reaction mixture was stirred vigorously at 0° C. for 15 minutes. Stirring was ceased and the layers were allowed to separate. A 2.0 M solution of phosgene in toluene (9 mL, 18 mmol) was added to the reaction mixture which was stirred vigorously for 30 minutes, while maintaining temperature at 0° C. The layers were separated and the aqueous phase was washed with $CH_2Cl_2$ (15 mL). The combined organic layers were washed with brine, dried over $Na_2SO_4$, filtered, and concentrated in vacuo. The residue was taken up in $CH_2Cl_2$ and concentrated in vacuo again to yield 1.04 g (92%) compound 31 as a white solid.

MS(PI-FAB) 245, (M+H)$^+$.

$^1$H NMR (CDCl$_3$) δ 3.80-3.68 (m, 8H).

$^{13}$C NMR (CDCl$_3$) δ 155.9 ($J_{C-F}$=37 Hz), 148.7 ($J_{C-F}$=12 Hz), 116.3 ($J_{C-F}$=289 Hz), 48.3, 47.8, 45.7, 45.3, 45.1, 42.9, 42.7.

Step 4: Preparation of Compound 32

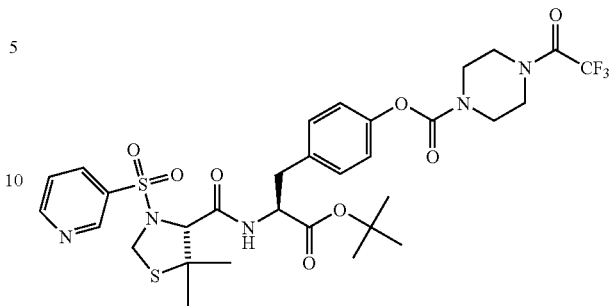

A 25 mL flask was charged with compound 24 (5.97 g, 0.011 mol), DMAP (1.34 g, 0.011 mol), and $CH_2Cl_2$ (22 mL). Triethylamine (2.4 mL, 0.017 mol) was added followed by compound 31 (4.2 g, 0.017 mol). The reaction mixture was heated at reflux for 20 hours. The reaction mixture was concentrated in vacuo and the residue was taken up in ethyl acetate. The organic phase was washed with sat. $NaHCO_3$, $H_2O$, brine, dried over $Na_2SO_4$, filtered, and concentrated in vacuo to yield 9.31 g (115%) pink foam. The crude material was purified by flash chromatography (gradient of 50% ethyl acetate/hexanes to 75% ethyl acetate/hexanes) to yield 6.1 g (76%) compound 32 as a pale pink foam. $R_f$=0.14 (1:1 hexanes:ethyl acetate).

MS(PI-FAB) 730, (M+H)$^+$.

$^1$H NMR (CDCl$_3$) δ 9.08-9.07 (m, 1H), 8.87-8.85 (m, 1H), 8.16-8.14 (m, 1H), 7.52-7.48 (m, 1H), 7.25-7.22 (d, 2H), 7.03-7.00 (d, 2H), 6.91-6.88 (d, 1H), 4.78-4.70 (q, 1H), 4.60-4.44 (dd, 2H), 3.88 (s, 1H), 3.75-3.60 (m, 8H), 3.09-3.06 (m, 2H), 1.42 (s, 9H), 1.18 (s, 3H), 1.16 (s, 3H).

Step 5: Preparation of Compound 33

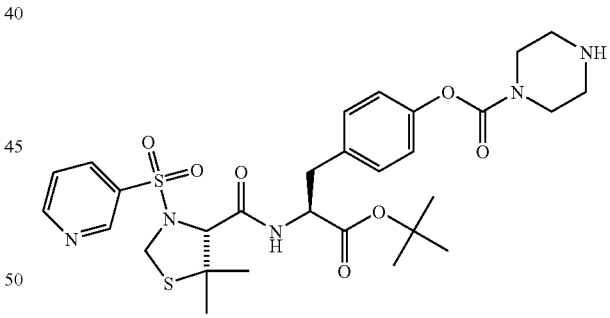

To a solution of compound 32 (6.11 g, 8.4 mmol) dissolved in MeOH (90 mL) was added a solution of potassium carbonate (5.79 g, 42 mmol) in $H_2O$ (10 mL). The reaction was stirred at room temperature for 15 minutes and then concentrated in vacuo. The residue was filtered and washed with copious amounts of $H_2O$ to yield 4.65 g (88%) compound 33 as a white solid. $R_f$=0.08 (5% MeOH/$CH_2Cl_2$).

MS(PI-FAB) 634, (M+H)$^+$.

$^1$H NMR (CDCl$_3$) δ 9.09-9.08 (m, 1H), 8.87-8.85 (m, 1H), 8.16-8.14 (m, 1H), 7.52-7.48 (m, 1H), 7.23-7.20 (d, 2H), 7.03-7.00 (d, 2H), 6.91-6.88 (d, 1H), 4.78-4.70 (q, 1H), 4.59-4.46 (dd, 2H), 3.89 (s, 1H), 3.65-3.50 (m, 4H), 3.09-3.06 (m, 2H), 2.92-2.88 (m, 4H), 1.43 (s, 9H), 1.19 (s, 3H), 1.17 (s, 3H).

$^{13}$C NMR (CDCl$_3$) δ 170.1, 167.9, 154.5, 153.9, 150.7, 148.8, 136.0, 133.4, 133.2, 130.6, 124.1, 121.9, 83.0, 73.9, 55.0, 53.7, 50.7, 46.0, 45.7, 45.0, 37.9, 29.3, 28.0, 24.0.

Step 6: Preparation of Compound 40

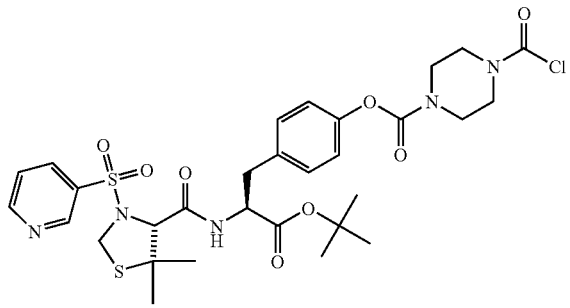

A 250 mL flask was charged with compound 33 (2.5 g, 3.9 mmol), CH$_2$Cl$_2$ (40 mL), and sat. NaHCO$_3$ (40 mL). The reaction mixture was stirred vigorously at 0° C. for 15 minutes. Stirring was ceased and the layers were allowed to separate. A 2.0 M solution of phosgene in toluene (7.9 mL, 16 mmol) was quickly added to the reaction mixture which was stirred vigorously for 60 minutes maintaining the temperature at 0° C. The layers were separated and the aqueous phase was washed with CH$_2$Cl$_2$ (30 mL). The combined organic layers were washed with 0.2 N citric acid, brine, dried over Na$_2$SO$_4$, filtered, and concentrated in vacuo to yield 2.76 g (100%) white foam. The crude material was purified through a silica plug, eluting with 100% ethyl acetate, to yield 2.15 g (78%) compound 40 as a white foam. R$_f$ 0.43 (3:1 ethyl acetate: hexanes).

$^1$H NMR (CDCl$_3$) δ 9.09-9.08 (m, 1H), 8.87-8.85 (m, 1H), 8.16-8.14 (d, 1H), 7.52-7.48 (m, 1H), 7.25-7.22 (d, 2H), 7.03-7.01 (d, 2H), 6.90-6.88 (d, 1H), 4.78-4.70 (q, 1H), 4.60-4.45 (dd, 2H), 3.88 (s, 1H), 3.79-3.65 (m, 8H), 3.10-3.07 (m, 2H), 1.43 (s, 9H), 1.18 (s, 3H), 1.17 (s, 3H).

$^{13}$C NMR (CDCl$_3$) δ 169.9, 167.9, 154.1, 153.6, 150.2, 148.5, 136.1, 133.8, 130.6, 124.2, 121.7, 82.9, 73.7, 54.8, 53.8, 50.6, 48.3, 45.8, 37.7, 29.2, 27.9, 23.9.

Step 7: Preparation 2 kDa Urea-Linked mPEG Conjugate t-butyl Ester

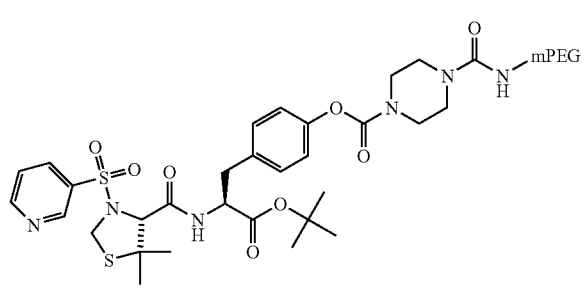

The 2 kilodalton mPEG-amine (192 mg, 0.09 mmol) and DMAP (11 mg, 0.09 mmol) were dissolved in CH$_2$Cl$_2$ (0.6 mL). Triethylamine (19.5 μL, 0.14 mmol) was added, followed by compound 40 (100 mg, 0.14 mmol). The reaction mixture was heated to reflux for 20 hours. The reaction was concentrated in vacuo and the residue was taken up in MeOH (25 mL). 2% cross-linked polystyrene sulfonic acid resin (300 mg) was added and reaction vessel was swirled for 2 hours. The mixture was then filtered and concentrated in vacuo to yield 182 mg (~50%) of a beige solid which was purified by HPLC method B yielding 50.7 mg 2 kDa mPEG conjugate t-butyl ester as a white wax. R$_f$ 0.12 (5% MeOH/CH$_2$Cl$_2$). HPLC method C determined conjugate to be >99% pure with no remaining compound 33 or mPEG-amine (retention time=1.924).

$^1$H NMR (CDCl$_3$) δ 8.21-8.18 (d, 1H), 7.23-7.21 (d, 2H), 7.03-7.00 (d, 2H), 6.91-6.88 (d, 1H), 4.76-4.73 (q, 1H), 4.60-4.46 (dd, 2H), 3.91-3.86 (m, 3H), 3.64 (bs, 184H), 3.37 (s, 3H), 3.09-3.06 (m, 3H), 1.43 (s, 9H), 1.20 (s, 3H), 1.17 (s, 3H).

Step 8: Preparation 2 kDa Urea-Linked mPEG Conjugate Carboxylic Acid

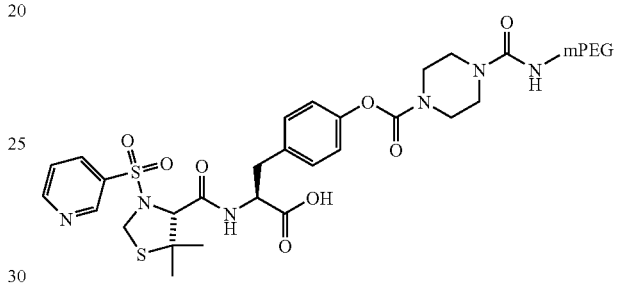

The 2 kDa urea-linked mPEG conjugate t-butyl ester (94 mg, 0.04 mmol) was dissolved in formic acid (5 mL) and heated at 40° C. for 48 hours. The reaction was concentrated in vacuo to yield 88 mg (100%) beige gel, which was purified by HPLC Method A to yield 53.7 mg (~60%) of the free carboxylic acid as a white wax. R$_f$=0.45 (7/3 MeOH:H$_2$O+ 0.1% TFA; C-18 Reverse Phase). HPLC method C determined conjugate to be >99% pure (retention time=2.188)

$^1$H NMR (CDCl$_3$) δ 9.07 (bs, 1H), 8.86-8.85 (m, 1H), 8.23-8.20 (d, 1H), 7.59-7.55 (m, 1H), 7.26-7.21 (d, 2H), 7.02-6.96 (m, 2H), 4.82-4.80 (m, 1H), 4.60-4.49 (dd, 2H), 3.99 (s, 1H), 3.62 (bs, 184H), 3.37 (s, 3H), 3.15-3.13 (m, 2H), 1.25 (s, 3H), 1.23 (s, 3H).

Example 2

Preparation of 5 kDa Urea-Linked mPEG Conjugate Carboxylic Acid

The 5 kDa urea-linked mPEG conjugate t-butyl ester was prepared in the same manner as the 2 kDa conjugate above, using a 5 kDa mPEG-amine, and yielded 476 mg (~90%) white solid. The crude material (200 mg, 0.04 mmol) was deprotected in the same manner as above yielding 182 mg (100%) beige gum. This was purified by HPLC method B, yielding 74.5 mg of the 5 kDa urea-linked mPEG conjugate carboxylic acid as a white powder. R$_f$=0.16 (7/3 MeOH:H$_2$O+ 0.1% TFA; C-18 Reverse Phase). HPLC method C determined conjugate to be >99% pure (retention time=2.260).

$^1$H NMR (CDCl$_3$) δ 9.07 (bs, 1H), 8.86-8.85 (m, 1H), 8.17-8.15 (d, 1H), 7.54-7.50 (m, 1H), 7.26-7.22 (d, 2H), 7.03-7.00 (d, 2H), 6.95-6.93 (d, 1H), 5.46 (bs, 1H), 4.83-4.81

(m, 1H), 4.60-4.46 (dd, 2H), 3.93 (s, 1H), 3.64 (bs, 490H), 3.37 (s, 3H), 3.16 (m, 3H), 1.22 (s, 6H).

Example 3

Preparation of 2 kDa Carbamate-Linked mPEG Conjugate t-butyl Ester

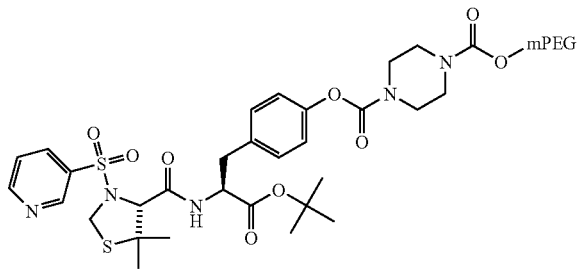

The carbamate linked conjugates were prepared based on a method modified from International Patent Publication Number WO 92/16555. Thus, a 2 kDa mPEG-alcohol (500 mg, 0.25 mmol) was dried by azeotropic distillation in toluene (5 mL). The solution was cooled to room temperature and $CH_2Cl_2$ (5 mL) was added, followed by a 2.0 M solution of phosgene in toluene (0.38 mL, 0.75 mmol). The reaction was stirred at room temperature for 18 hours and then concentrated in vacuo to yield 500 mg (100%) of the 2 kDa mPEG chloroformate as a white solid. A solution of compound 33 (317 mg, 0.5 mmol) in $CH_2Cl_2$ (3 mL) was added to the 2 kDa mPEG chloroformate (500 mg, 0.25 mmol) dissolved in $CH_2Cl_2$ (2 mL). Triethylamine (35 µL, 0.25 mmol) was added and reaction was stirred at room temperature for 30 minutes. The reaction mixture was concentrated in vacuo and the residue was taken up in MeOH (10 mL). 2% cross-linked polystyrene sulfonic acid resin (750 mg) was added and the reaction vessel was swirled for 2 hours. The mixture was then filtered and concentrated in vacuo to yield 470 mg (75%) of the 2 kDa carbamate-linked mPEG conjugate t-butyl ester as a white solid. HPLC method C shows >96% pure (retention time=2.639).

Example 4

Preparation of 2 kDa Carbamate-Linked mPEG Conjugate Carboxylic Acid

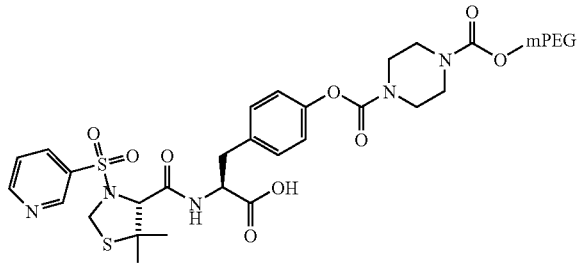

The crude 2 kDa carbamate-linked mPEG conjugate t-butyl ester (250 mg, 0.1 mmol) was dissolved in formic acid (5 mL) and heated at 40° C. for 48 hours. The reaction was concentrated in vacuo to yield 280 mg (100%) of the 2 kDa carbamate-linked mPEG conjugate carboxylic acid as a beige gel.

Biological Examples

Example A

In vitro Assay For Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to $IC_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human $IgG_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM $MnCl_2$ and 5 µg/mL 15/7 antibody for 30 minutes on ice. $Mn^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Biol. Chem. 271:11067) and may be used in this assay.

Cells were then incubated for 30 minutes at room temperature with candidate compounds, in various concentrations ranging from 66 µM to 0.01 µM using a standard 5-point serial dilution. 15 µL soluble recombinant VCAM-1 fusion protein was then added to Jurkat cells and incubated for 30 minutes on ice. (Yednock et al., supra.).

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an $IC_{50}$ of less than about 15 µM possess binding affinity to $\alpha_4\beta_1$.

When tested in this assay, each of the conjugates prepared in the above examples has or is expected to have an $IC_{50}$ of 15 µM or less (or is expected to be active in vivo).

Example B

In vitro Saturation Assay For Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In Vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053-1059, and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate. The mixture was emulsified by circulating it repeatedly through a 20 ml syringe with a peristaltic pump for about 20 minutes.

Female Lewis rats (2-3 months old, 170-220 g) or Hartley guinea pigs (20 day old, 180-200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053-1059), which delays the onset of symptoms, was used as a positive control and was injected subcutaneously at 3 mg/kg on Day 8 and 11.

Body weight and motor impairment were measured daily. Motor impairment was rated with the following clinical score:

| | |
|---|---|
| 0 | no change |
| 1 | tail weakness or paralysis |
| 2 | hindlimb weakness |
| 3 | hindlimb paralysis |
| 4 | moribund or dead |

A candidate compound was considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, J. Clin. Invest, 93:776-787 (1994) and Abraham et al, Am J.

Respir Crit Care Med, 156:696-703 (1997), both of which are incorporated by reference in their entirety. Compounds of this invention are formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 μm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at VT of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.

2. Add approximately 90.0 mL saline and sonicate until dissolved.

3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:

1. Add 0.300 g of the candidate compound into a 10.0 mL volumetric flask.

2. Add approximately 9.7 mL of 0.5% sodium bicarbonate/saline stock solution.

3. Sonicate until the candidate compound is completely dissolved.

4. Q.S. to 10.0 mL with 0.5% sodium bicarbonate/saline stock solution and mix thoroughly.

Using a conventional oral formulation, compounds of this invention would be active in this model.

Example E

Allograft Model

Allograft rejection, associated with infiltration of inflammatory cells, is the leading obstacle to long-term allograft survival. Cell surface adhesion molecules facilitate alloantigen recognition in vitro and may be critical for lymphocyte traffic in vivo. The following describes a model which can be used to study the in vivo effects of the compounds of this invention in the control of allograft rejection.

The following procedures are described in Coito et al., Transplantation (1998) 65(6):699-706 and in Korom et al., Transplantation (1998) 65(6):854-859, both of which are incorporated by reference in their entirety.

Following the procedures described in Coito and Korom, male adult rats weighing approximately 200-250 g are used in this model. Lewis rats are used as the recipients of cardiac allografts from Lewis X Brown Norway rats. Hearts are transplanted into the abdominal great vessels using standard microvascular techniques.

A candidate compound is administered to the transplant recipient in a suitable pharmaceutical carrier for a 7-day course of treatment starting the day of the engraftment. Doses range from 0.3 to 30 mg/kg/day. Control recipients receive the pharmaceutical carrier only. The rats are euthanized and their cardiac allografts are analyzed as described in Coito and Korom.

Using conventional formulations, compounds of this invention would be active in this model.

Example F

In vitro Saturation Assay for Determining Binding of Candidate Compounds to α4β1

The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 μg/ml of the 15/7 antibody (described in the above example).

The Jurkat cells are diluted two-fold into either normal plasma samples containing known candidate compound amounts in various concentrations ranging from 66 μM to 0.01 μM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. By measuring the fluorescence generated by test samples at various dilutions against the standard curve, the concentration of a compound in the blood can be determined. Compound half life can be determined, as well as the frequency of dosing required to maintain levels in the upper plateau of the curve, which represents the levels needed to obtain efficacy in an in vivo model.

Example G

Adjuvant-Induced Arthritis in Rats

Adjuvant induced arthritis ("AIA") is an animal model useful in the study of rheumatoid arthritis (RA), which is induced by injecting *M. tuberculosis* in the base of the tail of Lewis rats. Between 10 and 15 days following injection, animals develop a severe, progressive arthritis.

Generally, compounds are tested for their ability to alter hind paw swelling and bone damage resulting from adjuvant-induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135-1141 (1977).

Using an animal model of RA, such as AIA, enables one to study the cellular events involved in the early stages of the disease. CD44 expression on macrophages and lymphocytes is up-regulated during the early development of adjuvant arthritis, whereas LFA-1 expression is up-regulated later in the development of the disease. Understanding the interactions between adhesion molecules and endothelium at the earliest stages of adjuvant arthritis could lead to significant advances in the methods used in the treatment of RA.

The invention has been described with reference to various specific and preferred embodiments and techniques. However, it should be understood that many variations and modifications may be made while remaining within the spirit and scope of the invention.

REFERENCES

The following publications, patents and patent applications are cited in this application as superscript numbers:
1 Hemler and Takada, European Patent Application Publication No. 330,506, published Aug. 30, 1989
2 Elices, et al., Cell, 60:577-584 (1990)
3 Springer, Nature, 346:425-434 (1990)
4 Osborn, Cell, 62:3-6 (1990)
5 Vedder, et al., Surgery, 106:509 (1989)
6 Pretolani, et al., J. Exp. Med., 180:795 (1994)
7 Abraham, et al., J. Clin. Invest., 93:776 (1994)
8 Mulligan, et al., J. Immunology, 150:2407 (1993)
9 Cybulsky, et al., Science, 251:788 (1991)
10 Li, et al., Arterioscler. Thromb., 13:197 (1993)
11 Sasseville, et al., Am. J. Path., 144:27 (1994)
12 Yang, et al., Proc. Nat. Acad. Science (USA), 90:10494 (1993)
13 Burkly, et al., Diabetes, 43:529 (1994)
14 Baron, et al., J. Clin. Invest., 93:1700 (1994)
15 Hamann, et al., J. Immunology, 152:3238 (1994)
16 Yednock, et al., Nature, 356:63 (1992)
17 Baron, et al., J. Exp. Med., 177:57 (1993)
18 van Dinther-Janssen, et al., J. Immunology, 147:4207 (1991)
19 van Dinther-Janssen, et al., Annals. Rheumatic Dis., 52:672 (1993)
20 Elices, et al., J. Clin. Invest., 93:405 (1994)
21 Postigo, et al., J. Clin. Invest., 89:1445 (1991)
22 Paul, et al., Transpl. Proceed., 25:813 (1993)
23 Okarhara, et al., Can. Res., 54:3233 (1994)
24 Paavonen, et al., Int. J. Can., 58:298 (1994)
25 Schadendorf, et al., J. Path., 170:429 (1993)
26 Bao, et al., Diff., 52:239 (1993)
27 Lauri, et al., British J. Cancer, 68:862 (1993)
28 Kawaguchi, et al., Japanese J. Cancer Res., 83:1304 (1992)
29 Kogan, et al., U.S. Pat. No. 5,510,332, issued Apr. 23, 1996
30 International Patent Appl. Publication No. WO 96/01644
31 Thorsett, et al., U.S. Pat. No. 6,489,300, issued Dec. 3, 2002.

All of the above publications, patents and patent applications are herein incorporated by reference in their entirety to the same extent as if each individual publication, patent or patent application was specifically and individually indicated to be incorporated by reference in its entirety.

What is claimed is:
1. A conjugate of formula I:

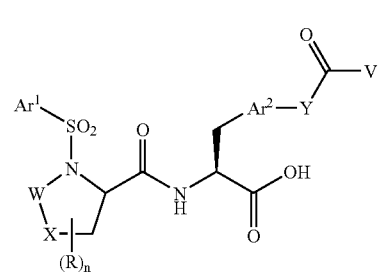

or a pharmaceutically acceptable salt thereof, wherein
R is a POAM moiety or $R_a$, where $R_a$ is selected from the group consisting of amino, hydroxyl, alkoxy, substituted alkoxy, substituted amino, alkyl, substituted alkyl, -alkyl-O-alkyl, substituted -alkyl-O-alkyl, wherein each R$_a$ is optionally substituted with a POAM moiety covalently bonded to R$_a$ optionally by a linker;

Ar$^1$ is selected from the group consisting of heteroaryl and substituted heteroaryl, wherein each Ar$^1$ is optionally substituted with a POAM moiety covalently bonded to Ar$^1$ optionally by a linker;

Ar$^2$ is phenyl or substituted phenyl, where each phenyl group is optionally further substituted with a POAM moiety covalently bonded to Ar$^2$ optionally by a linker;

W is —(CH$_2$)—;

X is selected from the group consisting of —S—, —SO—, —SO$_2$ and optionally substituted —OH$_2$—;

Y is selected from the group consisting of —O—, —S— and —NR$^1$— wherein R$^1$ is selected from the group consisting of hydrogen and C$_1$-C$_5$ alkyl;

V is
—NR$^2$R$^3$ where R$^2$ and R$^3$ together with the nitrogen to which they are attached represent a heterocyclic ring or a substituted heterocyclic ring, and
wherein V is optionally substituted with a POAM moiety covalently bonded to the heterocyclic ring, or substituted heterocyclic ring optionally by a linker; and n is 0, 1 or 2;

provided that at least one of R, Ar$^1$, Ar$^2$, and V contains a POAM moiety;

further provided that when R is a POAM moiety, n is one and X is not —S—, —SO—, or —SO$_2$—;

and still further provided that the conjugate of formula I has a molecular weight of no more than 100,000.

2. A conjugate according to claim 1, of the formula Ia:

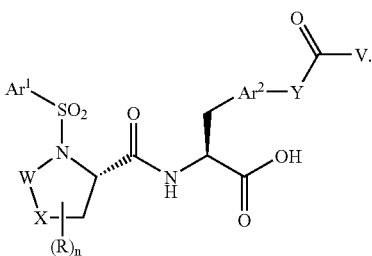

or a pharmaceutically acceptable salt thereof.

3. A conjugate according to claim 1, of the formula II:

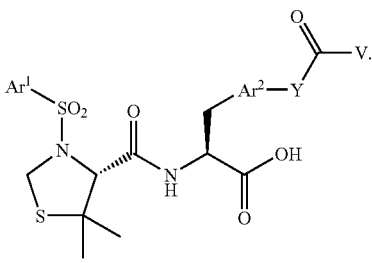

or a phamaceutically acceptable salt thereof.

4. A conjugate according to claim 1, of the formula III:

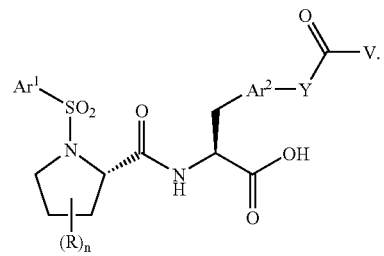

or a pharmaceutically acceptable salt thereof.

5. A conjugate according to claim 1, of the formula IV:

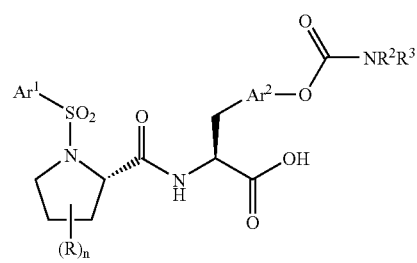

or a pharmaceutically acceptable salt thereof,
provided that at least one of R, Ar$^1$, Ar$^2$, and —NR$^2$R$^3$ contains a POAM moiety which optionally comprises a linker.

6. A conjugate according to claim 1, of the formula V:

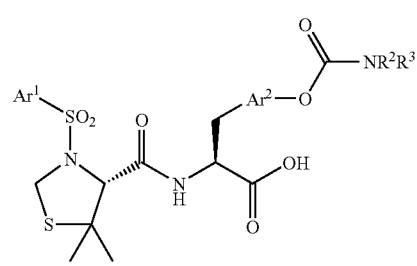

or a pharmaceutically acceptable salt thereof,
provided that at least one of Ar$^1$, Ar$^2$ and —NR$^2$R$^3$ contains a POAM moiety which optionally comprises a linker.

7. A conjugate according to claim 1, of the formula VI:

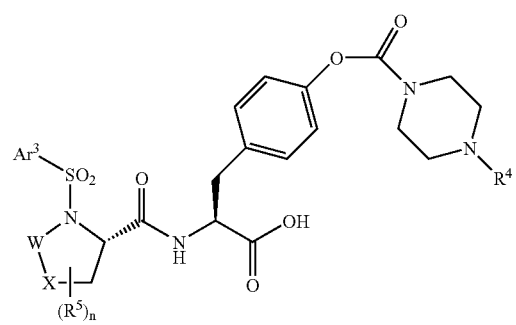

or a pharmaceutically acceptable salt thereof, wherein R$^4$ is a POAM moiety covalently bonded to the ring optionally by a linker;

R[5] is selected from the group consisting of alkyl and substituted alkyl;
Ar[3] is selected from the group consisting of heteroaryl and substituted heteroaryl;
X is selected from the group consisting of —S— and optionally substituted —CH$_2$—; and
n is 0, 1, or 2.

8. A conjugate according to claim 1, of the formula VII:

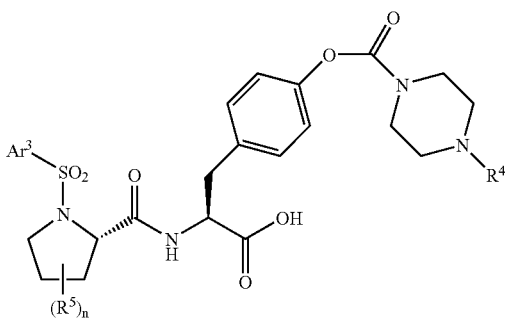

VII or a pharmaceutically acceptable salt thereof, wherein
R[4] is a POAM moiety covalently bonded to the ring optionally by a linker;
R[5] is selected from the group consisting of alkyl and substituted alkyl;
Ar[3] is selected from the group consisting of heteroaryl and substituted heteroaryl; and
n is 0, 1, or 2.

9. A conjugate according to claim 1, of the formula VIII:

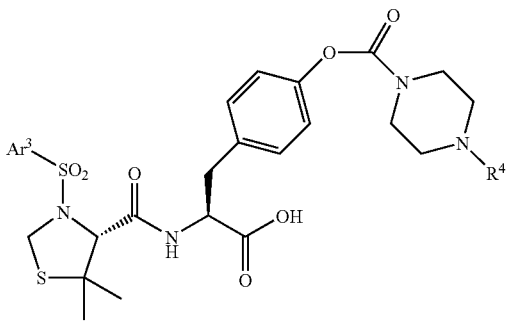

VIII or a pharmaceutically acceptable salt thereof, wherein
R[4] is a POAM moiety covalently bonded to the ring optionally by a linker; and
Ar[3] is selected from the group consisting of heteroaryl and substituted heteroaryl.

10. A conjugate according to claim 1 wherein, when Ar[1] does not contain a POAM moiety, Ar[1] is selected from the group consisting of:
pyridin-2-yl,
pyridin-3-yl,
pyridin-4-yl,
pyrimidin-2-yl,
quinolin-8-yl,
2-(trifluoroacetyl)-1,2,3,4-tetrahydroisoquinolin-7-yl,
2-thienyl,
5-chloro-2-thienyl,
2,5-dichloro-4-thienyl,
1-N-methylimidazol-4-yl,
1-N-methylpyrazol-3-yl,
1-N-methylpyrazol-4-yl,
1-N-butylpyrazol-4-yl,
1-N-methyl-3-methyl-5-chloropyrazol-4-yl,
1-N-methyl-5-methyl-3-chloropyrazol-4-yl,
2-thiazolyl and
5-methyl-1,3,4-thiadiazol-2-yl.

11. A conjugate according to claim 1 wherein when Ar[1] contains a POAM group, Ar[1], the POAM group and the optional linker are represented by the formula:

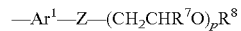

wherein
Ar[1] is selected from the group consisting of heteroaryl, and substituted heteroaryl,
Z is selected from the group consisting of a covalent bond, a linking group of from 1 to 40 atoms, —O—, —S— and —NR[9]—, where R[9] is selected from the group consisting of hydrogen and C$_1$-C$_5$ alkyl,
R[7] is selected from the group consisting of hydrogen and methyl;
R[8] is selected from the group consisting of hydrogen, alkyl, substituted alkyl, aryl, substituted aryl, and —CH$_2$CHR[7]NR[10]R[11] where R[7] is as defined above and R[10] and R[11] are independently selected from the group consisting of hydrogen and alkyl; and
p is an integer such that the molecular weight of the POAM moiety ranges from about 100 to 100,000.

12. A conjugate according to claim 1 wherein
n is 1; and
R represents —Z—(CH$_2$CHR[7]O)R[8] where
Z is selected from the group consisting of a covalent bond, a linking group of from 1 to 40 atoms, —O—, —S— and —NR[9]—, where R[9] is selected from the group consisting of hydrogen and C$_1$-C$_5$ alkyl,
R[7] is selected from the group consisting of hydrogen and methyl;
R[8] is selected from the group consisting of hydrogen, alkyl, substituted alkyl, aryl, substituted aryl, and —CH$_2$CHR[7]NR[10]R[11] where R[7] is as defined above and R[10] and R[11] are independently selected from the group consisting of hydrogen and alkyl; and
p is an integer such that the molecular weight of the POAM moiety ranges from about 100 to 100,000.

13. A conjugate according to claim 1 wherein, when Ar[2] contains a POAM moiety, Ar[2], the POAM moiety and optional linker are represented by the formula:

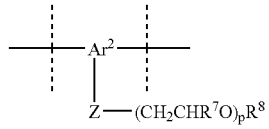

Z is selected from the group consisting of a covalent bond, a linking group of from 1 to 40 atoms, —O—, —S— and —NR[9]—, where R[9] is selected from the group consisting of hydrogen and C$_1$-C$_5$ alkyl,
R[7] is selected from the group consisting of hydrogen and methyl;
R[8] is selected from the group consisting of hydrogen, alkyl, substituted alkyl, aryl, substituted aryl, and —CH$_2$CHR[7]NR[10]R[11] where R[7] is as defined above and $R^{10}$ and $R^{11}$ are independently selected from the group consisting of hydrogen and alkyl; and p is an integer such that the molecular weight of the POAM moiety ranges from about 100 to 100,000.

14. A conjugate according to claim 1 wherein V does not contain a POAM moiety and —YC(O)V is selected from the group consisting of:
(piperidin-1-yl)C(O)O—,
(piperidin-4-yl)C(O)O—,
(1-methylpiperidin-4-yl)C(O)O—,
(4-hydroxypiperidin-1-yl)C(O)O—,
(4-formyloxypiperidin-1-yl)C(O)O—,
(4-ethoxycarbonylpiperidin-1-yl)C(O)O—,
(4-carboxylpiperidin-1-yl)C(O)O—,
(3-hydroxymethylpiperidin-1-yl)C(O)O—,
(4-hydroxymethylpiperidin-1-yl)C(O)O—,
(4-phenyl-1-Boc-piperidin-4-yl)-C(O)O—,
(4-piperidon-1-yl ethylene ketal)C(O)O—,
(piperazin-4-yl)-C(O)O—,
(1-Boc-piperazin-4-yl)-C(O)O—,
(4-methylpiperazin-1-yl)C(O)O—,
(4-methylhomopiperazin-1-yl)C(O)O—,
(4-(2-hydroxyethyl)piperazin-1-yl)C(O)O—,
(4-phenylpiperazin-1-yl)C(O)O—,
(4-(pyridin-2-yl)piperazin-1]-yl)C(O)O—,
(4-(4-trifluoromethylpyridin-2-yl)piperazin-1-yl)C(O)O—,
(4-(pyrimidin-2-yl)piperazin-1-yl)C(O)O—,
(4-acetylpiperazin-1-yl)C(O)O—,
(4-(phenylC(O)—) piperazin-1-yl)C(O)O—,
(4-(pyridin-4'-yl C(O)-)piperazin-1-yl)C(O)O,
(4-(phenylNHO(O)—) piperazin-1-yl)C(O)O—,
(4-(phenylNHO(S)—) piperazin-1-yl)C(O)O—,
(4-methanesulfonylpiperazin-1-yl-C(O)O—,
(4-trifluoromethanesulfonylpiperazin-1-yl-C(O)O—,
(morpholin-4-yl)C(O)O—,
(thiomorpholin-4-yl)C(O)O—,
(thiomorpholin-4'-yl sulfone)-C(O)O—, (pyrrolidin-1-yl)C(O)O—,
(2-methylpyrrolidin-1-yl)C(O)O—,
(2-(methoxycarbonyl)pyrrolidin-1-yl)C(O)O—, and
(2-(hydroxymethyl)pyrrolidin-1-yl)C(O)O.

15. The conjugate according to claim 1 wherein —YC(O)V is selected from the group consisting of:

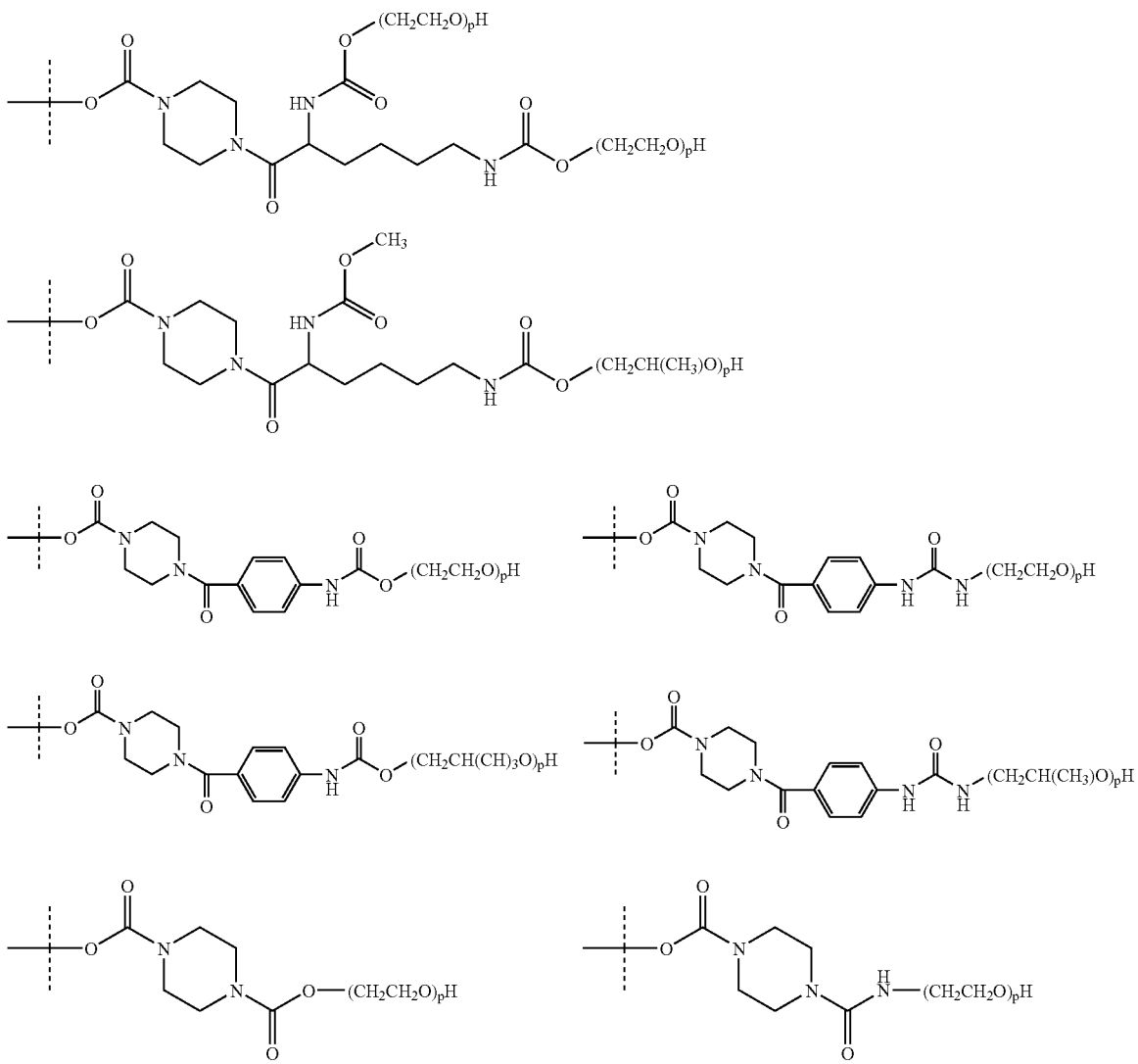

-continued
107
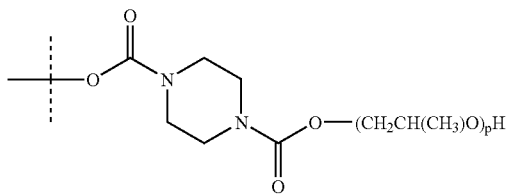
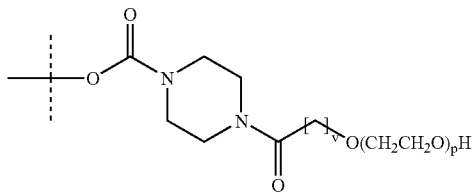
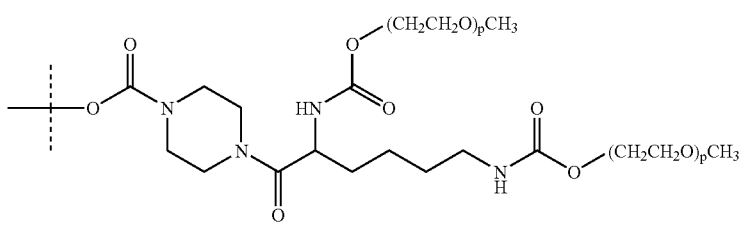
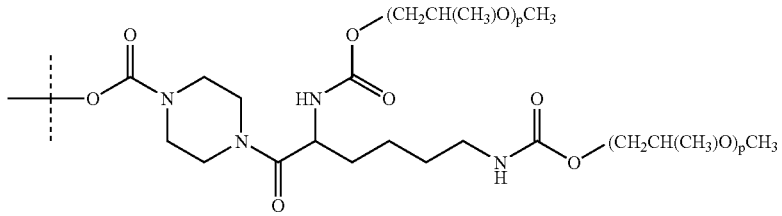
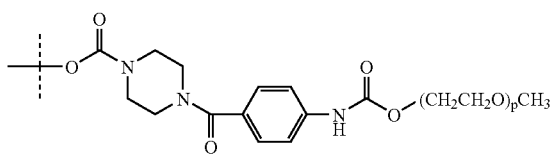
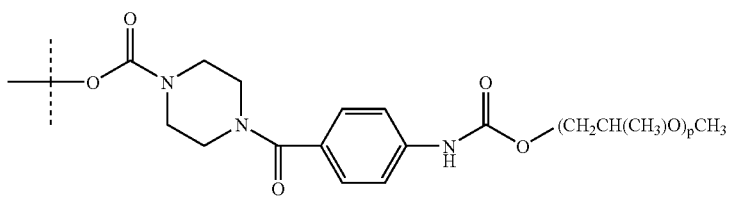
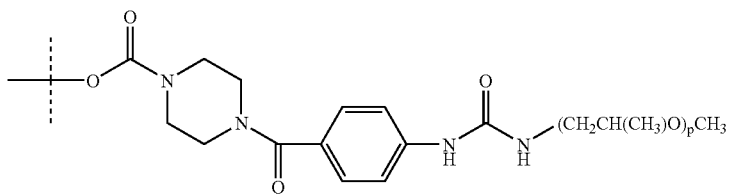
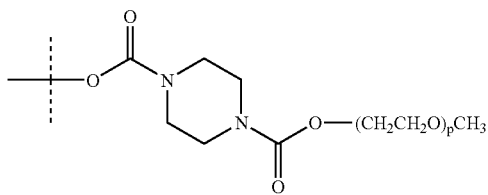
108
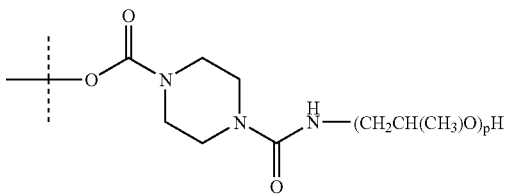
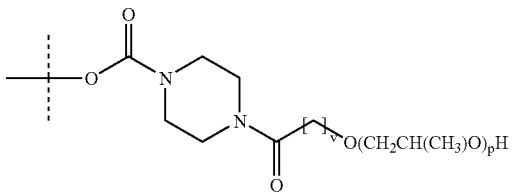
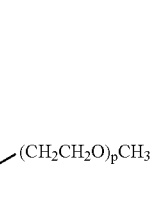
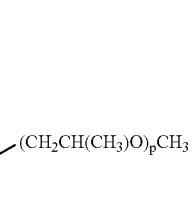
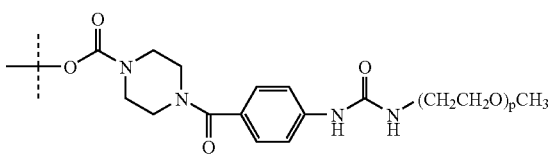
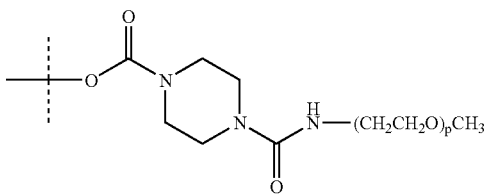

-continued
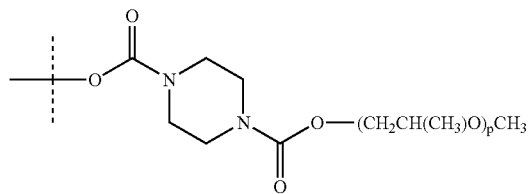
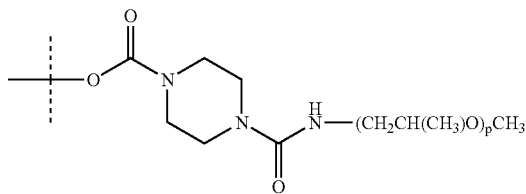
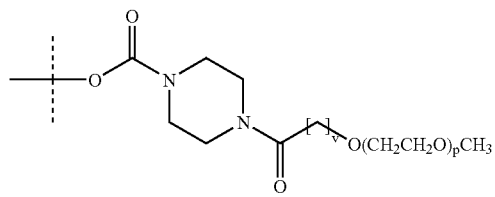
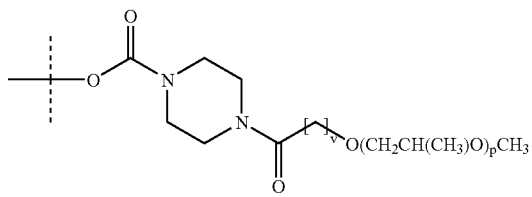
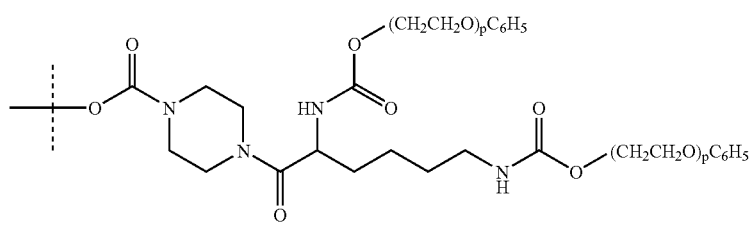
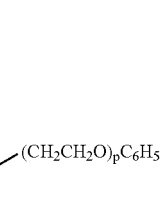
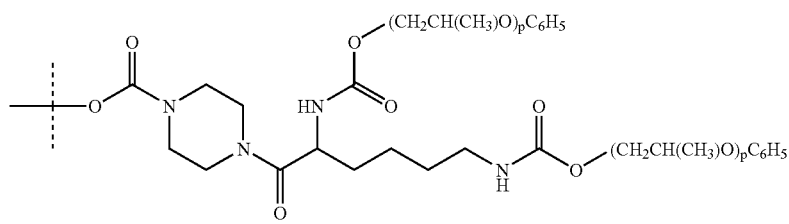
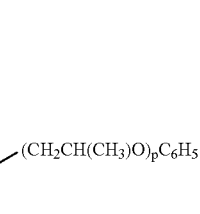
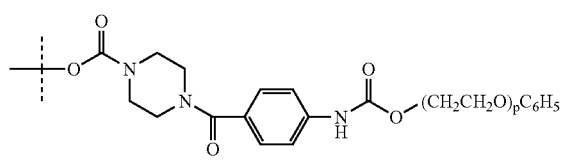
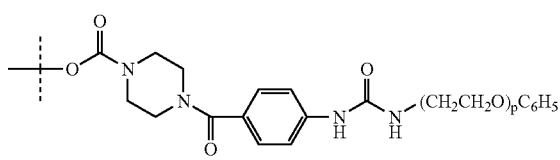
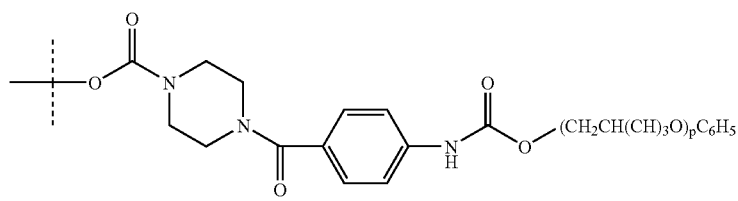
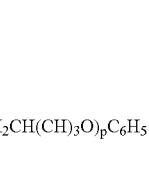
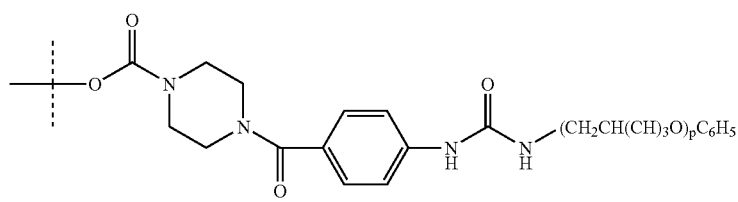
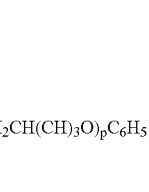
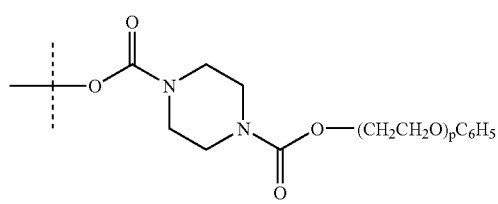
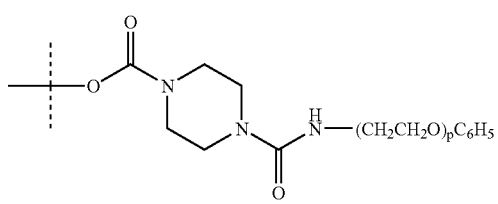

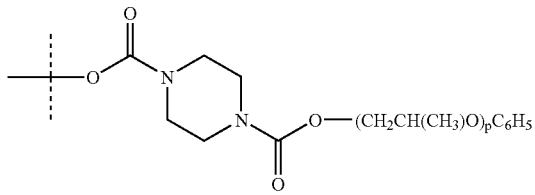
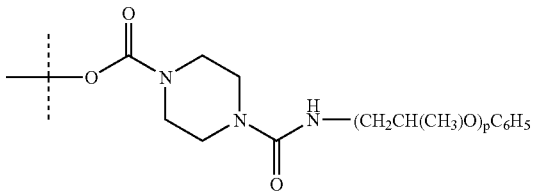
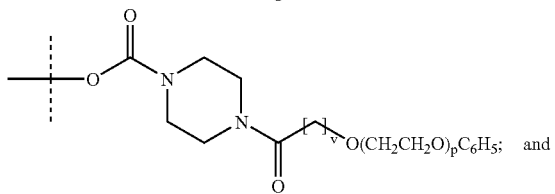
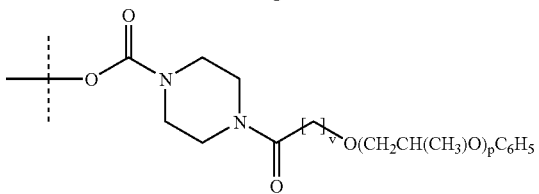
where $C_6H_5$ is phenyl and p is an integer such that the molecular weight of the POAM moiety ranges from about 100 to 100,000 and v is 1 to 5.
16. A conjugate according to claim 1, selected from the group consisting of:
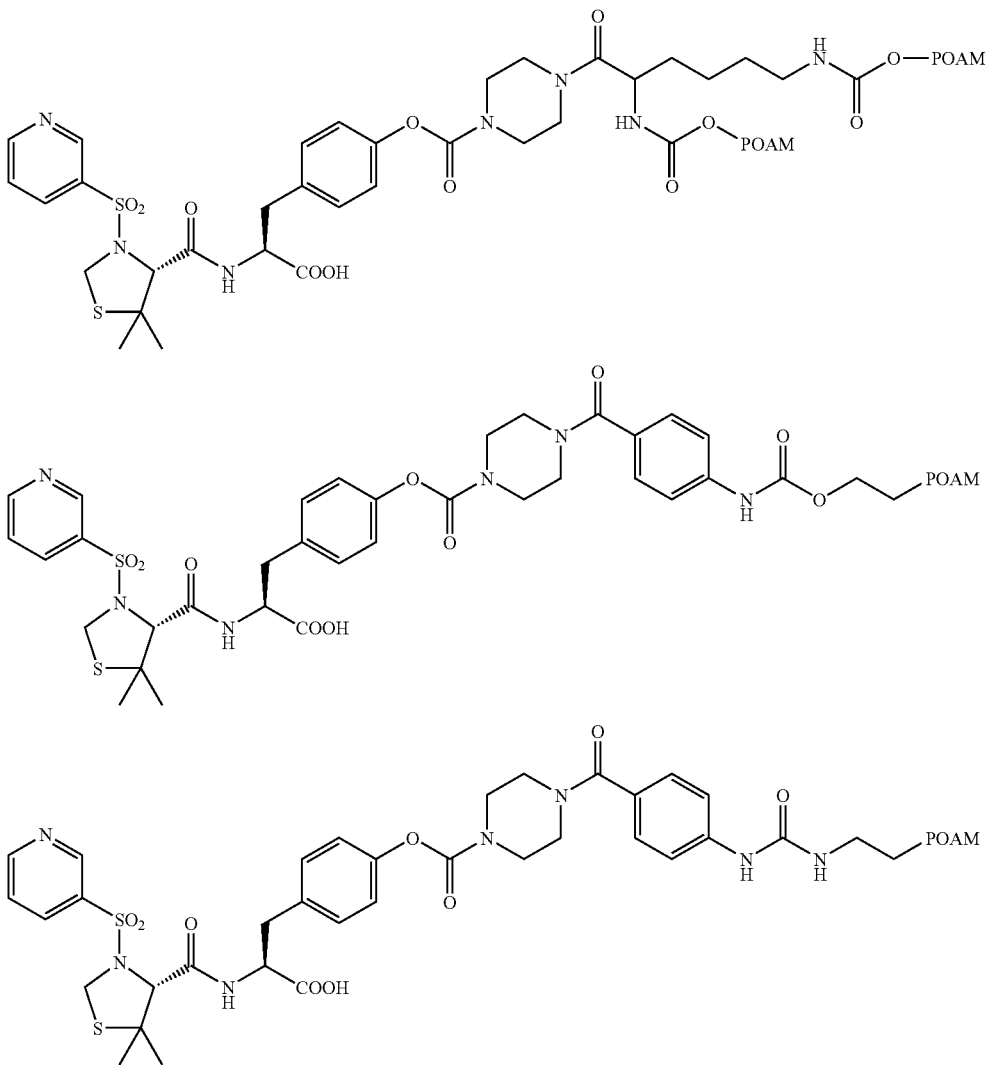

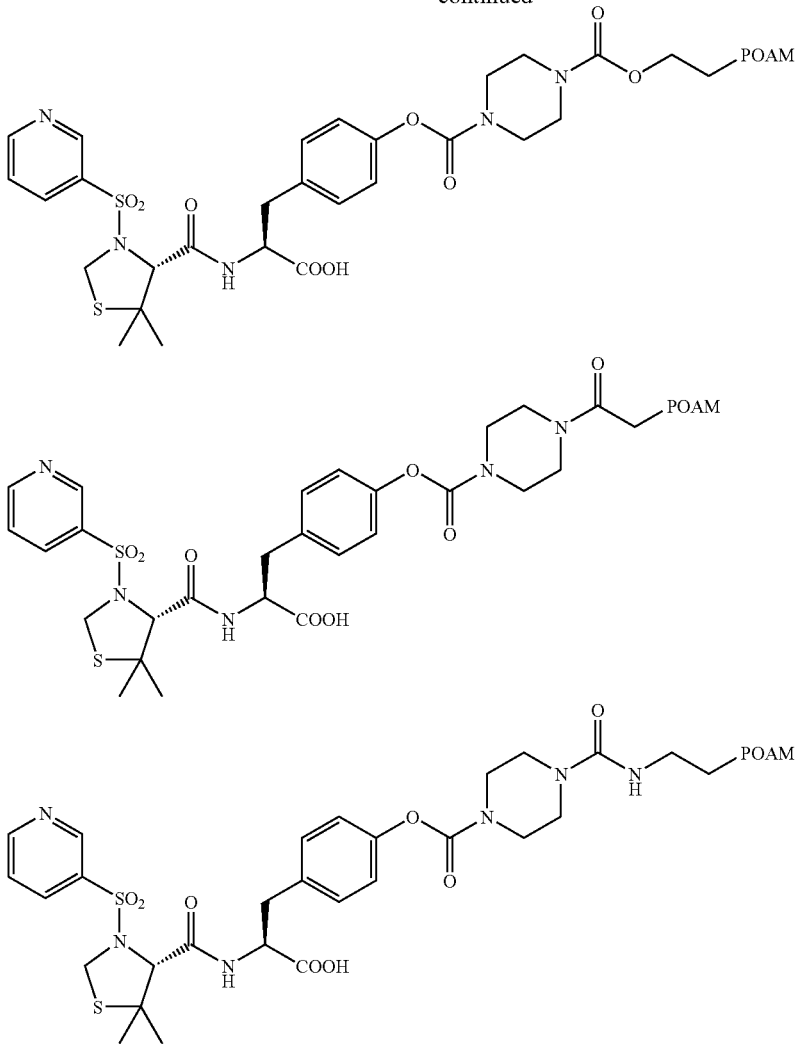

and pharmaceutically acceptable salts thereof;

where, in each case, POAM is a methyl capped polyalkylene oxide group having a molecular weight (Mw) of approximately 20,000.

17. A pharmaceutical composition comprising a pharmaceutically acceptable carrier and a therapeutically effective amount of a conjugate according to claim 1 or mixtures thereof.

18. A pharmaceutical composition according to claim 17 wherein the pharmaceutically acceptable carrier is suitable for parenteral administration.

19. A pharmaceutical composition according to claim 17 wherein the pharmaceutically acceptable carrier is suitable for subcutaneous administration.

20. A pharmaceutical composition according to claim 17 wherein the pharmaceutically acceptable carrier is suitable for administration by infusion.

21. A pharmaceutical composition according to claim 17 wherein the pharmaceutically acceptable carrier is suitable for administration by injection.

22. A pharmaceutical composition according to claim 17 wherein the pharmaceutically acceptable carrier is suitable for oral administration.

23. A pharmaceutical composition according to claim 17 wherein the pharmaceutically acceptable carrier is suitable for rectal administration.

* * * * *